(12) United States Patent
Scott et al.

(10) Patent No.: US 10,072,025 B2
(45) Date of Patent: Sep. 11, 2018

(54) ETHYL N-BOC PIPERIDINYL PYRAZOLO PYRIDONES AS JANUS KINASE INHIBITORS

(71) Applicant: Merck Sharp & Dohme Corp., Rahway, NJ (US)

(72) Inventors: Mark E. Scott, Edmonton (CA); David Guerin, Natick, MA (US); Danielle Molinari, Brookline, MA (US); Sam Kattar, Sudbury, MA (US); Peter Fuller, Wakefield, MA (US); Christopher Dinsmore, Newton, MA (US); Norman Kong, Jiangsu (CN); Yunfeng Bai, Beijing (CN); Jianmin Fu, Beijing (CN); Yumei Liu, Beijing (CN); Zhixiang Zheng, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/519,740

(22) PCT Filed: Oct. 21, 2015

(86) PCT No.: PCT/US2015/056541
§ 371 (c)(1),
(2) Date: Apr. 17, 2017

(87) PCT Pub. No.: WO2016/064935
PCT Pub. Date: Apr. 28, 2016

(65) Prior Publication Data
US 2017/0240567 A1 Aug. 24, 2017

(30) Foreign Application Priority Data

Oct. 22, 2014 (WO) ................ PCT/CN2014/089139

(51) Int. Cl.
| | | |
|---|---|---|
| *C07D 519/00* | (2006.01) | |
| *C07D 471/04* | (2006.01) | |
| *A61K 31/4545* | (2006.01) | |
| *A61K 31/5377* | (2006.01) | |
| *A61K 31/538* | (2006.01) | |
| *A61K 31/55* | (2006.01) | |
| *A61K 31/553* | (2006.01) | |
| *A61K 31/554* | (2006.01) | |
| *A61K 31/541* | (2006.01) | |

(52) U.S. Cl.
CPC ........ *C07D 519/00* (2013.01); *A61K 31/4545* (2013.01); *A61K 31/538* (2013.01); *A61K 31/5377* (2013.01); *A61K 31/541* (2013.01); *A61K 31/55* (2013.01); *A61K 31/553* (2013.01); *A61K 31/554* (2013.01); *C07D 471/04* (2013.01)

(58) Field of Classification Search
CPC .................. C07D 519/00; C07D 471/04; A61K 31/4545; A61K 31/5377; A61K 31/538; A61K 31/541; A61K 31/55; A61K 31/553; A61K 31/554
See application file for complete search history.

(56) References Cited

FOREIGN PATENT DOCUMENTS

| WO | 2013036611 A1 | 3/2013 |
|---|---|---|
| WO | 2014146249 | 9/2014 |
| WO | 2014146491 | 9/2014 |
| WO | 2014146492 | 9/2014 |
| WO | 2014146493 | 9/2014 |

OTHER PUBLICATIONS

International Search Report and Written Opinion for PCT/CN2014/089139 dated Jul. 15, 2015, 16 pages.
International Search Report and Written Opinion for PCT/US2015/056541 dated Jan. 6, 2016, 7 pages.

*Primary Examiner* — Timothy R Rozof
(74) *Attorney, Agent, or Firm* — Patricia A. Shatynski; John C. Todaro

(57) ABSTRACT

The instant invention provides compounds of Formula (I) which are JAK inhibitors, and as such are useful for the treatment of JAK-mediated diseases such as rheumatoid arthritis, asthma, COPD and cancer. The present invention provides novel compounds which are inhibitors of JAKs. The invention also provides a method for the treatment and prevention of JAK-mediated diseases and disorders using the novel compounds, as well as pharmaceutical compositions containing the compounds.

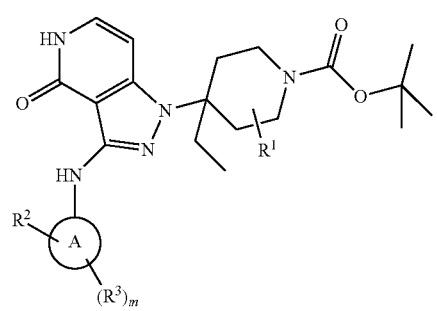

17 Claims, No Drawings

ETHYL N-BOC PIPERIDINYL PYRAZOLO PYRIDONES AS JANUS KINASE INHIBITORS

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)).

A considerable body of literature has accumulated that link the JAK/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts thereof:

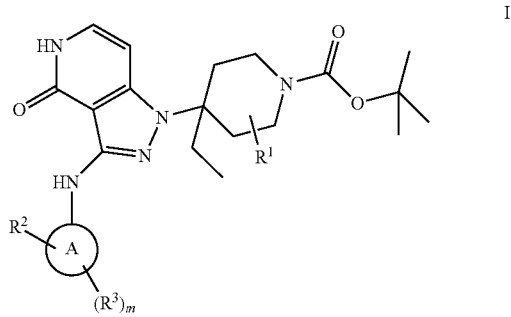

A is selected from aryl and heteroaryl;
m is 0, 1, or 2;
$R^1$ is selected from hydrogen, $C_{1-2}$alkyl, fluoro, and hydroxy;
$R^2$ is selected from:
  hydrogen
  halogen,
  oxo (=O),
  $C_{1-10}$ alkyl(oxy)$_{0-1}$ (carbonyl)$_{0-1}$ $C_{0-10}$ alkyl,
  $C_{1-10}$ heteroalkyl(oxy)$_{0-1}$ (carbonyl)$_{0-1}$$C_{0-10}$ alkyl,
  aryl $C_{0-10}$ alkyl(oxy)$_{0-1}$(carbonyl)$_{0-1}$$C_{0-10}$ alkyl,
  $C_{3-12}$ cycloalkyl $C_{0-10}$ alkyl(oxy)$_{0-1}$ (carbonyl)$_{0-1}$$C_{0-10}$ alkyl,
  heteroaryl $C_{0-10}$ alkyl(oxy)$_{0-1}$ (carbonyl)$_{0-1}$$C_{0-10}$ alkyl,
  ($C_{3-12}$)heterocycloalkyl $C_{0-10}$ alkyl(oxy)$_{0-1}$ (carbonyl)$_{0-1}$ $C_{0-10}$ alkyl,
  spirocyclyl$C_{0-10}$ alkyl(oxy)$_{0-1}$ (carbonyl)$_{0-1}$ $C_{0-10}$ alkyl,
  spiroheterocyclyl$C_{1-10}$ alkyl(oxy)$_{0-1}$ (carbonyl)$_{0-1}$$C_{0-10}$ alkyl,
  $C_{0-10}$ alkylamino$C_{0-10}$ alkyl,
  ($C_{1-10}$)heteroalkylamino$C_{0-10}$alkyl,
  ($C_{1-10}$)heteroalkylamino$C_{0-10}$alkyl,
  $C_{3-12}$ cycloalkyl $C_{0-10}$ alkylamino$C_{0-10}$ alkyl,
  aryl $C_{0-10}$ alkylamino$C_{0-10}$ alkyl,
  heteroaryl $C_{0-10}$ alkylamino$C_{0-10}$ alkyl,
  ($C_{3-12}$)heterocycloalkyl $C_{0-10}$ alkylamino$C_{0-10}$ alkyl, $C_{1-10}$ alkylsulfonyl,
$C_{1-10}$ heteroalkylsulfonyl,
$(C_{3-12})$cycloalkyl$C_{0-10}$alkylsulfonyl,
$(C_{3-12})$ heterocycloalkyl$C_{0-10}$alkylsulfonyl,
heteroaryl$C_{0-10}$ alkylsulfonyl,
aryl$C_{0-10}$ alkylsulfonyl,
—SO$_2$NH$_2$,
—SO$_2$NH($C_{1-6}$alkyl),
—SO$_2$N($C_{1-6}$alkyl)$_2$,
$C_{1-10}$ heteroalkylsulfamoyl,
$(C_{3-12})$cycloalkyl$C_{0-10}$ alkylsulfamoyl,
$(C_{3-12})$ heterocycloalkyl$C_{0-10}$ alkylsulfamoyl,
heteroaryl$C_{0-10}$ alkylsulfamoyl,
aryl$C_{0-10}$ alkylsulfamoyl,
$(C_{1-10}$ alkyl$)_{1-2}$amino,
—CO$_2$($C_{0-10}$ alkyl),
—($C_{0-10}$ alkyl)CO$_2$H,
—SO$_2$CF$_3$,
—SO$_2$CF$_2$H,
—SO$_2$CH$_2$CF$_3$,
$C_{1-10}$ alkylsulfinyl,
$C_{1-4}$acylamino$C_{0-10}$ alkyl,
hydroxy,
—($C_{1-10}$ alkyl)OH,
$C_{1-10}$ alkoxy$C_{0-10}$ alkyl,
cyano,
($C_{1-6}$alkyl)cyano,
cyano$C_{1-6}$alkyl, and
$C_{1-6}$haloalkyl.
wherein $R^2$ is optionally independently substituted by 0, 1, 2, or 3 $R^4$;
each $R^3$ is independently selected from:
$C_{1-10}$ alkyl,
$(C_{3-12})$heterocycloalkyl $C_{0-10}$ alkyl,
$C_{1-10}$ alkoxy$C_{0-10}$ alkyl,
halogen,
$C_{1-6}$haloalkyl, and
oxo;
each $R^4$ is independently selected from:
$C_{1-10}$ alkyl,
$(C_{3-12})$heterocycloalkyl $C_{0-10}$ alkyl,
$C_{1-10}$ alkoxy$C_{0-10}$ alkyl,
$C_{0-10}$ alkylamino$C_{0-10}$ alkyl,
halogen,
hydroxy,
—($C_{1-10}$ alkyl)OH,
$C_{1-6}$haloalkyl, and
oxo.

Representative compounds of the instant invention include, but are not limited to the following compounds and their pharmaceutically acceptable salts thereof:

tert-butyl 4-(3-(4-(N,N-dimethylsulfamoyl)phenylamino)-4-oxo-4,5-dihydropyrazolo[4,3-c]pyridin-1-yl)-4-ethylpiperidine-1-carboxylate;
2-tert-butyl-5-[[1-(1-tert-butyl-6-ethyl-2-oxo-1,3-oxazocan-6-yl)-4-oxo-1H,4H,5H-pyrazolo[4,3-c]pyridin-3-yl]amino]-2,3-dihydro-1,2-benzothiazole-1,1-dione;
tert-butyl 4-ethyl-4-(3-(4-(methylsulfonyl)phenylamino)-4-oxo-4,5-dihydropyrazolo[4,3-c]pyridin-1-yl)piperidine-1-carboxylate;
tert-butyl 4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-ethylpiperidine-1-carboxylate;
tert-butyl 4-(3-(2-(4,4-difluoro-1-methylcyclohexyl)-1-oxoisoindolin-5-ylamino)-4-oxo-4,5-dihydropyrazolo[4,3-c]pyridin-1-yl)piperidine-1-carboxylate;
tert-butyl 4-ethyl-4-(4-oxo-3-(4-(1-(2,2,2-trifluoroethyl)piperidin-4-yl)phenylamino)-4,5-dihydropyrazolo[4,3-c]pyridin-1-yl)piperidine-1-carboxylate;
tert-butyl 4-ethyl-4-(3-(4-(1-methylpiperidin-4-yl)phenylamino)-4-oxo-4,5-dihydropyrazolo[4,3-c]pyridin-1-yl)piperidine-1-carboxylate;
tert-butyl 4-ethyl-4-(3-{[2-(oxan-4-yl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;
(S)-tert-butyl 4-ethyl-4-(3-((3-methyl-4-(3-methylmorpholine-4-carbonyl)phenyl)amino)-4-oxo-4,5-dihydro-1H-pyrazolo[4,3-c]pyridin-1-yl)piperidine-1-carboxylate;
tert-butyl 4-ethyl-4-(3-((3-methyl-4-(3-methylmorpholine-4-carbonyl)phenyl)amino)-4-oxo-4,5-dihydro-1H-pyrazolo[4,3-c]pyridin-1-yl)piperidine-1-carboxylate;
(R)-tert-butyl-4-ethyl-4-(3-(3-methyl-4-(2-methylmorpholine-4-carbonyl)phenylamino)-4-oxo-4,5-dihydropyrazolo[4,3-c]pyridin-1-yl)piperidine-1-carboxylate;
(S)-tert-butyl-4-ethyl-4-(3-(3-methyl-4-(2-methylmorpholine-4-carbonyl)phenylamino)-4-oxo-4,5-dihydropyrazolo[4,3-c]pyridin-1-yl)piperidine-1-carboxylate;
tert-butyl-4-ethyl-4-(3-(3-methyl-4-(2-methylmorpholine-4-carbonyl)phenylamino)-4-oxo-4,5-dihydropyrazolo[4,3-c]pyridin-1-yl)piperidine-1-carboxylate;
tert-butyl 4-ethyl-4-(3-((3-methyl-4-(morpholine-4-carbonyl)phenyl)amino)-4-oxo-4,5-dihydro-1H-pyrazolo[4,3-c]pyridin-1-yl)piperidine-1-carboxylate;
(R)-tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
(S)-tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
tert-butyl-4-ethyl-4-(3-(3-methyl-4-(morpholine-4-carbonyl)phenylamino)-4-oxo-4,5-dihydropyrazolo[4,3-c]pyridin-1-yl)piperidine-1-carboxylate;
tert-butyl 4-ethyl-4-(3-((3-fluoro-4-(morpholine-4-carbonyl)phenyl)amino)-4-oxo-4,5-dihydro-1H-pyrazolo[4,3-c]pyridin-1-yl)piperidine-1-carboxylate;
tert-butyl 4-(3-((4-(3-oxa-8-azabicyclo[3.2.1]octane-8-carbonyl)-3-methylphenyl)amino)-4-oxo-4,5-dihydro-1H-pyrazolo[4,3-c]pyridin-1-yl)-4-ethylpiperidine-1-carboxylate;
tert-butyl 4-ethyl-4-(3-((3-methyl-4-(2-oxa-6-azaspiro[3.3]heptane-6-carbonyl)phenyl)amino)-4-oxo-4,5-dihydro-1H-pyrazolo[4,3-c]pyridin-1-yl)piperidine-1-carboxylate;
tert-butyl 4-(3-((4-((1R,4R)-2-oxa-5-azabicyclo[2.2.1]heptane-5-carbonyl)-3-methylphenyl)amino)-4-oxo-4,5-dihydro-1H-pyrazolo[4,3-c]pyridin-1-yl)-4-ethylpiperidine-1-carboxylate
tert-butyl 4-(3-((3-(cyanomethyl)phenyl)amino)-4-oxo-4,5-dihydro-1H-pyrazolo[4,3-c]pyridin-1-yl)-4-ethylpiperidine-1-carboxylate;
tert-butyl 4-(3-(4-((3S,5R)-3,5-dimethylmorpholine-4-carbonyl)-3-methylphenylamino)-4-oxo-2,3,4,5-tetrahydropyrazolo[4,3-c]pyridin-1-yl)-4-ethylpiperidine-1-carboxylate;
tert-butyl 4-(3-(4-((3R,5R)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;
tert-butyl 4-(3-(4-((3S,5S)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;

tert-butyl 4-(3-(4-(3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;

tert-butyl 4-ethyl-4-(3-(3-methyl-4-(thiomorpholine-4-carbonyl)phenylamino)-4-oxo-4,5-dihydropyrazolo[4,3-c]pyridin-1-yl)piperidine-1-carboxylate;

tert-butyl 4-(3-(4-((1S,4S)-5-oxa-2-aza-bicyclo[2.2.1]heptane-2-carbonyl)-3-methylphenylamino)-4-oxo-4,5-dihydropyrazolo[4,3-c]pyridin-1-yl)-4-ethylpiperidine-1-carboxylate;

tert-butyl 4-ethyl-4-(4-oxo-3-(4-(piperidin-4-yl)phenylamino)-4,5-dihydropyrazolo[4,3-c]pyridin-1-yl)piperidine-1-carboxylate;

tert-butyl 4-ethyl-4-(3-((3-ethyl-4-(morpholine-4-carbonyl)phenyl)amino)-4-oxo-4,5-dihydro-1H-pyrazolo[4,3-c]pyridin-1-yl)piperidine-1-carboxylate;

tert-butyl 4-(3-(3-(difluoromethyl)-4-(thiomorpholine-4-carbonyl)phenylamino)-4-oxo-4,5-dihydropyrazolo[4,3-c]pyridin-1-yl)-4-ethylpiperidine-1-carboxylate;

tert-butyl 4-(3-(4-(4,4-difluoropiperidine-1-carbonyl)-3-methylphenylamino)-4-oxo-4,5-dihydropyrazolo[4,3-c]pyridin-1-yl)-4-ethylpiperidine-1-carboxylate;

tert-butyl-4-ethyl-4-(3-(3-methyl-4-(thiomorpholine-4-carbonyl)phenylamino)-4-oxo-4,5-dihydropyrazolo[4,3-c]pyridin-1-yl)piperidine-1-carboxylate;

(R)-tert-butyl-4-ethyl-4-(3-(3-methyl-4-(3-methylmorpholine-4-carbonyl)phenylamino)-4-oxo-4,5-dihydropyrazolo[4,3-c]pyridin-1-yl)piperidine-1-carboxylate;

tert-butyl 4-ethyl-4-(3-(3-ethyl-4-(thiomorpholine-4-carbonyl)phenylamino)-4-oxo-4,5-dihydropyrazolo[4,3-c]pyridin-1-yl)piperidine-1-carboxylate;

tert-butyl 4-ethyl-4-(3-((2-(1-methylpiperidin-4-yl)-1,1-dioxido-2,3-dihydrobenzo[d]isothiazol-5-yl)amino)-4-oxo-4,5-dihydro-1H-pyrazolo[4,3-c]pyridin-1-yl)piperidine-1-carboxylate;

(S)-tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;

(R)-tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;

tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;

tert-butyl 4-ethyl-4-(3-(3-methyl-4-(pyrrolidine-1-carbonyl)phenylamino)-4-oxo-4,5-dihydropyrazolo[4,3-c]pyridin-1-yl)piperidine-1-carboxylate;

(S)-tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

(R)-tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

(R)-tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;

(S)-tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;

tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;

(S)-tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;

(R)-tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;

tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;

tert-butyl 4-ethyl-4-(3-(2-fluoropyridin-4-ylamino)-4-oxo-4,5-dihydropyrazolo[4,3-c]pyridin-1-yl)piperidine-1-carboxylate;

(S) tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;

(R) tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;

tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;

(R) tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(S) tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(S) tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

(R) tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

4-((1-(1-(tert-butoxycarbonyl)-4-ethylpiperidin-4-yl)-4-oxo-4,5-dihydro 1H-pyrazolo[4,3-c]pyridin-3-yl)amino)-2-methylbenzoic acid;

tert-butyl-4-ethyl-4-(3-((3-methyl-4-(2-oxomorpholine-4-carbonyl)phenyl)amino)-4-oxo-4,5-dihydro-1H-pyrazolo[4,3-c]pyridin-1-yl)piperidine-1-carboxylate;

tert-butyl 4-[3-({4-[(2,2-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-(3-{[3-methyl-4-(6-oxa-9-azaspiro[4.5]dec-9-ylcarbonyl)phenyl]amino}-4-oxo-4,5-dihydro-1H-pyrazolo[4,3-c]pyridin-1-yl)piperidine-1-carboxylate;

tert-butyl 4-{3-[(4-{[(2R,6S)-2,6-dimethylmorpholin-4-yl]carbonyl}-3-methylphenyl)amino]-4-oxo-4,5-dihydro-1H-pyrazolo[4,3-c]pyridin-1-yl}-4-ethylpiperidine-1-carboxylate;

tert-butyl 4-[3-({4-[(3,3-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-[3-({3-methyl-4-[(1R,5S)-6-oxa-3-azabicyclo[3.1.1]hept-3-ylcarbonyl]phenyl}amino)-4-oxo-4,5-dihydro-1H-pyrazolo[4,3-c]pyridin-1-yl]piperidine-1-carboxylate;

tert-butyl 4-{3-[(4-{[(2S,6S)-2,6-dimethylmorpholin-4-yl]carbonyl}-3-methylphenyl)amino]-4-oxo-4,5-dihydro-1H-pyrazolo[4,3-c]pyridin-1-yl}-4-ethylpiperidine-1-carboxylate;

tert-butyl 4-ethyl-4-{3-[(3-methyl-4-{[(3R)-3-(1-methyl-ethyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-(3-{[3-methyl-4-(1,4-thiazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-(3-{[3-methyl-4-(1,4-oxazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({3-methyl-4-[(1-oxidothiomorpholin-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-{3-[(3-methyl-4-{[(3R)-3-(1-methyl-ethyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-(3-{[3-methyl-4-(1,4-thiazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-(3-{[3-methyl-4-(1,4-oxazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({3-methyl-4-[(1-oxidothiomorpholin-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(4-thiomorpholin-4-ylpiperidin-1-yl)carbonyl]phenyl}amino)-4-oxo-4,5-dihydro-1H-pyrazolo[4,3-c]pyridin-1-yl]piperidine-1-carboxylate;

tert-butyl 4-[3-({4-[(2,3-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-{3-[(3-methyl-4-{[3-(2R-methylpropyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-{3-[(3-methyl-4-{[3-(2S-methylpropyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-{3-[(3-methyl-4-{[3-(methylpropyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-[3-({3-methyl-4-[(methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(6R-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(6S-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-(3-{[3-methyl-4-(2-oxa-5-azabicyclo[4.1.0]hept-5-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3R-methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate and tert-butyl 4-ethyl-4-[3-({3S-methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate.

The invention also encompasses pharmaceutical compositions containing a compound of Formula I, and methods for treatment or prevention of JAK mediated diseases using compounds of Formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkoxy" represents a linear or branched alkyl group of indicated number of carbon atoms attached through an oxygen bridge.

"Acyl" means a —C(O)R radical where R is optionally substituted alkyl, alkenyl, cycloalkyl, heterocycloalkyl, aryl, heteroaryl, etc.

"Acylamino" means a —NRR' radical where R is H, OH, or alkoxy and R' is acyl, as defined herein.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms is substituted by a heteroatom independently chosen from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include CH₂NH₂, CH₂CH₂NHCH₃ and CH(N(CH₃)₂)CH₃.

The term "$C_0$—" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

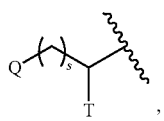

wherein s is an integer equal to zero, 1 or 2, the structure is

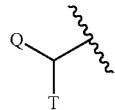

when s is zero.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, NH₂ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

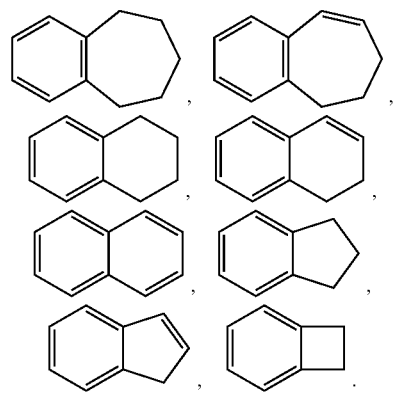

"Cyanoalkyl" refers to an alkyl group as described above in which one hydrogen atom has been replaced by a cyano group. Examples include CH₂CN, CH₂CH₂CN and CH(CN)CH₃.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbomane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like. The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes —CF₃, —CF₂CF₃, CHFCH₃, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. For a bicyclic system, the rings may be fused across two adjacent ring atoms (e.g., quinoline), at one ring carbon atom (e.g., 1,4-dioxaspiro[4.5]decane), or may be bridged groups (e.g. 8-azabicyclo[3.2.1]octanyl,). "Heterocyclyl" therefore includes heteroaryls, as well as dihydro and tetrathydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]

pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or polycyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

"Heteroaryl" means an aromatic monocyclic or multicyclic ring system having 5 to 14 ring atoms, preferably 5 to 10 ring atoms, in which one or more of the ring atoms is an element other than carbon, for example nitrogen, oxygen or sulfur, alone or in combination. A nitrogen atom of a heteroaryl can be optionally oxidized to the corresponding N-oxide. Non limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, pyrazolo[1,5-a]pyrimidinyl, imidazo[1,2-a]pyridinyl, imidazo[2,1-b]thiazolyl, indazolyl, benzofurazanyl, indolyl, azaindolyl, 20 benzimidazolyl, benzothienyl, quinolinyl, imidazolyl, thienopyridyl, quinazolinyl, thienopyrimidyl, pyrrolopyridyl, imidazopyridyl, isoquinolinyl, naphthyridinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

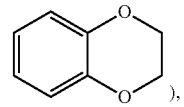), imidazo(2,1-b)(1,3)thiazole (i.e.,

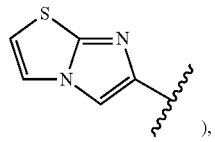 [SMILES: *c1cn2ccsc2n1]), and benzo-1,3-dioxolyl (i.e.,

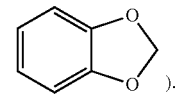).

In certain contexts herein,

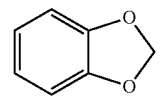

is alternatively referred to as phenyl having as a substituent methylenedioxy attached to two adjacent carbon atoms.

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic

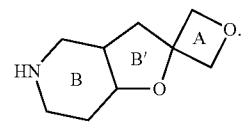

In one embodiment, all rings of the spirocyclyl system are saturated. In another embodiment, the individual rings of the spirocyclyl system are selected from both saturated and unsaturated rings.

For example a heteroalicyclic, spirocyclyl, spiroheterocyclyl, or "spiroheterocyclic ring," as used herein, refers to a bicyclic heterocyclic ring as defined above wherein the two rings are joined through a common ring carbon atom. In one embodiment, a spiroheterocyclic ring is a 3- to 12-membered ring system containing one to three heteroatoms, e.g., one to two heteroatoms, selected from the group consisting of N and O. Non-limiting examples of spiroheterocyclyl, spiroheterocyclic rings include 2-oxa-6-azaspiro[3,3]heptane, 6-oxa-9-azaspiro[4.5]dec-9-yl, and 1,4-dioxaspiro[4.5]decane.

Non-limiting examples of a carbocyclic spirocyclyl systems comprising include: spiro[2.2]pentane, spiro[cylclobutane-1,2'-indene], spiro[4.4]nonane, and spiro[4.5]decane.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "sulfamoyl" is a suffix to denote radicals derived from sulfamide such as $-SO_2NH_2$, $-SO_2NHR$ and $-SO_2N(RR^1)$.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in Formula I its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

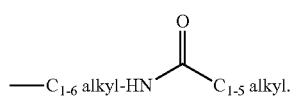

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "$CH_3$", e.g. "—$CH_3$" or using a straight line representing the presence of the methyl group, e.g. "⸺", i.e., "$\xi$⸺$CH_3$" and "$\xi$⸺" have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

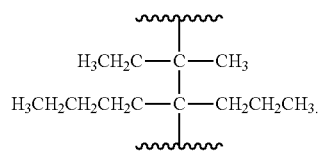

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

In one embodiment of the invention, A is selected from:

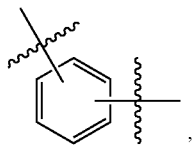

isoindolinyldiyl, pyridinyldiyl,

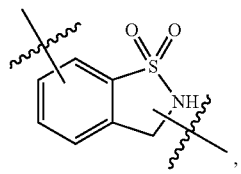

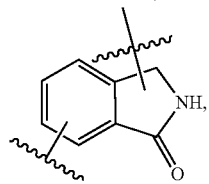

and indolinyldiyl.

In a variant of this embodiment, A is selected from:

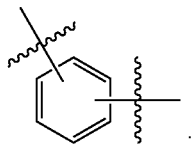

In another variant, A is selected from pyridinyldiyl,

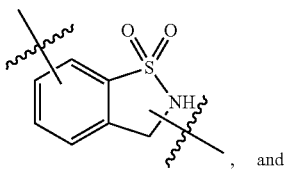, and

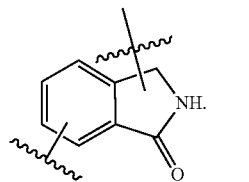

In one embodiment of the invention, $R^1$ is selected from hydrogen, $C_{1-2}$alkyl, fluoro, and hydroxy. In a variant of this embodiment, $R^1$ is hydrogen or fluoro. In yet another embodiment $R^1$ is hydrogen.

In one embodiment of the invention, m is 0 or 1. In another embodiment, m is 2.

In one embodiment of the invention, $R^2$ is selected from:
hydrogen
halogen,
oxo (=O),
$C_{1-10}$ alkyl(oxy)$_{0-1}$(carbonyl)$_{0-1}$ $C_{0-10}$ alkyl,
$C_{1-10}$ heteroalkyl(oxy)$_{0-1}$ (carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$ (carbonyl)$_{0-1}C_{0-10}$ alkyl,
$(C_{3-12})$heterocycloalkyl $C_{0-10}$ alkyl(oxy)$_{0-1}$ (carbonyl)$_{0-1}C_{0-10}$ alkyl,
spirocyclyl$C_{0-10}$ alkyl(oxy)$_{0-1}$(carbonyl)$_{0-1}C_{0-10}$ alkyl,
spiroheterocyclyl$C_{0-10}$ alkyl(oxy)$_{0-1}$ (carbonyl)$_{0-1}C_{0-10}$ alkyl,
$C_{0-10}$ alkylamino$C_{0-10}$ alkyl,
$C_{1-10}$ alkylsulfonyl,
$C_{1-10}$ heteroalkylsulfonyl,
$(C_{3-12})$cycloalkyl$C_{0-10}$alkylsulfonyl,
$(C_{3-12})$heterocycloalkyl$C_{0-10}$ alkylsulfonyl,
heteroaryl$C_{0-10}$ alkylsulfonyl,
aryl$C_{0-10}$ alkylsulfonyl,
—SO$_2$NH($C_{1-6}$alkyl),
—SO$_2$N($C_{1-6}$alkyl)$_2$,
$C_{1-10}$ heteroalkylsulfamoyl,
$(C_{3-12})$cycloalkyl$C_{0-10}$ alkylsulfamoyl,
$(C_{3-12})$hetercyclooalkyl$C_{0-10}$ alkylsulfamoyl,
$(C_{1-10}$ alkyl)$_{1-2}$amino,
—CO$_2$($C_{0-10}$ alkyl),
—($C_{0-10}$ alkyl)CO$_2$H,
hydroxy,
—($C_{1-10}$ alkyl)OH,
$C_{1-10}$ alkoxy$C_{0-10}$ alkyl,
cyano,
cyano$C_{1-6}$alkyl, and
$C_{1-6}$haloalkyl.
wherein $R^2$ is optionally independently substituted by 0, 1, 2, or 3 $R^4$.

In another embodiment, $R^2$ is selected from:
hydrogen
halogen,
oxo (=O),
$C_{1-10}$ alkyl(oxy)$_{0-1}$ (carbonyl)$_{0-1}C_{0-10}$ alkyl,
$C_{3-12}$ cycloalkyl $C_{0-10}$ alkyl(oxy)$_{0-1}$ (carbonyl)$_{0-1}C_{0-10}$ alkyl,
$(C_{3-12})$heterocycloalkyl $C_{0-10}$ alkyl(oxy)$_{0-1}$ (carbonyl)$_{0-1}$ $C_{0-10}$ alkyl,
spirocyclyl$C_{0-10}$ alkyl(oxy)$_{0-1}$ (carbonyl)$_{0-1}C_{0-10}$ alkyl,
spiroheterocyclyl$C_{0-10}$ alkyl(oxy)$_{0-1}$ (carbonyl)$_{0-1}C_{0-10}$ alkyl,
$C_{0-10}$ alkylamino$C_{0-10}$ alkyl,
$C_{1-10}$ alkylsulfonyl,
$(C_{3-12})$ heterocycloalkyl$C_{0-10}$alkylsulfonyl,
—SO$_2$NH($C_{1-6}$alkyl),
—SO$_2$N($C_{1-6}$alkyl)$_2$,
—($C_{0-10}$ alkyl)CO$_2$H,
—($C_{1-10}$ alkyl)OH,
$C_{1-10}$ alkoxy$C_{0-10}$ alkyl,
cyano$C_{1-6}$alkyl, and
$C_{1-6}$haloalkyl, wherein $R^2$ is optionally independently substituted by 0, 1, 2, or 3 $R^4$.

In yet another embodiment, $R^2$ is selected from:
halogen,
$C_{1-10}$ alkyl;
$C_{3-12}$ cycloalkyl,
$(C_{3-12})$heterocycloalkyl(carbonyl)$_{0-1}$,
spiroheterocyclyl(carbonyl)$_{0-1}$,
$C_{0-10}$ alkylamino$C_{0-10}$ alkyl,
$C_{1-10}$ alkylsulfonyl,
$(C_{3-12})$ heterocycloalkylsulfonyl,
—SO$_2$NH($C_{1-6}$alkyl),
—SO$_2$N($C_{1-6}$alkyl)$_2$, —CO$_2$H,
C$_{1-10}$ alkoxyC$_{0-10}$ alkyl,
—(C$_{1-10}$ alkyl)OH,
cyanoC$_{1-6}$alkyl, and
C$_{1-6}$haloalkyl, wherein R$^2$ is optionally independently substituted by 0, 1, 2, or 3 R$^4$.

In one embodiment of the invention, R$^2$ is selected from: carboxy, (8-oxa-3-azabicyclo[3.2.1]oxtane)carbonyl, cyclohexyl, piperidinyl, morpholinylcarbonyl, azepanyl, ((1R,4R)-2-oxa-5-azabicyclo[2.2.1]heptyl)carbonyl, cyanomethyl, (2-oxa-6-azaspiro[3.3]heptyl)carbonyl, thiomorpholinylcarbonyl, ((1R,4R)-2-oxa-5-azabicyclo[2.2.1]heptyl)carbonyl, (2-oxa-5-azabicyclo[2.2.1]heptyl)carbonyl, piperidinylcarbonyl pyrrolidinylcarbonyl, pyrrolidinyl, tert-butylaminomethyl, 2,2,2-trifluoroethyl, pyrrolidinylsulfonyl, fluoro, methoxymethyl, hydroxymethyl, (6-oxa-9-azaspiro[4.5]decyl)carbonyl, ((1R,5S)6-oxa-3-azabicyclo[3.1.1]heptyl)carbonyl, (6-oxa-3-azabicyclo[3.1.1]heptyl)carbonyl 1,4-thiazepanylcarbonyl, thiazepanylcarbonyl, 1,4-oxazepanylcarbonyl, oxazepanylcarbonyl, (2-oxa-5-azabixyclo[4.1.0]heptyl)carbonyl; dimethylsulfamoyl, tert-butyl, and methylsulfonyl, wherein R$^2$ is optionally independently substituted by 0, 1, 2, or 3 R$^4$.

In one embodiment of the invention, each R$^3$ is independently selected from: C$_{1-10}$ alkyl, oxo, (C$_{3-12}$)heterocycloalkyl C$_{0-10}$ alkyl, C$_{1-10}$ alkoxyC$_{0-10}$ alkyl, halogen, and C$_{1-6}$haloalkyl. In a variant of this embodiment, each R$^3$ is independently selected from: methyl, trifluoromethyl, ethyl, trifluoroethyl, fluoro, oxo, hydroxy, isopropyl, thiomorpholinyl, isobutyl, and difluoromethyl.

In one embodiment of the invention, each R$^4$ is independently selected from: C$_{1-10}$ alkyl, (C$_{3-12}$)heterocycloalkyl C$_{0-10}$ alkyl, C$_{1-10}$ alkoxyC$_{0-10}$ alkyl, C$_{0-10}$ alkylaminoC$_{0-10}$ alkyl, halogen, hydroxy, C$_{1-6}$haloalkyl, and oxo.

In one embodiment of the invention, R$^4$ independently is selected from: methyl, fluoro, 2,2,2-trifluoroethyl, trifluoromethyl, tert-butylamino, methoxy, hydroxy, oxo, isopropyl, thiomorpholinyl, and isobutyl.

In yet another embodiment of the invention are compounds of Formula I or pharmaceutically acceptable salts thereof:

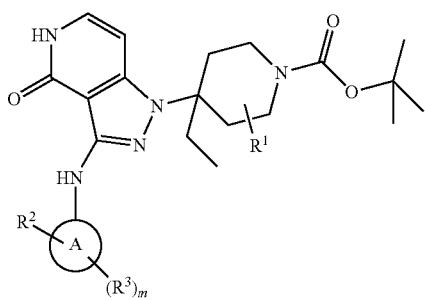

I

A is pyridinyldiyl,

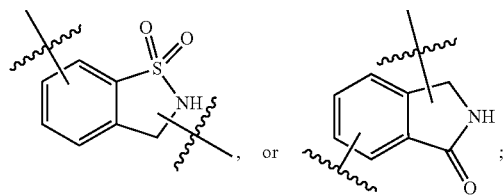

or;
m is 0, 1, or 2;
R$^1$ is hydrogen;
R$^2$ is selected from: carboxy, (8-oxa-3-azabicyclo[3.2.1]oxtane)carbonyl, cyclohexyl, piperidinyl, morpholinylcarbonyl, azepanyl, ((1R,4R)-2-oxa-5-azabicyclo[2.2.1]heptyl)carbonyl, cyanomethyl, (2-oxa-6-azaspiro[3.3]heptyl)carbonyl, thiomorpholinylcarbonyl, ((1R,4R)-2-oxa-5-azabicyclo[2.2.1]heptyl)carbonyl, (2-oxa-5-azabicyclo[2.2.1]heptyl)carbonyl, piperidinylcarbonyl, pyrrolidinylcarbonyl, pyrrolidinyl, tert-butylaminomethyl, 2,2,2-trifluoroethyl, pyrrolidinylsulfonyl, fluoro, methoxymethyl, hydroxymethyl, (6-oxa-9-azaspiro[4.5]decyl)carbonyl, ((1R,5S)6-oxa-3-azabicyclo[3.1.1]heptyl)carbonyl, (6-oxa-3-azabicyclo[3.1.1]heptyl)carbonyl 1,4-thiazepanylcarbonyl, thiazepanylcarbonyl, 1,4-oxazepanylcarbonyl, oxazepanylcarbonyl, (2-oxa-5-azabixyclo[4.1.0]heptyl)carbonyl; dimethylsulfamoyl, tert-butyl, and methylsulfonyl, wherein R$^2$ is optionally independently substituted by 0, 1, 2, or 3 R$^4$;
each R$^3$ is independently selected from: methyl, trifluoromethyl, ethyl, trifluoroethyl, fluoro, oxo, hydroxy, isopropyl, thiomorpholinyl, isobutyl, and difluoromethyl; and
each R$^4$ is selected from: methyl, fluoro, 2,2,2 trifluoroethyl, trifluoromethyl, tert-butylamino, methoxy, hydroxy, oxo, isopropyl, thiomorpholinyl, and isobutyl.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Specific embodiments of the present invention include a compound which is selected from the group consisting of the subject compounds of the examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the formulas of the invention, it is understood that both the (R) and (S) configurations of the chiral carbon, and hence both enantiomers and mixtures thereof, are embraced within the formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 recommendations. The use of the terms "salt", "solvate", "ester", "prodrug" and the like, is intended to equally apply to the salt, solvate, ester and prodrug of enantiomers, stereoisomers, rotamers, tautomers, racemates or prodrugs of the inventive compounds.

In the present application when a particular stereomeric compound is named using an "and" in the stereomeric designation, for example, ((2S and 2R)N-(1-(4-bromophenyl)-2,2,2-trifluoroethyl)-2-methylpropan-2-amine, the "and" indicates a racemic mixture of the enantiomers. That is, the individual enantiomers were not individually isolated.

When the stereomeric nomenclature includes "or", for example, tert-butyl 4-(3-(4-(((3S,5S or 3R,5R)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate, the "or" indicates that chiral resolution of racemate into individual enantiomers was accomplished but the actual optical activity of the specific enantiomer was not necessarily determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salt

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, 1-hydroxy-2-naphthoic acid (xinafoate) and the like. Particularly preferred are citric, hydrobromic, hydrochloric, maleic, phosphoric, sulfuric, xinafoate and tartaric acids.

It will be understood that, unless otherwise specified, references to the compound of Formula I subsets thereof, embodiments thereof, as well as specific compounds are meant to also include the pharmaceutically acceptable salts and stereoisomers thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the schemes and examples herein using appropriate isotopically-enriched reagents and/or intermediates.

Utilities

Compound of Formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of Formula I. In one embodiment such diseases include asthma and rheumatoid arthritis.

Another aspect of the present invention provides for the use of a compound of Formula I in the manufacture of a medicament for the treatment or prevention of a JAK-mediated disease or disorder.

One aspect of the invention is the use of a compound of Formula I or a pharmaceutically acceptable salt or a stereoisomer thereof in the manufacture of a medicament for the treatment of a disease or a disorder ameliorated by inhibition of Janus kinases JAK1 and JAK2.

Another aspect of the invention is the use of a compound of Formula I or a pharmaceutically acceptable salt or a stereoisomer thereof and a second active agent in the manufacture of a medicament for the treatment of a disease or a disorder ameliorated by inhibition of Janus kinases JAK1 and JAK2.

Dose Ranges

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g, of active agent compounded with an appropriate and convenient amount of carrier material which may vary from about 5 to about 99.95 percent of the total composition. In some cases, the dosage unit forms may contain from about 0.05 to about 3 g of active ingredient. Dosage unit forms will generally contain between from about 0.1 mg to about 0.4 g of an active ingredient, typically 0.1 mg, 0.2 mg, 0.3 mg, 0.4 mg, 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of Formula I with a pharmaceutically acceptable carrier. For the treatment of any of the prostanoid mediated diseases, compounds of Formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of Formula I may be co-administered with other therapeutic agents. Thus in another aspect the present invention provides pharmaceutical compositions for treating JAK mediated diseases comprising a therapeutically effective amount of a compound of Formula I and one or more other therapeutic agents. In particular, for the treatment of the inflammatory diseases rheumatoid arthritis, psoriasis, inflammatory bowel disease, COPD, asthma and allergic rhinitis a compound of Formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

SCHEMES AND EXAMPLES

The abbreviations used herein have the following tabulated meanings. Abbreviations not tabulated below have their meanings as commonly used unless specifically stated otherwise.

| | |
|---|---|
| ACN, MeCN | acetonitrile |
| AIBN | azobisisobutyronitrile |
| BnBr | benzyl bromide |
| Boc | tert-butyloxycarbonyl |
| Boc$_2$O | Boc anhydride |
| t-Bu XPhos | 2-di tert-butylphosphino-2',4',6'-triisopropylbiphenyl |
| n-BuOH | n-butanol |
| Chiral SFC | chiral super critical fluid chromatography |
| Cp$_2$ZrClH | zirconocene chloride hydride (Schwartz's reagent) |
| Cp | cyclopentadienyl |
| CO$_2$ | carbon dioxide |
| Cs$_2$CO$_3$ | cesium carbonate |
| Dba | dibenzylideneacetone |
| DBU | 1,8-diazabicyclo[5.4.0]undec-7-ene |
| DCM | dichloromethane |
| DEA | diethylamine |
| DIPEA, DIEA | N,N-diisopropylethylamine |
| DIBAL-H | diisobutylaluminium hydride |
| DMAP | dimethylamino pyridine |
| DMEA | dimethylethylamine |
| DMF | N,N-dimethylformamide |
| DMSO | dimethyl sulfoxide |
| EDC | 3-(ethyliminomethyleneamino)-N,N-dimethyl-propan-1-amine |
| EtOAc, EA | ethyl acetate |
| EtOH | ethanol |
| ESI | electro spray ionization |
| HATU | O-(7-aza-1H-benzotriazol-1-yl)-N,N,N',N'-tetramethyluronium hexafluorophosphate |
| HCl | hydrogen chloride |

-continued

| | |
|---|---|
| HPLC | high pressure liquid chromatography |
| LDA | lithium diisopropylamide |
| LR | low resolution |
| LCMS | liquid chromatrography mass spectrometry |
| LRMS | low resolution mass spectrometry |
| MeOH | methanol |
| Me$_4$-t-Bu-X-Phos | di-tert-butyl[3,4,5,6-tetramethyl-2',4',6'-tri(propan-2-yl)biphenyl-2-yl]phosphane |
| MPLC | medium pressure liquid chromatography |
| NaH | sodium hydride |
| Na$_2$SO$_4$ | sodium sulfate |
| NaBH$_4$ | sodium borohydride |
| NaHCO$_3$ | sodium bicarbonate |
| NBS | N-bromo succinamide |
| NMR | nuclear magnetic resonance |
| NPA | N-propyl amine |
| Pd$_2$(dba)$_3$ | tris(dibenzylideneacetone)dipalladium(0) |
| pH | $-\log[H^+]$ |
| PyBOP | (7-azabenzotriazol-1-yloxy)tripyrrolidinophosphonium hexafluorophosphate |
| SFC | Supercritical fluid chromatography |
| t-BuOH | tert-butanol |
| t-Bu Xphos | 2-di-tert-butylphosphino-2',4',6'-triisopropylbiphenyl |
| TEA | triethylamine |
| TFA | trifluoroacetic acid |
| THF | tetrahydrofuran |
| Tr | retention time |
| X-Phos | 2-dicyclohexylphosphino-2',4',6'-triisopropylbiphenyl |
| NMR | nuclear magnetic resonance |
| TLC | thin layer chromatography |
| MsCl | methanesulfonyl chloride |
| CF$_3$TMS | (trifluoromethyl)trimethylsilane |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted.

Ambient temperature is 15-25° C.

Most compounds were purified by reverse-phase preparative HPLC, MPLC on silica gel, SFC, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

Method 1

General procedures to prepare intermediates of the instant invention are described in Scheme 1. Using an appropriate base, such as DBU, in a suitable solvent, such as MeCN, EtOH, or n-BuOH, at a temperature at or around 25° C., pyrazolopyridone I-1 can undergo conjugate addition to optionally substituted acrylonitriles such as I-2 to yield alkylated pyrazolopyridones II, an intermediate in the synthesis of examples of the instant invention. Buchwald-Hartwig coupling with an appropriate aryl or heteroaryl halide (A-X, X=Cl, Br, I), afforded the protected pyridone III. This coupling could be carried out using an appropriate catalytic palladium-ligand system, such as $Pd_2(dba)_3$ or $Pd_2(dba)_3 \cdot CHCl_3$, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane ($Me_4$ $^tBu$-XPhos), or 2-dicyclohexylphosphino-2',4',6'-triisopropylbiphenyl (XPhos). Typically, this cross coupling is carried out using either 2-propanol or t-amyl alcohol solvents, employing either KOAc or $K_3PO_4$ base at between 70-80° C. Reduction of the nitrile to aldehyde IV could then be carried out with DIBAL-H, at or between −78° C. and 0° C. in a suitable solvent such as DCM. Further reduction of the aldehyde could be accomplished via a two step process via dithiane formation using $HSCH_2CH_2SH$ in the presence of acid, followed by reduction with Raney Ni to afford the ethyl substituted piperidine V.

SCHEME 1

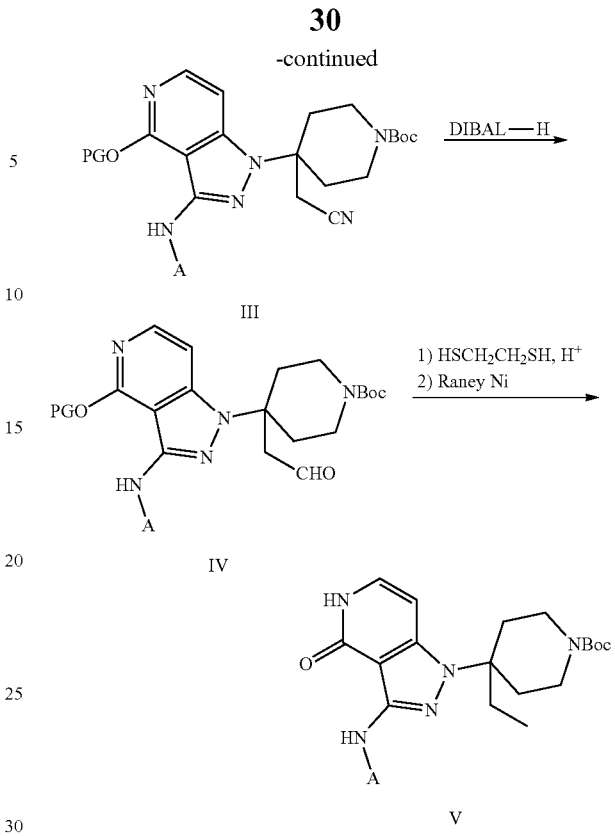

Method 2

General procedures to prepare intermediates of the instant invention are described in Scheme 2. Using an appropriate base, such as DBU, in a suitable solvent, such as MeCN, EtOH, or n-BuOH, at a temperature at or around 25° C., pyrazolopyridone I-1 can undergo conjugate addition to optionally substituted acrylonitriles such as I-2 to yield alkylated pyrazolopyridones II, an intermediate in the synthesis of examples of the instant invention. Double protection using a suitable protecting group such as Boc, followed by reduction of VI with bis(cyclopentadienyl)zirconium chloride hydride affords aldehyde VII. Further reduction to the alcohol VIII with a suitable reducing agent such as $NaBH_4$, followed by conversion of the alcohol VIII to the mesylate IX could then be accomplished with mesyl chloride. Alternatively, other suitable leaving groups such as tosylate could also be utilized. Hydride displacement using lithium triethylborate furnishes the desired ethyl piperidine X. Removal of the protecting groups could then be carried out all at once using a suitable acid, such as HCl, in a suitable solvent, such as EtOAc. Reinstallation of the piperidinyl Boc group to afford XI could then be accomplished using a suitable reagent such as $Boc_2O$. Buchwald-Hartwig coupling with an appropriate aryl or heteroaryl halide (A-X, X=Cl, Br, I) is then carried out to afford the compounds of the instant invention V. This coupling could be carried out using an appropriate catalytic palladium-ligand system, such as $Pd_2(dba)_3$ or $Pd_2(dba)_3 \cdot CHCl_3$, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane ($Me_4$ $^tBu$-XPhos), or 2-dicyclohexylphosphino-2',4',6'-triisopropylbiphenyl (XPhos). Typically, this cross coupling is carried out using either 2-propanol or t-amyl alcohol solvents, employing either KOAc or $K_3PO_4$ base at between 70-80° C.

SCHEME 2

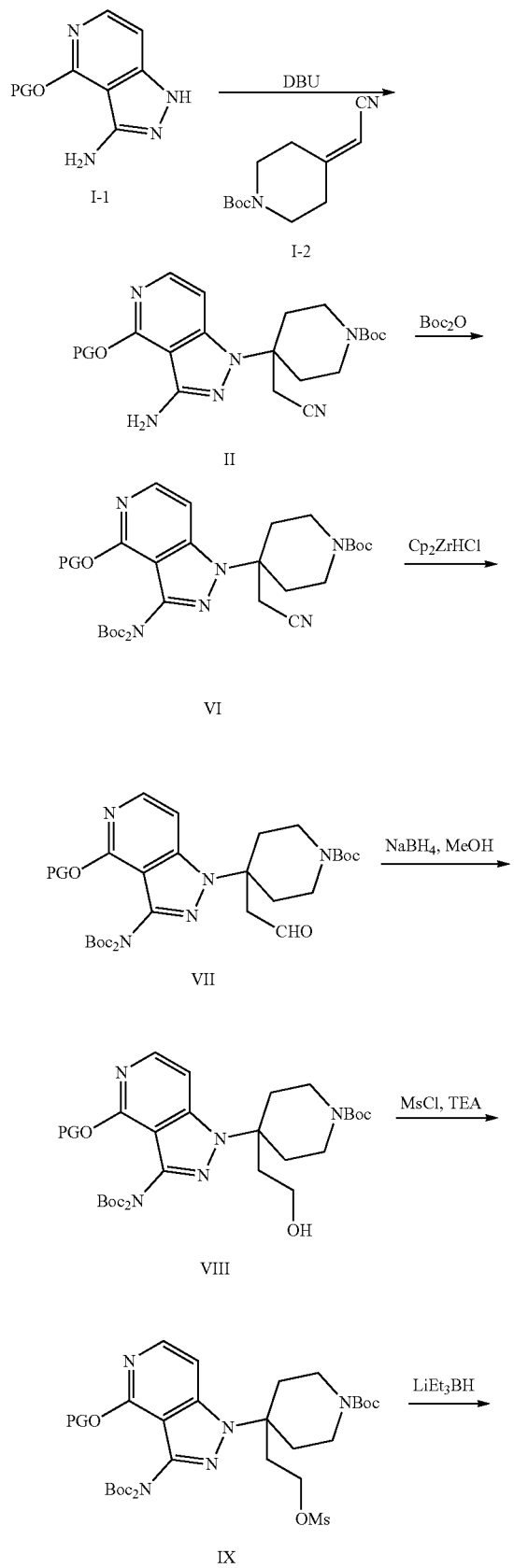

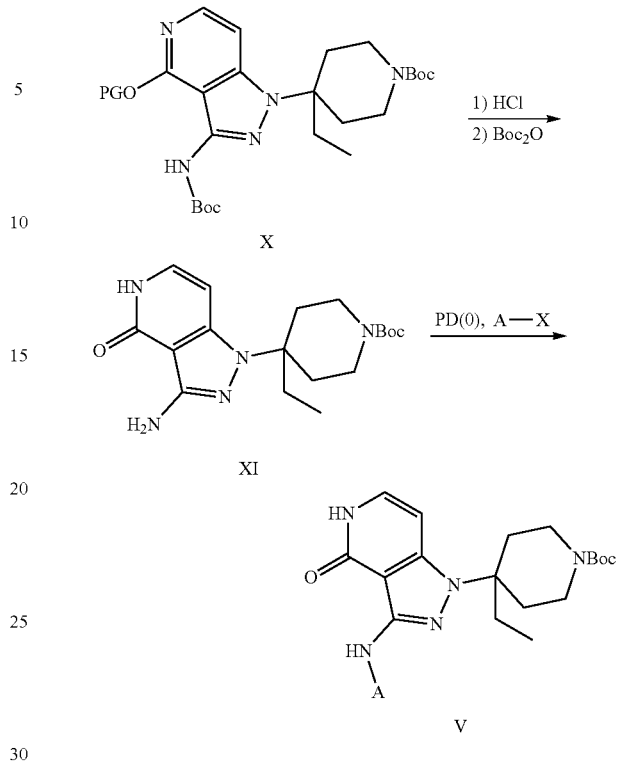

Method 3

General procedures to prepare examples of the instant invention are described in Scheme 3. In the case that the pyrazolopyrimidines V contain a pendant carboxylic acid group on the aryl or heteroaryl substituent "A", further functionalization could be achieved using a suitable amine, in the presence of a suitable coupling reagent such as HATU or EDC to afford the desired amide derivatives XII.

SCHEME 3

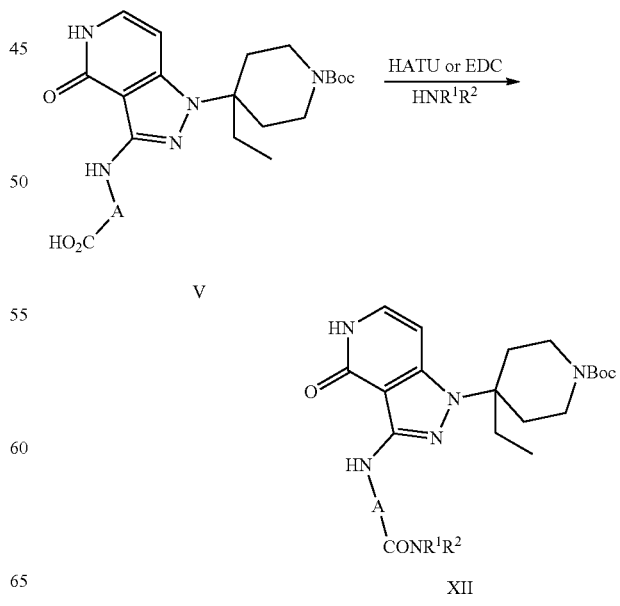

Intermediates

The following experimental procedures detail the preparation of chemical materials used in the synthesis of examples of the instant invention. The exemplified procedures are for illustrative purposes only, and are not intended to limit the scope of the instant invention in any way.

Intermediate 1

4-(benzyloxy)-1H-pyrazolo[4,3-c]pyridin-3-amine

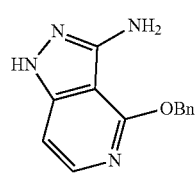

I-1

Step 1: 2-(benzyloxy)-4-methoxynicotinonitrile

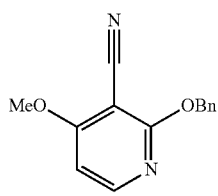 [SMILES: COc1ccnc(OCc2ccccc2)c1C#N]

To a solution of 2-hydroxy-4-methoxynicotinonitrile (60 g, 0.4 mol) in toluene (0.60 L) was added Ag$_2$CO$_3$ (0.14 kg, 0.51 mol) and BnBr (87 g, 0.51 mol) at room temperature. The mixture was stirred at 50° C. for 3 hours. The mixture was filtered and the cake washed with DCM. The filtrate was concentrated in vacuo and petroleum ether (100 mL) was added to the residue and the solid was filtered to give 2-(benzyloxy)-4-methoxynicotinonitrile as a solid. LRMS (ESI) calc'd for C$_{14}$H$_{13}$N$_2$O$_2$ [M+H]$^+$: 241, found 241. $^1$H NMR (600 MHz CDCl$_3$): δ 8.21 (d, J=6.6 Hz, 1H), 7.48 (d, J=7.8 Hz, 2H), 7.38 (m, 2H), 7.32 (m, 1H), 6.58 (d, J=6.0 Hz, 1H), 5.51 (s, 2H), 3.99 (s, 3H).

Step 2: 4-(benzyloxy)-1H-pyrazolo[4,3-c]pyridin-3-amine (I-1)

A suspension of 2-(benzyloxy)-4-methoxynicotinonitrile (100 g, 410 mmol) in hydrazine hydrate (0.20 kg, 4.1 mol) and n-BuOH (600 mL) was heated to reflux overnight. The mixture was concentrated in vacuo and purified by silica chromatography, eluting with 25% ethyl acetate in hexanes. Concentration of the desired fraction in vacuo afforded compound I-1. $^1$H NMR (400 MHz CDCl$_3$): δ 9.97 (s, 1H), 7.75 (d, J=6.4 Hz, 1H), 7.40 (d, J=7.2 Hz, 2H), 7.24-7.33 (m, 3H), 6.69 (d, J=6.4 Hz, 1H), 5.46 (s, 2H), 4.50 (s, 2H).

Intermediate 2 tert-butyl 4-(cyanomethylidene)piperidine-1-carboxylate

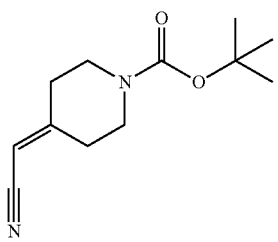

I-2

To a cooled, 0° C. solution of potassium tert-butoxide (263 mL, 263 mmol, 1.0 M in THF) and THF (200 mL), was slowly added diethyl (cyanomethyl)phosphonate (43.7 mL, 276 mmol). The reaction mixture was maintained at 0° C. for 10 minutes, then warmed to ambient temperature and stirred for 1 hour. The mixture was cooled to 0° C. and treated with the dropwise addition of tert-butyl 4-oxopiperidine-1-carboxylate (50.0 g, 251 mmol) in THF (150 mL) over 30 minutes. After addition, the mixture was maintained at 0° C. for 20 minutes, then warmed to ambient temperature and stirred for 18 hours. The reaction mixture was then diluted with water (800 mL) and extracted with EtOAc (×2). The combined organic extracts were washed with water, brine, dried over anhydrous Na$_2$SO$_4$, filtered, and concentrated in vacuo to afford the title compound as a solid, I-2. $^1$H NMR (600 MHz, CDCl$_3$): δ 5.19 (s, 1H), 3.48-3.53 (m, 4H), 2.56 (t, J=5.4 Hz, 2H), 2.33 (t, J=5.4 Hz, 2H), 1.47 (s, 9H).

Intermediate 3 tert-butyl 4-(3-amino-4-oxo-4,5-dihydro-1H-pyrazolo[4,3-c]pyridin-1-yl)-4-ethylpiperidine-1-carboxylate

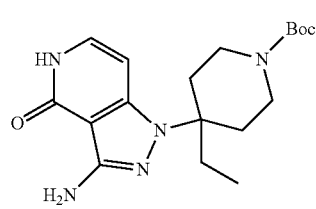

I-3

Step 1: tert-butyl 4-(3-amino-4-(benzyloxy)-1H-pyrazolo[4,3-c]pyridin-1-yl)-4-(cyanomethyl)piperidine-1-carboxylate

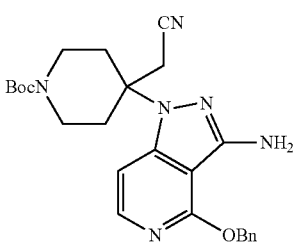 [SMILES: CC(C)(C)OC(=O)N1CCC(CC#N)(n2nc(N)c3c(OCc4ccccc4)nccc32)CC1]

To a solution of 4-(benzyloxy)-1H-pyrazolo[4,3-c]pyridin-3-amine (155 g, 645 mmol) in CH₃CN (2.50 L), was added (batchwise) tert-butyl 4-(cyanomethylidene)piperidine-1-carboxylate (286 g, 1.29 mol) followed by dropwise addition of DBU (99.0 g, 650 mmol) at 20° C. over 20 minutes. The resulting solution was stirred for 3 days at 20° C., concentrated in vacuo at 40-45° C., and then purified by silica chromatography, eluting with 0-50% ethyl acetate/hexanes. Concentration of the desired fraction in vacuo afforded the title compound. LRMS (ESI) calc'd for $C_{25}H_{31}N_6O_3$ [M+H]⁺: 463, found 463. ¹H NMR (300 MHz, CDCl₃): δ 7.82 (d, 1H), 7.34-7.50 (m, 5H), 6.84 (d, 1H), 5.54 (s, 2H), 4.51 (br s, 2H), 3.94-3.97 (d, 2H), 3.05 (br s, 2H), 2.85-2.90 (m, 2H), 2.79 (s, 2H), 1.92-2.04 (m, 2H), 1.45 (s, 9H).

Step 2: tert-butyl 4-{4-(benzyloxy)-3-[bis(tert-butoxycarbonyl)amino]-1H-pyrazolo[4,3-c]pyridin-1-yl}-4-(cyanomethyl)piperidine-1-carboxylate

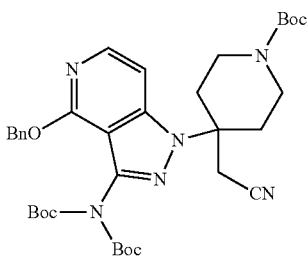

To tert-butyl 4-(3-amino-4-(benzyloxy)-1H-pyrazolo[4,3-c]pyridin-1-yl)-4-(cyanomethyl)piperidine-1-carboxylate (20.0 g, 43.2 mmol), was added DMAP (0.528 g, 4.32 mmol), TEA (18.1 mL, 130 mmol), DMF (200 mL), and Boc₂O (20.1 mL, 86.0 mmol) at room temperature. The reaction was stirred at room temperature for 16 hours, and then quenched with water (400 mL) and extracted with dichloromethane (×3). The combined organic layers were washed with water, brine, dried over anhydrous sodium sulfate, filtered and concentrated in vacuo. The crude residue was purified by silica chromatography, eluting with 10% ethyl acetate/hexanes to afford the title compound as a solid. LRMS (ESI) calc'd for $C_{35}H_{47}N_6O_7$ [M+H]⁺: 663, found 663.

Step 3: tert-butyl 4-{4-(benzyloxy)-3-[bis(tert-butoxycarbonyl)amino]-1H-pyrazolo[4,3-c]pyridin-1-yl}-4-(2-oxoethyl)piperidine-1-carboxylate

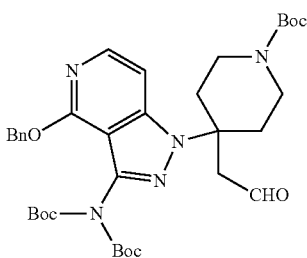 [SMILES: CC(C)(C)OC(=O)N1CCC(CC=O)(n2nc(N(C(=O)OC(C)(C)C)C(=O)OC(C)(C)C)c3c(OCc4ccccc4)nccc32)CC1]

Bis(cyclopentadienyl)zirconium chloride hydride (3.11 g, 12.1 mmol) was added in portions to a stirred, ambient temperature solution of tert-butyl 4-{4-(benzyloxy)-3-[bis(tert-butoxycarbonyl)amino]-1H-pyrazolo[4,3-c]pyridin-1-yl}-4-(cyanomethyl)piperidine-1-carboxylate (4.00 g, 6.04 mmol) in DCM (60 mL). The solution was stirred at ambient temperature for 10 minutes, then the reaction was quenched with water (400 mL) extracted with DCM (×3). The combined organic layers were washed with water, brine, dried over anhydrous sodium sulfate and filtered. The filtrate was concentrated in vacuo to give a residue that was subsequently purified by silica chromatography, eluting with 1% methanol/dichloromethane to afford a solid. LRMS (ESI) calc'd for $C_{35}H_{48}N_5O_8$ [M+H]⁺: 666, found 666.

Step 4: tert-butyl 4-{4-(benzyloxy)-3-[bis(tert-butoxycarbonyl)amino]-1H-pyrazolo[4,3-c]pyridin-1-yl}-4-(2-hydroxyethyl)piperidine-1-carboxylate

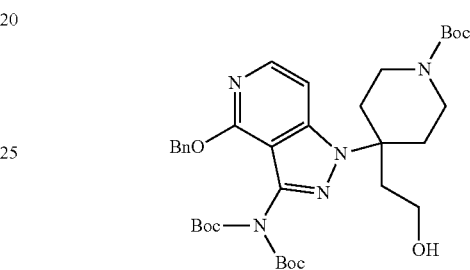

To a solution of tert-butyl 4-{4-(benzyloxy)-3-[bis(tert-butoxycarbonyl)amino]-1H-pyrazolo[4,3-c]pyridin-1-yl}-4-(2-oxoethyl)piperidine-1-carboxylate (9.50 g, 14.3 mmol) in MeOH (100 mL) at 0° C., was added NaBH₄ (1.62 g, 42.8 mmol). The mixture was stirred at 0° C. for 2 hours before being quenched by the addition of water (20 mL). The mixture was extracted with ethyl acetate (×2), and the combined organic fractions were washed with brine (×2), dried over Na₂SO₄, filtered and the solvent was evaporated in vacuo. The residue was purified by silica chromatography, eluting with 15-35% EtOAc/hexanes to give a solid. LRMS (ESI) calc'd for $C_{35}H_{50}N_5O_8$[M+H]⁺: 668, found 668. ¹H NMR (600 MHz, CDCl₃) δ 7.85 (d, J=6.4 Hz, 1H), 7.41 (d, J=7.4 Hz, 2H), 7.32 (t, J=7.4 Hz, 2H), 7.25 (apparent t, J=7.4 Hz, 1H), 7.02 (d, J=6.4 Hz, 1H), 5.50 (s, 2H), 3.88 (br, 2H), 3.39 (t, J=6.1 Hz, 2H), 2.94 (br, 2H), 2.84 (d, J=13.6 Hz, 2H), 2.09 (t, J=5.9 Hz, 2H), 1.87 (t, J=12.5 Hz, 2H), 1.70 (br s, 1H), 1.40 (s, 9H), 1.27 (s, 18H).

Step 5: tert-butyl 4-{4-(benzyloxy)-3-[bis(tert-butoxycarbonyl)amino]-1H-pyrazolo[4,3-c]pyridin-1-yl}-4-(2-methane sulfonyl ethyl)piperidine-1-carboxylate

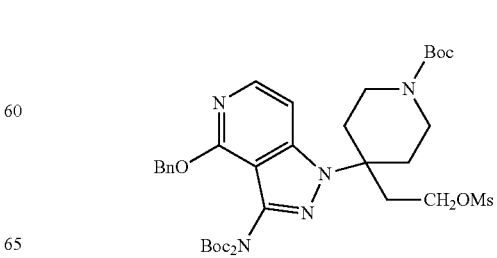

To a solution of tert-butyl 4-{4-(benzyloxy)-3-[bis(tert-butoxycarbonyl)amino]-1H-pyrazolo[4,3-c]pyridin-1-yl}-4-(2-hydroxyethyl)piperidine-1-carboxylate (7.00 g, 10.5 mmol) and TEA (3.18 g, 31.4 mmol) in DCM (80 mL), was added (dropwise) methanesulfonyl chloride (2.40 g, 21.0 mmol) at 0° C. The reaction was stirred at 25° C. for 2 hours, then quenched with water (60 mL) and extracted with dichloromethane (×3). The combined organic layers were washed with brine, dried over anhydrous sodium sulfate, filtered and the filtrate was concentrated in vacuo. The residue was purified by silica chromatography, eluting with 1:1 EtOAc/hexanes to afford a solid. LRMS (ESI) calc'd for $C_{36}H_{52}N_5O_{10}S$ [M+H]$^+$: 746, found 746.

Step 6: tert-butyl 4-(4-(benzyloxy)-3-((tert-butoxycarbonyl)amino)-1H-pyrazolo[4,3-c]pyridin-1-yl)-4-ethylpiperidine-1-carboxylate

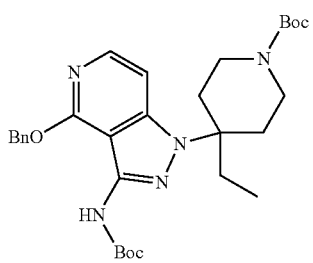 [SMILES: CCC1(n2nc(NC(=O)OC(C)(C)C)c3c(OCc4ccccc4)nccc32)CCN(C(=O)OC(C)(C)C)CC1]

To a solution of tert-butyl 4-{4-(benzyloxy)-3-[bis(tert-butoxycarbonyl)amino]-1H-pyrazolo[4,3-c]pyridin-1-yl}-4-(2-methane sulfonyl ethyl)piperidine-1-carboxylate (9.28 g, 12.4 mmol) in DMSO (10 mL) at 0° C., was added (portionwise) lithium triethylborohydride (124 mL, 124 mmol, 1.0 M in THF). The reaction was stirred at ambient temperature for 3 hours, then quenched by addition of water (120 mL) and extracted with ethyl acacate (×3). The combined organic layers were washed with water, brine, dried over anhydrous sodium sulfate and filtered. The filtrate was concentrated in vacuo to give a residue that was purified on silica chromatography, eluting with 20% EtOAc/hexanes to afford a solid. LRMS (ESI) calc'd for $C_{30}H_{42}N_5O_5$ [M+H]$^+$: 552, found 552.

Step 7: 3-amino-1-(4-ethylpiperidin-4-yl)-1H-pyrazolo[4,3-c]pyridin-4(5H)-one hydrochloride salt

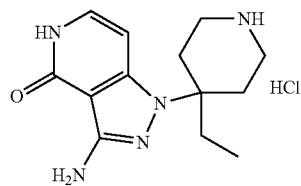 [SMILES: CCC1(n2nc(N)c3c(=O)[nH]ccc32)CCNCC1 ; Cl]

To tert-butyl 4-(4-(benzyloxy)-3-((tert-butoxycarbonyl)amino)-1H-pyrazolo[4,3-c]pyridin-1-yl)-4-ethylpiperidine-1-carboxylate (2.45 g, 4.44 mmol), was added hydrogen chloride solution (20 mL, 4.0 M in ethyl acetate, 40 mmol). The mixture was stirred for 5 hours at ambient temperature and then concentrated in vacuo to afford 3-amino-1-(4-ethylpiperidin-4-yl)-1H-pyrazolo[4,3-c]pyridin-4(5H)-one hydrochloride salt as a solid: LRMS (ESI) calc'd for $C_{13}H_{20}N_5O$ [M+H]$^+$: 262, found 262.

Step 8: tert-butyl 4-(3-amino-4-oxo-4,5-dihydro-1H-pyrazolo[4,3-c]pyridin-1-yl)-4-ethylpiperidine-1-carboxylate (I-3)

To a solution of 3-amino-1-(4-ethylpiperidin-4-yl)-1H-pyrazolo[4,3-c]pyridin-4(5H)-one hydrochloride salt (0.29 g, 0.97 mmol) in methanol (15 mL), was added sodium bicarbonate (0.49 g, 5.8 mmol) and di-tert-butyl dicarbonate (0.19 g, 1.07 mmol). The reaction was stirred for 1 hour at ambient temperature, then water (10 mL) was added and the mixture was extracted with ethyl acetate (×3). The combined organic layers were washed with brine (×2), dried over anhydrous sodium sulfate, filtered and concentrated in vacuo. The residue was purified by silica chromatography, eluting with 1:9 to 6:1 ethyl acetate in hexanes to afford tert-butyl 4-(3-amino-4-oxo-4,5-dihydro-1H-pyrazolo[4,3-c]pyridin-1-yl)-4-ethylpiperidine-1-carboxylate as a solid: LRMS (ESI) calc'd for $C_{18}H_{28}N_5O_3$ [M+H]$^+$: 362, found 362; $^1$H NMR (300 MHz, DMSO-d$_6$) δ 10.79 (br, 1H), 6.99-6.95 (m, 1H), 6.45-6.43 (m, 1H), 5.30 (s, 2H), 3.69-3.65 (m, 2H), 2.97-2.95 (m, 2H), 2.50 (m, 2H), 1.82-1.68 (m, 4H), 1.38 (s, 9H), 0.53 (s, 3H).

Intermediate 4

(R or S)-1-(4-bromophenyl)-2,2,2-trifluoroethanol

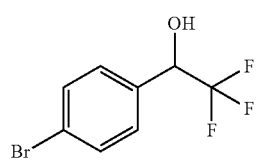

I-4A & I-4B

To a solution of 1-(4-bromophenyl)-2,2,2-trifluoroethanone (1.0 g, 3.95 mmol) in THF (10 mL) was added sodium borohydride (164 mg, 4.35 mmol). The mixture was stirred at room temperature for 2 hours, then quenched with water and concentrated in vacuo. The resulting residue was extracted with CH$_2$Cl$_2$ (×2), and the combined organic layers were washed with brine (×2), dried over sodium sulfate, filtered, and concentrated in vacuo to afford 1-(4-bromophenyl)-2,2,2-trifluoroethanol as a colorless liquid. $^1$H NMR (600 MHz, DMSO-d6): δ 7.58 (d, J=8.4 Hz, 2H), 7.41 (d, J=8.2 Hz, 2H), 6.90 (d, J=5.6 Hz, 1H), 5.16 (m, 1H). Separation of the enantiomers was achieved by SFC using a Chiral Technologies OJ-H, eluting with 5% isopropanol modifier in CO$_2$. Retention times=4.1 (enantiomer A—Intermediate 4A) & 5.1 (enantiomer B—Intermediate 4B) minutes.

Intermediates 5 and 6

(R or S) 2-(4-bromophenyl)-1,1,1-trifluoropropan-2-ol (I-5) (R or S) 1-bromo-4-(1,1,1-trifluoro-2-methoxypropan-2-yl)benzene (I-6)

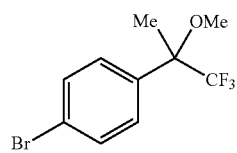

I-6A & I-6B

Step 1: (R or S) 2-(4-bromophenyl)-1,1,1-trifluoropropan-2-ol (I-5)

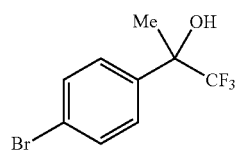

I-5A & I-5B

An oven dried round bottom flask with magnetic sir bar under an atmosphere of $N_2$ was charged with 1-(4-bromophenyl)-2,2,2-trifluoroethanone (2.0 g, 7.9 mmol) and THF (13 mL). The solution was cooled to 0° C., and methyl magnesium bromide (17 mL, 23.7 mmol, 1.4 M in diethyl ether) was added. The reaction mixture was warmed to room temperature over 1-2 hours, and then quenched by the addition of saturated aqueous $NH_4Cl$ (10 mL). The resulting mixture was extracted with $Et_2O$ (×3), and the combined organic layers were concentrated in vacuo to afford a residue that was purified by silica chromatography, eluting with hexanes/EtOAc gradient to yield racemic 2-(4-bromophenyl)-1,1,1-trifluoropropan-2-ol. LRMS (ESI) calc'd for $C_9H_9BrF_3O$ [M+H]$^+$: 269, found 269. $^1$H NMR (500 MHz, CDCl$_3$): δ 7.54 (d, J=8.3 Hz, 2H), 7.47 (d, J=8.3 Hz, 2H), 2.44 (s, 1H), 1.78 (s, 3H). Resolution of enantiomers was achieved by SFC purification using a Chiral Technology AZ-H with 5% MeOH in CO$_2$. Tr=2.6 minutes (Intermediate I-5A) & 3.2 minutes (Intermediate I-5B).

Step 2: (R or S) 1-bromo-4-(1,1,1-trifluoro-2-methoxypropan-2-yl)benzene (I-6)

An oven dried round bottom flask with magnetic sir bar under an atmosphere of $N_2$ was charged with 2-(4-bromophenyl)-1,1,1,1-trifluoropropan-2-ol I-5A (300 mg, 1.10 mmol) and DMF (3.5 mL). The solution was cooled to 0° C., sodium hydride (67 mg, 1.7 mmol, 60% wt. in mineral oil) was added, and the reaction was stirred for 30 minutes. Iodomethane (0.21 mL, 3.3 mmol) was then added and the reaction mixture was warmed to room temperature over 1-2 hours, quenched by addition of saturated aqueous $NH_4Cl$ (10 mL), and extracted with $Et_2O$ (×3). The combined organic layers were concentrated in vacuo to afford a residue that was purified by silica chromatography, eluting with hexanes/EtOAc gradient, to yield I-6A. I-6B was prepared in an analogous manner to I-6A above, using I-5B. $^1$H NMR (500 MHz, CDCl$_3$): δ 7.54 (d, J=8.2 Hz, 2H), 7.38 (d, J=8.1 Hz, 2H), 3.23 (s, 3H), 1.76 (s, 3H).

Intermediate 7A and 7B (R or S)-1-((4-bromophenyl)sulfonyl)-2-methylpyrrolidine

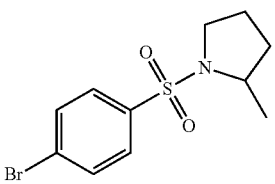

I-7A & I-7B

To a solution of 4-bromophenylsulfonyl chloride (0.300 g, 1.17 mmol) in CH$_2$Cl$_2$ (8.0 mL) was added 2-methylpyrrolidine (0.250 g, 2.94 mmol) and the reaction was stirred at room temperature under nitrogen overnight. The mixture was then quenched with saturated ammonium chloride solution and extracted with CH$_2$Cl$_2$ (×3). The organic layer was washed with water, dried over sodium sulfate, filtered and concentrated in vacuo and the residue was purified by silica chromatography, eluting with 0-60% EtOAc in hexanes. Concentration of the desired fractions afforded the title racemic compound I-7 that was separated into enantiomers by SFC using a Chiralpak AD-H column, eluting with 15% MeOH modifier in CO$_2$. Retention times=3.0 (enantiomer A—Intermediate 7A) & 4.4 (enantiomer B—Intermediate 7B) minutes. LRMS (ESI) calc'd for $C_{11}H_{15}BrNO_2S$ [M+H]$^+$: 304, found 304. $^1$H NMR (300 MHz, DMSO-d$_6$): δ 7.84 (d, J=8.7 Hz, 2H), 7.75 (d, J=8.7 Hz, 2H), 3.65-3.59 (m, 1H), 3.37-3.30 (m, 1H), 3.12-3.04 (m, 1H), 1.82-1.73 (m, 1H), 1.68-1.59 (m, 1H), 1.49-1.39 (m, 2H), 1.22 (d, J=6.3 Hz, 3H).

Intermediate 8

5-bromo-2-(tert-butyl)-2,3-dihydrobenzo[d]isothiazole-1,1-dioxide

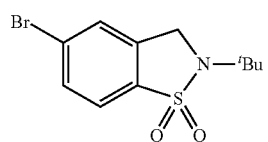

I-8

Step 1: 4-bromo-2-methylbenzene-1-sulfonyl chloride

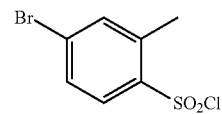

Chlorosulfonic acid (63 g, 0.54 mol) was added slowly to a cold solution (0° C.) of 1-bromo-3-methylbenzene (10 g, 58 mmol) in CHCl₃ (100 mL). The reaction was allowed to proceed with stirring for 2 hours at 0° C., then the reaction mixture was poured into ice water and extracted with EtOAc. The organic layer was then washed with brine, dried over NaSO₄, filtered and concentrated in vacuo to afford 4-bromo-2-methylbenzene-1-sulfonyl chloride as a solid. ¹H NMR (400 MHz, CDCl₃): δ 7.90 (d, J=8.4 Hz, 1H), 7.59-7.53 (m, 2H), 2.75 (s, 3H).

Step 2:
4-bromo-N-(tert-butyl)-2-methylbenzenesulfonamide

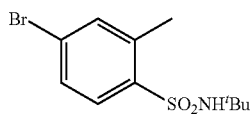

To a solution of 4-bromo-2-methylbenzene-1-sulfonyl chloride (2.0 g, 7.4 mmol) in CH₂Cl₂ (15 mL) was added a solution of 2-methylpropan-2-amine (0.65 g, 8.9 mmol) and triethylamine (0.90 g, 8.9 mmol) in CH₂Cl₂ (30 mL) at 0° C. The reaction mixture was stirred at 0° C. for 2 hours and then at room temperature for 16 hours. The mixture was washed with 0.1 M HCl, saturated aqueous NaHCO₃, dried over Na₂SO₄, filtered and concentrated in vacuo to afford 4-bromo-N-(tert-butyl)-2-methylbenzenesulfonamide as a solid. ¹H NMR (400 MHz, DMSO-d6): δ 7.78 (d, J=8.4 Hz, 1H), 7.63 (d, J=1.6 Hz, 1H), 7.59-7.56 (m, 2H), 2.57 (s, 3H), 1.09 (s, 9H).

Step 3: 5-bromo-2-(tert-butyl)benzo[d]isothiazol-3 (2H)-one-1,1-dioxide

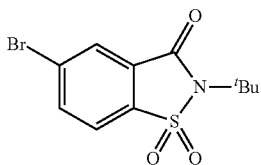 [SMILES: CC(C)(C)N1C(=O)c2cc(Br)ccc2S1(=O)=O]

A mixture of H₅IO₆ (5.9 g, 26 mmol) in acetonitrile (50 mL) was stirred at room temperature for 1 hour. Then CrO₃ (33 mg, 0.33 mmol) was added followed by acetic anhydride (2.67 g, 26 mmol). The resulting orange solution was cooled to 0° C., and 4-bromo-N-(tert-butyl)-2-methyl benzenesulfonamide (1.0 g, 3.3 mmol) was added. After stirring at 0° C. for 15 minutes, the reaction was allowed to warm to room temperature and was stirred for 16 hours. The solvent was removed in vacuo and the residue was extracted with EtOAc (×3). The combined organic layers were washed with saturated aqueous NaHCO₃, brine, dried over Na₂SO₄, filtered and concentrated in vacuo. The residue was purified by silica chromatography, eluting with 5% EtOAc in hexanes and the desired fractions were concentrated in vacuo to afford 5-bromo-2-(tert-butyl)benzo[d]isothiazol-3(2H)-one 1,1-dioxide as a solid. ¹H NMR (400 MHz, DMSO-d6): δ 8.82-8.14 (m, 3H), 1.66 (s, 9H).

Step 4: 5-bromo-2-(tert-butyl)-2,3-dihydrobenzo[d]isothiazole-1,1-dioxide (I-8)

To a solution of 5-bromo-2-(tert-butyl)benzo[d]isothiazol-3(2H)-one 1,1-dioxide (0.20 g, 0.63 mmol) in THF (4 mL) was added BH₃.Me₂S (240 mg, 3.16 mmol). The reaction mixture was refluxed for 16 hours. After being cooled to room temperature, the reaction was quenched with 2 M HCl and extracted with EtOAc (×2). The combined extracts were washed with brine, dried over Na₂SO₄, filtered, and the filtrate was concentrated in vacuo. The residue was purified by preparative TLC to afford compound 1-8. ¹H NMR (400 MHz, DMSO-d6): δ 7.83-7.56 (m, 3H), 4.55 (s, 2H), 1.46 (s, 9H).

Intermediate 9

5-bromo-2-(tetrahydro-2H-pyran-4-yl)-2,3-dihydrobenzo[d]isothiazole 1,1-dioxide

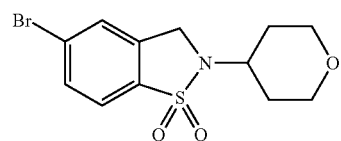

I-9

Step 1: 4-bromo-2-methyl-N-(tetrahydro-2H-pyran-4-yl)benzenesulfonamide

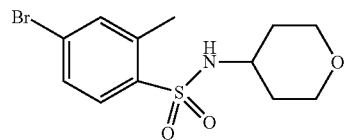 [SMILES: Cc1cc(Br)ccc1S(=O)(=O)NC1CCOCC1]

To a room temperature solution of tetrahydro-2H-pyran-4-amine (2.00 g, 19.7 mmol) in DCM (100 mL), was added triethylamine (7.97 g, 78.8 mmol) followed by 4-bromo-2-methylbenzene-1-sulfonyl chloride (5.00 g, 19.7 mmol). The reaction was stirred at ambient temperature for 2 hours and then quenched with water (100 mL), and the organic layer was separated, washed with brine, dried over anhydrous sodium sulfate, and filtered. The filtrate was concentrated in vacuo to afford a residue which was purified by silica chromatography, eluting with 50% EtOAc/hexanes to afford the title compound as a solid. LRMS (ESI) calc'd for C₁₂H₁₇BrNO₃S [M+H]⁺: 334, 336 (1:1), found 334, 336 (1:1); ¹H NMR (400 MHz, CDCl₃): δ 7.90 (d, J=4.8 Hz, 1H), 7.52-7.48 (m, 2H), 4.70 (d, J=8.0 Hz, 1H), 3.92-3.87 (m, 2H), 3.41-3.32 (m, 3H), 2.67 (s, 3H), 1.79-1.75 (m, 2H), 1.56-1.50 (m, 2H).

Step 2: 4-bromo-2-(bromomethyl)-N-(tetrahydro-2H-pyran-4-yl)benzenesulfonamide

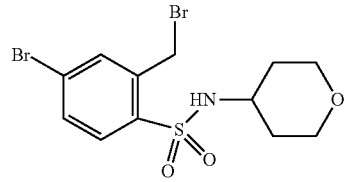 [SMILES: O=S(=O)(NC1CCOCC1)c1ccc(Br)cc1CBr]

To a solution of 4-bromo-2-methyl-N-(tetrahydro-2H-pyran-4-yl)benzenesulfonamide (5.00 g, 15.0 mmol) in CCl$_4$ (500 mL) was added NBS (5.33 g, 29.9 mmol) and benzoyl peroxide (0.725 g, 2.99 mmol). The resulting solution was stirred at 80° C. for 15 hours. The mixture was cooled, water (300 mL) was added, and the mixture was extracted with DCM (×3). The combined organic fractions were washed with brine (50 mL), dried over Na$_2$SO$_4$, filtered and the solvent was evaporated under reduced pressure. The residue was purified by column chromatography on silica gel with 5% EA/hexanes to give the title compound as a solid. LRMS (ESI) calc'd for C$_{12}$H$_{16}$Br$_2$NO$_3$S [M+H]$^+$: 414, 416 (1:1), found 414, 416 (1:1).

Step 3: 5-bromo-2-(tetrahydro-2H-pyran-4-yl)-2,3-dihydrobenzo[d]isothiazole 1,1-dioxide (I-9)

To a solution of 4-bromo-2-(bromomethyl)-N-(tetrahydro-2H-pyran-4-yl)benzenesulfonamide (2.3 g, 5.57 mmol) in acetonitrile (20 mL) and water (20 mL) was added NaHCO$_3$ (1.87 g, 22.3 mmol) and stirred at 80° C. for 18 hours. The reaction mixture was extracted with EtOAc (×3), and the organic layer was dried with Na$_2$SO$_4$, filtered and concentrated in vacuo. The residue was purified by a silica chromatography, eluting with 0-50% DCM/hexanes to afford the title compound as a solid. LRMS (ESI) calc'd for C$_{12}$H$_{15}$BrNO$_3$S [M+H]$^+$: 332, 334 (1:1), found 332, 334 (1:1); $^1$H NMR (400 MHz, CDCl$_3$): δ 7.72-7.69 (m, 2H), 7.62 (s, 1H), 4.41 (s, 2H). 4.11-4.08 (m, 2H), 3.97-3.89 (m, 1H), 3.56-3.53 (m, 2H), 2.08-1.92 (m, 4H).

Intermediate 10

4-bromo-2-ethylbenzoic acid

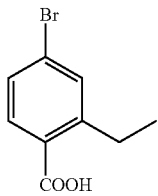

I-10

To a solution of 2,2,6,6-tetramethylpiperidine (5.70 mL, 33.7 mmol) in anhydrous THF (35 mL), was added n-butyllithium (13.4 mL, 33.7 mmol, 2.5 M in hexanes) dropwise at −78° C. The mixture was maintained at −78° C. for 1.5 hours and then a solution of 4-bromo-2-methylbenzoic acid (3.00 g, 14.0 mmol) in THF (30 mL) was added. The mixture was stirred at −78° C. for an additional 1.5 hours, then a solution of methyl iodide (1.70 mL, 27.3 mmol) in THF (5 mL) was added dropwise. The resulting mixture was warmed to ambient temperature and maintained at ambient temperature for 16 hours. The reaction was then quenched with water (5 mL), and the resulting solution was concentrated in vacuo. The residue was dissolved in aqueous sodium hydroxide (1 N) and extracted with EtOAc (×3). The separated aqueous layer was reacidified with HCl (1 N) and extracted with chloroform (×3), and the resulting organic layers were dried over Na$_2$SO$_4$, filtered, and concentrated in vacuo to afford the title acid as a solid. LRMS (ESI) calc'd for C$_9$H$_8$BrO$_2$ [M−H]$^-$: 227, 229 (1:1), found 227, 229 (1:1).

Intermediate 11

(2S and 2R)N-(1-(4-bromophenyl)-2,2,2-trifluoroethyl)-2-methylpropan-2-amine

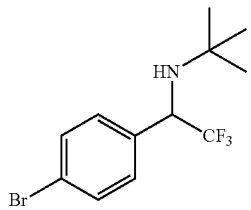

I-11

Step 1: 1-(4-bromophenyl)-2,2,2-trifluoroethyl trifluoromethanesulfonate

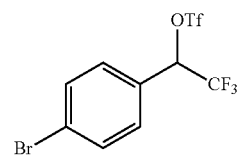

A solution of 1-(4-bromophenyl)-2,2,2-trifluoroethanol (I-4) (1.5 g, 5.9 mmol) and 2,6-lutidine (1.10 mL, 9.41 mmol) in DCE (12 mL) was cooled to −15° C. and triflic anhydride (8.82 mL, 8.82 mmol, 1.0 M in DCM) was added dropwise. The reaction was stirred between −15° C. and room temperature for 1 hours, then diluted with DCM and washed with water, 1N aqueous HCl, and brine. The combined organic layers were dried over Na$_2$SO$_4$, filtered, and the filtrate was concentrated in vacuo to give the title compound as a liquid. $^1$H NMR (500 MHz, CDCl$_3$): δ 7.64 (d, J=8.3 Hz, 2H), 7.37 (d, J=8.3 Hz, 2H), 5.85-5.74 (m, 1H).

Step 2: N-(1-(4-bromophenyl)-2,2,2-trifluoroethyl)-2-methylpropan-2-amine (I-11)

1-(4-Bromophenyl)-2,2,2-trifluoroethyl trifluoromethanesulfonate (7.59 g, 19.6 mmol) was dissolved in cyclohexane (70 mL) and 2-methylpropan-2-amine (6.23 mL, 58.8 mmol), DMAP (0.240 g, 1.96 mmol), and ground, dried potassium carbonate (5.42 g, 39.2 mmol) (dried over vacuum at 60° C. for one hour) was added. The reaction mixture was heated to 75° C. and stirred for 48 hours. The reaction mixture was diluted with DCM and washed with water. The combined organic layers were dried over Na$_2$SO$_4$, filtered, and the filtrate was concentrated in vacuo. The residue was purified by silica chromatography, eluting with 2-20% EtOAc in hexanes and the desired fractions were concentrated in vacuo to afford I-11 as a liquid. LRMS (ESI) calc'd for C$_{12}$H$_{16}$BrF$_3$N [M+H]$^+$: 310, found 310.

Intermediates I-12A and I-12B (R or S)-2-(4-bromophenyl)-2-(trifluoromethyl)piperidine

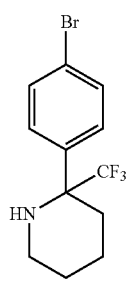

I-12A & I-12B

Step 1: 4-bromobenzoyl chloride

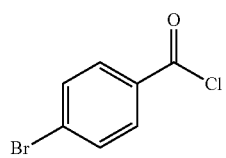

A solution of 4-bromobenzoic acid (10.0 g, 49.7 mmol) in sulfurous dichloride (59.2 g, 0.50 mol) was heated at 80° C. for 16 hours. The mixture was then concentrated in vacuo to afford the title compound which was carried onto the next step without further purification.

Step 2: tert-butyl 3-(4-bromobenzoyl)-2-oxopiperidine-1-carboxylate

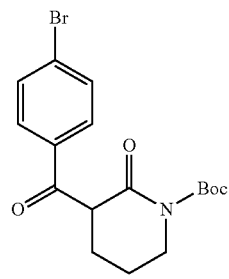 [SMILES: CC(C)(C)OC(=O)N1CCCC(C(=O)c2ccc(Br)cc2)C1=O]

Lithium bis(trimethylsilyl)amide (2.11 mL, 2.11 mmol, 1.0 M in THF) was added to a solution of tert-butyl 2-oxopiperidine-1-carboxylate (0.20 g, 1.0 mmol) in THF (2 mL) at −78° C. The resulting mixture was stirred for 10 minutes, then 4-bromobenzoyl chloride (0.22 g, 1.0 mmol) was added. The reaction was warmed to ambient temperature and stirred for 1 hour before being quenched with saturated aqueous ammonium chloride (20 mL). The quenched reaction was extracted with EtOAc (×3) and the combined organic layers were dried over anhydrous Na₂SO₄, filtered and concentrated in vacuo. The residue was purified on silica, eluting with 0-1% EtOAc in hexanes to afford the title compound. LRMS (ESI) calc'd for: $C_{17}H_{21}BrNO_4$ [M+H]⁺: 382, 384 (1:1), found 382, 384 (1:1).

Step 3: 6-(4-bromophenyl)-2,3,4,5-tetrahydropyridine

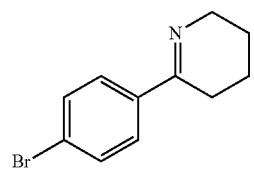 [SMILES: Brc1ccc(C2=NCCCC2)cc1]

tert-Butyl 3-(4-bromobenzoyl)-2-oxopiperidine-1-carboxylate (2.00 g, 5.23 mmol) was combined with HCl (8.0 M, 43.6 mL, 0.52 mol) at ambient temperature. The resulting solution was heated at 80° C. for 16 hours. The reaction was then poured into saturated aqueous Na₂CO₃ (50 mL) and extracted with EtOAc (×3). The combined organic layers were dried over Na₂SO₄, filtered and concentrated in vacuo. The residue was purified on silica, eluting with 0-1% EtOAc in hexanes to afford the title compound. LRMS (ESI) calc'd for: $C_{11}H_{13}BrN$ [M+H]⁺: 238, 240 (1:1), found 238, 240 (1:1); ¹H NMR (300 MHz, CDCl₃): δ 7.66-7.63 (m, 2H), 7.52-7.47 (m, 2H), 3.90 (m, 2H), 2.59 (m, 2H), 1.88-1.79 (m, 2H), 1.78-1.66 (m, 2H).

Step 4: (R or S)-2-(4-bromophenyl)-2-(trifluoromethyl)piperidine (I-12A & I-12B)

To a solution of 6-(4-bromophenyl)-2,3,4,5-tetrahydropyridine (1.0 g, 4.2 mmol) in acetonitrile (10 mL), was successively added trifluoromethanesulfonic acid (3.30 g, 22.0 mmol), potassium hydrogen fluoride (3.94 g, 50.4 mmol) and trimethyl(trifluoromethyl)silane (5.97 g, 42.0 mmol) at 0-4° C. The resulted mixture was stirred at ambient temperature for 48 hours. The reaction was then quenched with saturated aqueous NaHCO₃ (50 mL) followed by extraction with EtOAc (×3). The combined organic layers were dried over anhydrous Na₂SO₄, filtered and concentrated in vacuo. The residue was purified on silica, eluting with 0-1% DCM in hexanes to afford the racemic title compound. The title compounds were then separated by SFC using a Chiralpak IA column, eluting with 15% i-PrOH in CO₂ to afford Peak A (I-12A) (Tr=4.7 minutes, denoted as R) and Peak B (I-12B) (Tr=5.5 minutes, denoted as S). LRMS (ESI) calc'd for $C_{12}H_{14}BrF_3N$ [M+H]⁺: 308, 310 (1:1), found 308, 310 (1:1); ¹H NMR (300 MHz, CDCl₃): δ 7.66 (m, 2H), 7.59 (m, 2H), 3.16-3.03 (m, 1H), 2.73-2.63 (m, 1H), 2.50-2.42 (m, 1H), 2.25-1.93 (m, 1H), 1.75 (m, 1H), 1.67-1.53 (m, 3H), 1.33 (m, 1H).

Intermediates I-13A and I-13B (R or S)-2-(4-bromophenyl)-2-(trifluoromethyl)pyrrolidine

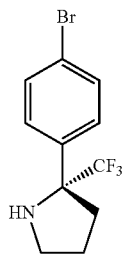

I-13A

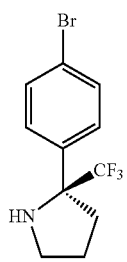

I-13B

Step 1: 3-(4-bromobenzoyl)-1-vinylpyrrolidin-2-one

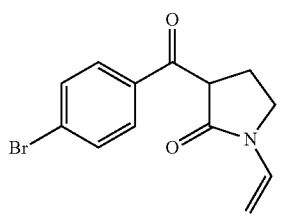 [SMILES: C=CN1CCC(C(=O)c2ccc(Br)cc2)C1=O]

Potassium tert-butoxide (6.26 g, 55.80 mmol) was added to a solution of 1-vinylpyrrolidin-2-one (6.20 g, 55.8 mmol) and methyl 4-bromobenzoate (10.00 g, 46.50 mmol) in THF (150 mL). The mixture was stirred at ambient temperature for an hour at which time water (200 mL) was added and the pH was adjusted to 7 with aqueous hydrochloric acid (1 M). The resulting mixture was extracted with EtOAc (×3). The combined organic layers were dried over anhydrous Na$_2$SO$_4$, filtered and concentrated in vacuo. The resulting residue was purified by silica chromatography, eluting with 0-20% EtOAc in hexanes to afford the title compound as a solid. LRMS (ESI) calc'd for C$_{13}$H$_{13}$BrNO$_2$ [M+H]$^+$: 294, 296 (1:1), found 294, 296 (1:1); $^1$H NMR (300 MHz, CDCl$_3$): δ 7.90 (d, J=6.6 Hz, 2H), 7.65 (d, J=6.6 Hz, 2H), 7.06-6.97 (m, 1H), 4.53 (m, 3H), 3.77-3.68 (m, 1H), 3.59 (m, 1H), 2.80-2.71 (m, 1H), 2.37-2.28 (m, 1H).

Step 2: 5-(4-bromophenyl)-3,4-dihydro-2H-pyrrole

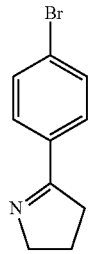 [SMILES: Brc1ccc(C2=NCCC2)cc1]

A suspension of 3-(4-bromobenzoyl)-1-vinylpyrrolidin-2-one (5.00 g, 17.0 mmol) in aqueous HCl (20 mL, 8 M) was heated at reflux for 16 hours. The mixture was cooled to ambient temperature and extracted with EtOAc (×3). The aqueous layer was basified to pH=13 with NaOH (15% aqueous solution) and then extracted with DCM (×5). The combined organic layers were dried over anhydrous Na$_2$SO$_4$, filtered and concentrated in vacuo. The resulting residue was purified by silica chromatography, eluting with 0-20% EtOAc/hexanes to afford the title compound as a solid. LRMS (ESI) calc'd for C$_{10}$H$_{11}$BrN [M+H]$^+$: 224, 226 (1:1), found 224, 226 (1:1); $^1$H NMR (300 MHz, CDCl$_3$): δ 7.74-7.69 (m, 2H), 7.54 (m, 2H), 4.06 (m, 2H), 2.96-2.88 (m, 2H), 2.10-2.00 (m, 2H).

Step 3: (S or R)-2-(4-bromophenyl)-2-(trifluoromethyl)pyrrolidine (I-13A & I-13B)

To an ice-cooled solution of 5-(4-bromophenyl)-3,4-dihydro-2H-pyrrole (0.80 g, 3.6 mmol) in dry acetonitrile (3 mL) was successively added trifluoromethanesulfonic acid (0.67 g, 4.5 mmol), potassium hydrogen fluoride (0.840 g, 10.7 mmol) and trimethyl(trifluoromethyl) silane (5.08 g, 35.7 mmol). The reaction solution was warmed to ambient temperature and stirred for 48 hours before being quenched with saturated aqueous NaHCO$_3$ until pH>7. The solution was extracted with EtOAc (×3) and the combined organic layers were dried over anhydrous Na$_2$SO$_4$, filtered and concentrated in vacuo. The residue was purified by silica chromatography, eluting with 0-20% DCM/hexanes to afford the title compound as an oil. LRMS (ESI) calc'd for C$_{11}$H$_{12}$BrF$_3$N [M+H]$^+$: 294, 296 (1:1), found 294, 296 (1:1); $^1$H NMR (300 MHz, CDCl$_3$): δ 7.49 (d, J=5.4 Hz, 2H), 7.42 (d, J=5.4 Hz, 2H), 3.29-3.21 (m, 1H), 3.16-3.08 (m, 1H), 2.60-2.51 (m, 1H), 2.25-2.16 (m, 1H), 2.08-1.94 (m, 1H), 1.89-1.75 (m, 1H). This racemic mixture was resolved by chiral HPLC using a Chiralpak AD-H column and methanol (with 0.2% DEA modifier) to Peak 1 (I-13A, retention time=4.4 minutes, denoted as R) and Peak 2 (I-13B, retention time=5.2 minutes, denoted as S).

Intermediates I-14A and I-14B (R or S)-2-(4-bromophenyl)-2-(trifluoromethyl)azepane

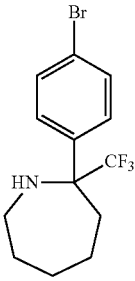

I-14A & I-14B

Step 1: tert-butyl 3-(4-bromobenzoyl)-2-oxoazepane-1-carboxylate

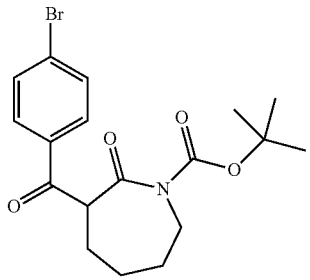 [SMILES: CC(C)(C)OC(=O)N1CCCCC(C(=O)c2ccc(Br)cc2)C1=O]

To a solution of tert-butyl 2-oxoazepane-1-carboxylate (27.0 g, 0.127 mol) in THF (60 mL) at −78° C., was added dropwise a solution of lithium bis(trimethylsilyl)amide (152 mL, 0.15 mol, 1 M in THF). The resulting solution was stirred for 10 minutes, then 4-bromobenzoyl chloride (30.6 g, 0.139 mol) was added to the mixture and the resulting mixture was warmed to ambient temperature and stirred for 1 hour before the addition of saturated aqueous ammonium chloride (100 mL). The solution was extracted with EtOAc (×3), and the combined organic fractions were dried over anhydrous $Na_2SO_4$, filtered, and concentrated in vacuo. The residue was purified by silica chromatography, eluting with 0-50% EtOAc/hexanes to afford the title compound as a solid. $^1$H NMR (300 MHz, CDCl$_3$): δ 7.75 (d, J=8.4 Hz, 2H), 7.58 (d, J=8.4 Hz, 2H), 4.46-4.42 (m, 1H), 4.38-4.30 (m, 1H), 3.55-3.47 (m, 1H), 2.33-2.28 (m, 1H), 2.07-1.93 (m, 3H), 1.65-1.52 (m, 2H), 1.48 (s, 9H).

Step 2: 6-amino-1-(4-bromophenyl)hexan-1-one

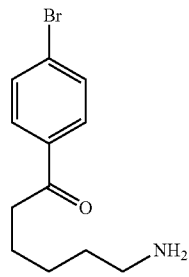 [SMILES: NCCCCCC(=O)c1ccc(Br)cc1]

A mixture of tert-butyl 3-(4-bromobenzoyl)-2-oxoazepane-1-carboxylate (10.0 g, 25.2 mmol) in aqueous hydrochloric acid (8 M, 210 mL, 1.68 mol) was stirred at 90° C. for 16 hours. The mixture was then poured into saturated sodium carbonate (500 mL), and extracted with EtOAc (×3). The combined organic fractions were dried over $Na_2SO_4$, filtered, and the filtrate was concentrated in vacuo. The residue was purified by silica chromatography, eluting with 0-100% EtOAc/hexanes to afford the title compound as a solid. LRMS (ESI) calc'd for $C_{12}H_{17}BrNO$ [M+H]$^+$: 270, 272 (1:1), found 270, 272 (1:1); $^1$H NMR (300 MHz, DMSO-d$_6$): δ 7.90 (d, J=8.4 Hz, 2H), 7.89-7.80 (br s, 2H), 7.75 (d, J=8.4 Hz, 2H), 3.05-2.94 (m, 2H), 2.79-2.73 (m, 2H), 1.80-1.52 (m, 4H), 1.40-1.24 (m, 2H).

Step 3: 7-(4-bromophenyl)-3,4,5,6-tetrahydro-2H-azepine

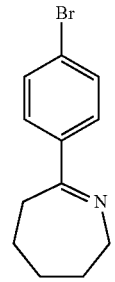

A solution of 6-amino-1-(4-bromophenyl)hexan-1-one (5.00 g, 18.5 mmol) and potassium hydroxide (5.19 g, 92.6 mmol) in methanol (50 mL) was stirred at ambient temperature for 16 hours. The mixture was then concentrated in vacuo, and the residue was purified by silica chromatography, eluting with 0-50% EtOAc/hexanes to afford the title compound as a solid. LRMS (ESI) calc'd for $C_{12}H_{15}BrN$ [M+H]$^+$: 252, 254 (1:1), found 252, 254 (1:1); $^1$H NMR (300 MHz, DMSO-d$_6$): δ 7.70 (d, J=8.4 Hz, 2H), 7.58 (d, J=8.4 Hz, 2H), 3.75 (t, J=4.8 Hz, 2H), 2.81 (t, J=5.4 Hz, 2H), 1.85-1.70 (m, 2H), 1.53-1.47 (m, 4H).

Step 4: (R or S)-2-(4-bromophenyl)-2-(trifluoromethyl)azepane and (S)-2-(4-bromophenyl)-2-(trifluoromethyl)azepane (I-14A & I-14B)

To a solution of 7-(4-bromophenyl)-3,4,5,6-tetrahydro-2H-azepine (2.10 g, 8.33 mmol) in dry acetonitrile (10 mL), was successively added trifluoromethanesulfonic acid (6.25 g, 41.6 mmol), potassium hydrogen fluoride (7.81 g, 0.100 mol) and trimethyl(trifluoromethyl) silane (11.8 g, 83.3 mmol) at 0° C. The mixture was then stirred at ambient temperature for 16 hours before addition of saturated aqueous sodium bicarbonate to adjust the pH to ~7. The mixture was extracted with EtOAc (×3), and the combined organic layers were dried over anhydrous $Na_2SO_4$, filtered, and concentrated in vacuo. The residue was purified by silica chromatography, eluting with 0-50% DCM/hexanes to afford racemic title compound as an oil. The racemic material was then separated by preparative chiral SFC using a Chiralpak AD-H column, eluting with 10% ethanol (with 0.2% diethyl amine) modifier in $CO_2$ to afford 3.98 (Enantiomer A—I-14A, denoted as R) & 4.68 (Enantiomer B—I-14B, denoted as S) minutes. LRMS (ESI) calc'd for $C_{13}H_{16}BrF_3N$ [M+H]$^+$: 322, 324 (1:1), found 322, 324 (1:1); $^1$H NMR (300 MHz, CDCl$_3$): δ 7.52 (s, 4H), 3.22-3.08 (m, 1H), 2.84-2.74 (m, 1H), 2.37-2.17 (m, 2H), 1.94-1.25 (m, 7H).

Intermediate 15-1

(4-bromo-2-methylphenyl)(4,4-difluoropiperidin-1-yl)methanone

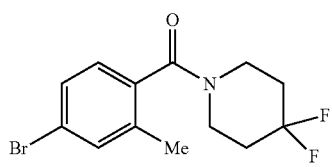

I-15-1

To a solution of 4-bromo-2-methylbenzoic acid (0.75 g, 3.5 mmol) in DMF (9 mL), was added HATU (2.6 g, 7.0 mmol), Hünig's base (2.4 mL, 14 mmol), and 4,4-difluoropiperidine (0.84 g, 7.0 mmol). The resulting reaction mixture was stirred for 16 hours, concentrated in vacuo, and the crude oil was purified by silica chromatography, eluting with a hexanes/EtOAc gradient to yield I-15-1. $^1$H NMR (500 MHz, CDCl$_3$): δ 7.42-7.37 (m, 2H), 7.05 (d, J=8.1 Hz, 1H), 4.02 (m, 1H), 3.82 (m, 1H), 3.36 (m, 2H), 2.30 (s, 3H), 2.11-2.07 (m, 2H), 1.88 (m, 2H).

Table 2 discloses Examples that were prepared in analogy to I-15-1.

Step 1: 4-bromo-2-methylbenzoyl chloride

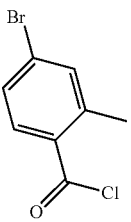

4-Bromo-2-methylbenzoic acid (1.40 g, 6.50 mmol) was dissolved in thionyl chloride (20 mL) and the mixture was stirred at 80° C. for 2 hours, then concentrated in vacuo to afford crude 4-bromo-2-methylbenzoyl chloride as a solid that was used as is without further purification.

TABLE 2

| Example | Structure | Compound Name | LRMS |
|---|---|---|---|
| I-15-2 | ![structure] | (4-bromo-2-methylphenyl)(morpholino)methanone | LRMS (ESI) Calc'd for C$_{12}$H$_{15}$BrNO$_2$ [M + H]$^+$: 286, found 286. |
| I-15-3 | ![structure] | (4-bromo-2-methylphenyl)(thiomorpholino)methanone | LRMS (ESI) Calc'd for C$_{12}$H$_{15}$BrNOS [M + H]$^+$: 302, found 302. |

Intermediate 16-1

8-oxa-3-azabicyclo[3.2.1]octan-3-yl(4-bromo-2-methylphenyl)methanone

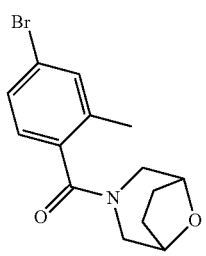 [SMILES: Cc1cc(Br)ccc1C(=O)N1CC2CCC(C1)O2]

Step 2: 8-oxa-3-azabicyclo[3.2.1]octan-3-yl(4-bromo-2-methylphenyl)methanone (I-16-1)

4-Bromo-2-methylbenzoyl chloride (1.24 g, 5.30 mmol) was added to a suspension of (1R,5S)-8-oxa-3-azabicyclo[3.2.1]octane (0.50 g, 4.4 mmol) and triethylamine (2.51 ml, 17.99 mmol) in DCM (10 mL) at ambient temperature. The reaction mixture was stirred at ambient temperature for 2 hours, then diluted with DCM (30 mL) and washed with brine (×2). The combined organic layers were concentrated in vacuo and purified by silica chromatography, eluting with 20% EtOAc/hexanes to afford the title compound as a solid. LRMS (ESI) calc'd for C$_{14}$H$_{17}$BrNO$_2$ [M+H]$^+$: 310, 312 (1:1) found 310, 312 (1:1); $^1$H NMR (300 MHz, CDCl$_3$): δ 7.41 (s, 1H), 7.36 (d, J=8.1 Hz, 1H), 7.08 (d, J=8.1 Hz, 1H), 4.76 (m, 1H), 3.85 (m, 1H), 3.72 (m, 1H), 3.55 (m, 3H), 2.34 (s, 3H), 2.15-1.86 (m, 4H).

Table 3 discloses intermediates that were prepared in an analogous manner to that of I-16-1 above.

TABLE 3

| Example | Structure | Compound Name | LRMS and/or ¹H NMR |
|---|---|---|---|
| I-16-2 | 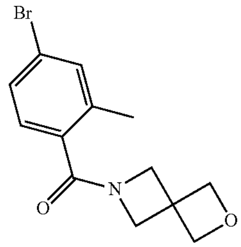 [SMILES: Cc1cc(Br)ccc1C(=O)N1CC2(COC2)C1] | 6-[(4-bromo-2-methylphenyl)carbonyl]-2-oxa-6-azaspiro[3,3]heptane | LRMS (ESI) calc'd for $C_{13}H_{15}BrNO_2$ [M + H]⁺: 296, 298 (1:1), found 296, 298 (1:1); ¹H NMR (400 MHz, CDCl₃): δ 7.42 (d, J = 1.2 Hz, 1H), 7.42-7.34 (m, 1H), 7.12 (d, J = 8.4 Hz, 1H), 4.87-4.77 (m, 4H), 4.34 (s, 2H), 4.09 (s, 2H), 2.39 (d, J = 7.6 Hz, 3H). |
| I-16-3 | 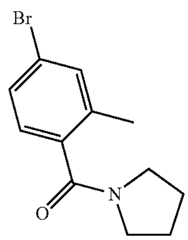 | (4-bromophenyl)(pyrrolidin-1-yl)methanone | LRMS (ESI) calc'd for $C_{12}H_{15}BrNO$ [M + H]⁺: 268, 270 (1:1), found 268, 270 (1:1); ¹H NMR (300 MHz, CDCl₃): δ 7.54 (d, J = 8.7 Hz, 2H), 7.40 (d, J = 8.7 Hz, 2H), 3.79-3.52 (m, 4H), 2.04-1.92 (m, 4H). |
| I-16-4 | 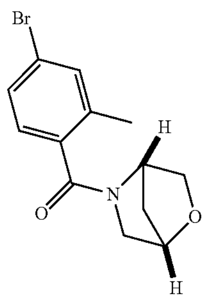 [SMILES: Cc1cc(Br)ccc1C(=O)N1C[C@@H]2C[C@H]1CO2] | (1S,4S)-5-oxa-2-azabicyclo[2.2.1]heptan-2-yl(4-bromo-2-methylphenyl)methanone | LRMS (ESI) calc'd for $C_{13}H_{15}BrNO_2$ [M + H]⁺: 296, 298 (1:1) found 296, 298 (1:1); ¹H NMR (300 MHz, DMSO-d₆): δ 7.53 (m, 1H), 7.44 (m, 1H), 7.25-7.16 (m, 1H), 4.89-4.50 (m, 1H), 3.96-3.30 (m, 6H), 2.20 (d, J = 7.5 Hz, 3H), 1.90 (m, 1H). |
| I-16-5 | 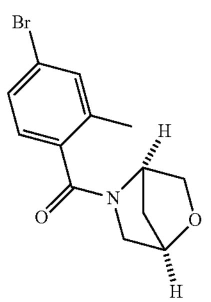 [SMILES: Cc1cc(Br)ccc1C(=O)N1C[C@H]2C[C@@H]1CO2] | (1R,4R)-5-oxa-2-azabicyclo[2.2.1]heptan-2-yl(4-bromo-2-methylphenyl)methanone | LRMS (ESI) calc'd for $C_{13}H_{15}BrNO_2$ [M + H]⁺: 296, 298 (1:1) found 296, 298 (1:1); ¹H NMR (300 MHz, DMSO-d₆): δ 7.53 (m, 1H), 7.44 (m, 1H), 7.25-7.16 (m, 1H), 4.89-4.50 (m, 1H), 3.96-3.30 (m, 6H), 2.20 (d, J = 7.5 Hz, 3H), 1.90 (m, 1H). |
| I-16-6 | 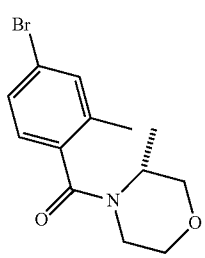 [SMILES: Cc1cc(Br)ccc1C(=O)N1CCOC[C@H]1C] | (R)-(4-bromo-2-methylphenyl)(3-methylmorpholino)methanone | LRMS (ESI) calc'd for $C_{13}H_{17}BrNO_2$ [M + H]⁺: 298, 300 (1:1), found 298, 300 (1:1); ¹H NMR (300 MHz, CDCl₃): δ 7.38 (m, 2H), 7.05 (m, 1H), 4.79-4.43 (m, 1H), 4.02-3.68 (m, 2H), 3.64-3.36 (m, 3H), 3.27-3.06 (m, 1H), 2.33-2.24 (m, 3H), 1.42-1.25 (m, 3H). |
| I-16-7 | 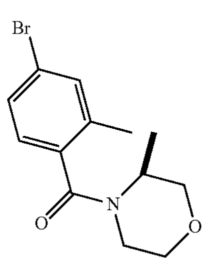 [SMILES: Cc1cc(Br)ccc1C(=O)N1CCOC[C@@H]1C] | (S)-(4-bromo-2-methylphenyl)(3-methylmorpholino)methanone (from commercial (S)amine) | LRMS (ESI) calc'd for $C_{13}H_{17}BrNO_2$ [M + H]⁺: 298, 300 (1:1), found 298, 300 (1:1); ¹H NMR (300 MHz, CDCl₃): δ 7.38 (m, 2H), 7.05 (m, 1H), 4.79-4.43 (m, 1H), 4.02-3.68 (m, 2H), 3.64-3.36 (m, 3H), 3.27-3.06 (m, 1H), 2.33-2.24 (m, 3H), 1.42-1.25 (m, 3H). |

TABLE 3-continued

| Example | Structure | Compound Name | LRMS and/or ¹H NMR |
|---|---|---|---|
| I-16-8 | 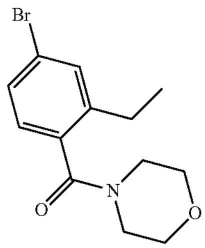 [SMILES: CCc1cc(Br)ccc1C(=O)N1CCOCC1] | (4-bromo-2-ethylphenyl)(morpholino)methanone | LRMS (ESI) calc'd for $C_{13}H_{17}BrNO_2$ [M + H]⁺: 298, 300 (1:1), found 298, 300 (1:1); ¹H NMR (300 MHz, DMSO-d₆): δ 7.54 (d, J = 1.8 Hz, 1H), 7.45 (dd, J = 8.1, 2.1 Hz, 1H), 7.15 (d, J = 8.1 Hz, 1H), 3.64 (m, 4H), 3.48 (m, 2H), 3.13-2.11 (m, 2H), 2.54 (m, 2H), 1.14 (t, J = 7.8 Hz, 3H). |
| I-16-9 | 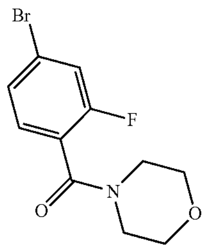 [SMILES: O=C(c1ccc(Br)cc1F)N1CCOCC1] | (4-bromo-2-fluorophenyl)(morpholino)methanone | LRMS (ESI) calc'd for $C_{11}H_{12}BrFNO_2$ [M + H]⁺: 288, 290 (1:1), found 288, 290 (1:1); ¹H NMR (400 MHz, CDCl₃): δ 7.40 (d, J = 8.0 Hz, 1H), 7.30 (m, 2H), 3.81 (m, 4H), 3.63 (m, 2H), 3.35 (m, 2H). |
| I-16-10 | 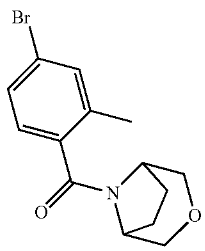 [SMILES: Cc1cc(Br)ccc1C(=O)N1C2CCC1COC2] | 3-oxa-8-azabicyclo[3.2.1]octan-8-yl(4-bromo-2-methylphenyl)methanone | LRMS (ESI) calc'd for $C_{14}H_{17}BrNO_2$ [M + H]⁺: 310, 312 (1:1), found 310, 312 (1:1); ¹H NMR (300 MHz, CDCl₃): δ 7.42 (s, 1H), 7.36 (d, J = 8.1 Hz, 1H), 7.09 (d, J = 8.1 Hz, 1H), 4.76-4.31 (m, 2H), 4.22 (m, 1H), 3.38 (m, 1H), 3.15-2.91 (m, 2H), 2.37 (s, 3H), 2.07-1.88 (m, 4H). |
| I-16-11 | 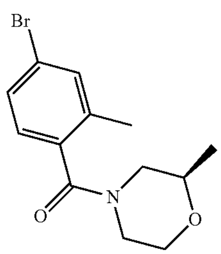 [SMILES: Cc1cc(Br)ccc1C(=O)N1CCO[C@H](C)C1] | (R)-(4-bromo-2-methylphenyl)(2-methylmorpholino)methanone | LRMS (ESI) calc'd for $C_{13}H_{17}BrNO_2$ [M + H]⁺: 298, 300 (1:1) found 298, 300 (1:1); ¹H NMR (400 MHz, CDCl₃): δ 7.38 (m, 2H), 7.06 (m, 1H), 4.62-4.54 (m, 1H), 4.01 (m, 0.5H), 3.79 (m, 0.5H), 3.597 (m, 1H), 3.45 (m, 1H), 3.24-3.11 (m, 1.5H), 3.02-2.93 (m, 0.5H), 2.85-2.77 (m, 0.5H), 2.67-2.59 (m, 0.5H), 2.33-2.23 (m, 3H), 1.25 (d, J = 6.3 Hz, 1.5H), 1.05 (d, J = 6.3 Hz, 1.5H). |
| I-16-12 | 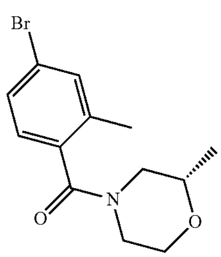 [SMILES: Cc1cc(Br)ccc1C(=O)N1CCO[C@@H](C)C1] | (S)-(4-bromo-2-methylphenyl)(2-methylmorpholino)methanone | LRMS (ESI) calc'd for $C_{13}H_{17}BrNO_2$ [M + H]⁺: 298, 300 (1:1) found 298, 300 (1:1); ¹H NMR (400 MHz, CDCl₃): δ 7.38 (m, 2H), 7.06 (m, 1H), 4.62-4.54 (m, 1H), 4.01 (m, 0.5H), 3.79 (m, 0.5H), 3.597 (m, 1H), 3.45 (m, 1H), 3.24-3.11 (m, 1.5H), 3.02-2.93 (m, 0.5H), 2.85-2.77 (m, 0.5H), 2.67-2.59 (m, 0.5H), 2.33-2.23 (m, 3H), 1.25 (d, J = 6.3 Hz, 1.5H), 1.05 (d, J = 6.3 Hz, 1.5H). |
| I-16-13 | 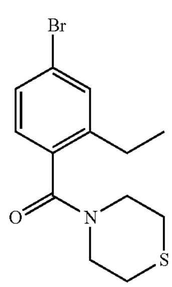 [SMILES: CCc1cc(Br)ccc1C(=O)N1CCSCC1] | (4-bromo-2-ethylphenyl)(thiomorpholino)methanone | LRMS (ESI) calc'd for $C_{13}H_{17}BrNOS$ [M + H]⁺: 314, 316 (1:1), 314, 316 (1:1); ¹H NMR (400 MHz, CDCl₃): δ 7.50 (s, 1H), 7.42 (d, J = 8.4 Hz, 1H), 7.05 (d, J = 8.4 Hz, 1H), 4.21-4.15 (m, 1H), 3.93 (m, 1H), 3.56-3.46 (m, 2H), 2.81-2.69 (m, 2H), 2.58 (m, 4H), 1.29 (t, J = 7.6 Hz, 3H). |

TABLE 3-continued

| Example | Structure | Compound Name | LRMS and/or $^1$H NMR |
|---|---|---|---|
| I-16-14 | 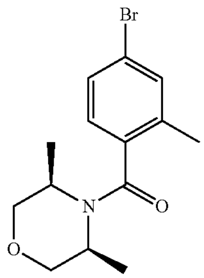 [SMILES: Cc1cc(Br)ccc1C(=O)N1[C@H](C)COC[C@@H]1C] | cis(4-bromo-2-methylphenyl)(3,5-dimethylmorpholino)methanone | LRMS (ESI) calc'd for $C_{14}H_{19}BrNO_2$ [M + H]$^+$: 312, 314 (1:1), 312, 314 (1:1); $^1$H NMR (400 MHz, CDCl$_3$): δ 7.43-7.37 (m, 2H), 7.09-6.98 (m, 1H), 3.91-3.35 (m, 6H), 2.57-2.23 (m, 3H), 1.51-1.12 (m, 6H). |
| I-16-15A and I-16-15B | 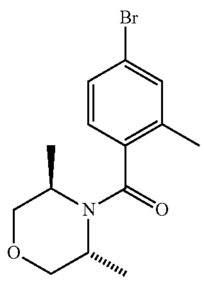 [SMILES: Cc1cc(Br)ccc1C(=O)N1[C@H](C)COC[C@H]1C] | trans(4-bromo-2-methylphenyl)(3,5-dimethylmorpholino)methanone Racemic aryl bromide was separated by prep HPLC using a Chiralcel OJ-H, eluting with 10% EtOH in hexanes, retention times = 7.5 and 10.0 minutes. | LRMS (ESI) calc'd for $C_{14}H_{19}BrNO_2$ [M + H]$^+$: 312, 314 (1:1), 312, 314(1:1); $^1$H NMR (400 MHz, CDCl$_3$): δ 7.36 (s, 1H), 7.35 (d, J = 8.1 Hz, 1H), 7.11 (d, J = 8.1 Hz, 1H), 3.92-3.57 (m, 4H), 3.52 (m, 2H), 2.34 (s, 3H), 1.51-1.12 (m, 6H). |

Intermediate 17

(4-bromo-2-(difluoromethyl)phenyl)(thiomorpholino)methanone

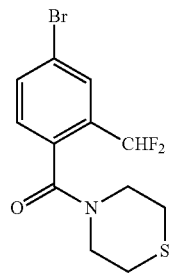

Step 1: (4-bromophenyl)(thiomorpholino)methanone

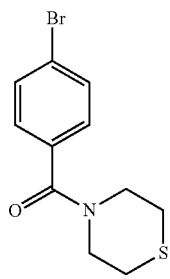 [SMILES: O=C(c1ccc(Br)cc1)N1CCSCC1]

A solution of 4-bromobenzoyl choride (10.00 g, 45.60 mmol), thiomorpholine (7.05 g, 68.3 mmol) and triethylamine (31.8 mL, 228 mmol) in DCM (50 mL) was stirred at ambient temperature for 1 hour. The reaction mixture was then quenched with water (80 mL), and extracted with DCM (×3). The combined organic layers were washed with water (40 mL), brine (30 mL), dried over anhydrous Na$_2$SO$_4$, filtered, and the filtrate was concentrated in vacuo to afford a residue that was purified by silica chromatography, eluting with 20% EtOAc/hexanes. LRMS (ESI) calc'd for $C_{11}H_{13}BrNOS$ [M+H]$^+$: 286, 288 (1:1) found 286, 288 (1:1); $^1$H NMR (400 MHz, CDCl$_3$): δ 7.57 (m, 2H), 7.35-7.26 (m, 2H), 4.10-3.60 (m, 4H), 2.80-2.55 (m, 4H).

Step 2: 5-bromo-2-(thiomorpholine-4-carbonyl)benzaldehyde

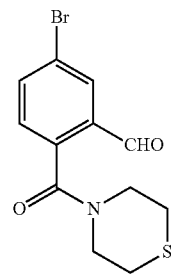 [SMILES: O=Cc1cc(Br)ccc1C(=O)N1CCSCC1]

To a 0° C. solution of 2,2,6,6-tetramethylpiperidine (0.560 g, 3.98 mmol) in THF (20 mL), was added (dropwise) n-butyllithium (1.67 mL, 4.18 mmol, 2.5 M in hexanes) over 5 minutes. The resulting solution was stirred for 10 minutes before being cooled to −78° C. (4-Bromophenyl)(thiomorpholino)methanone (0.570 g, 1.99 mmol) in THF (2 mL) was then quickly added to the solution and the solution was stirred at −78° C. for 1 hour. DMF (0.46 mL, 6.0 mmol) was added dropwase to the solution at −78° C. over 2 minutes, and then the reaction was warmed to ambient temperature over 30 minutes. The reaction mixture was quenched with water (40 mL), extracted with EtOAc (×3), and the combined organic layers was washed with water, brine, dried over anhydrous Na$_2$SO$_4$, filtered and the filtrate was concentrated in vacuo. The residue was purified by silica chromatography, eluting with 9% EtOAc/hexanes to afford the title compound as an oil. LRMS (ESI) calc'd for C$_{12}$H$_{13}$BrNO$_2$S [M+H]$^+$: 314, 316 (1:1) found 314, 316 (1:1); $^1$H NMR (400 MHz, DMSO-d$_6$): δ 9.94 (s, 1H), 8.16 (d, J=2.0 Hz, 1H), 7.95 (dd, J=8.0, 2.0 Hz, 1H), 7.43 (d, J=8.0 Hz, 1H), 3.91 (m, 2H), 3.44 (m, 2H), 2.73 (m, 2H), 2.46 (m, 2H).

Step 3: (4-bromo-2-(difluoromethyl)phenyl)(thiomorpholino)methanone (I-17)

Bis(2-methoxyethyl)aminosulfurtrifluoride (1.83 g, 8.28 mmol) was added dropwise to a stirred solution of 5-bromo-2-(thiomorpholine-4-carbonyl)benzaldehyde (0.26 g, 0.83 mmol) in DCM (2 mL) at −20° C. over 2 minutes. The reaction was then allowed to warm to room temperature and was stirred for 2 hours before being quenched with water (30 mL), and extracted with EtOAc (×3). The combined organic layers were washed with water, brine, dried over anhydrous Na$_2$SO$_4$, filtered, and the filtrate was concentrated in vacuo. The residue was purified by silica chromatography, eluting with 9% EtOAc/hexanes to afford the title compound as a solid. LRMS (ESI) calc'd for C$_{12}$H$_{13}$BrF$_2$NOS [M+H]$^+$: 336, 338 (1:1) found 336, 338 (1:1); $^1$H NMR (400 MHz, CDCl$_3$): δ 7.84 (s, 1H), 7.69 (m, 1H), 7.16 (d, J=8.0 Hz, 1H), 6.85 (t, J=52.4 Hz, 1H), 4.30-3.92 (m, 2H), 3.72-3.36 (m, 2H), 2.98-2.74 (m, 2H), 2.55 (m, 2H).

Intermediate 18

5-bromo-2-(1-methylpiperidin-4-yl)-2,3-dihydrobenzo[d]isothiazole 1,1-dioxide

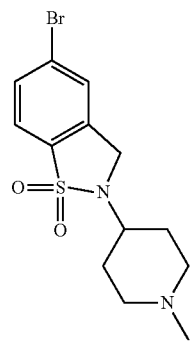

I-18

Step 1:
4-bromo-2-(bromomethyl)benzene-1-sulfonyl chloride

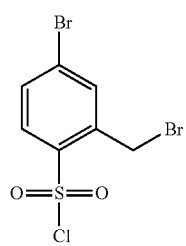

To a solution of N-bromosuccinimide (26.4 g, 148 mmol) and 4-bromo-2-methylbenzene-1-sulfonyl chloride (20.0 g, 74.2 mmol) in carbon tetrachloride (1.00 L) was added 2,2'-azobis(2-methylpropionitrile) (2.43 g, 14.8 mmol) at ambient temperature. The reaction mixture was stirred at 80° C. for 16 hours under argon, then cooled and the solids filtered. To the filtrate was then charged another portion of N-bromosuccinimide (26.4 g, 148 mmol) and 2,2'-azobis(2-methylpropionitrile) (2.43 g, 14.8 mmol) and the reaction was stirred at 80° C. for an additional 16 hours under argon. The solids were again filtered, and the filtrate was concentrated in vacuo. The residue was used next step without further purification.

Step 2: tert-butyl 4-(4-bromo-2-(bromomethyl)phenylsulfonamido)piperidine-1-carboxylate

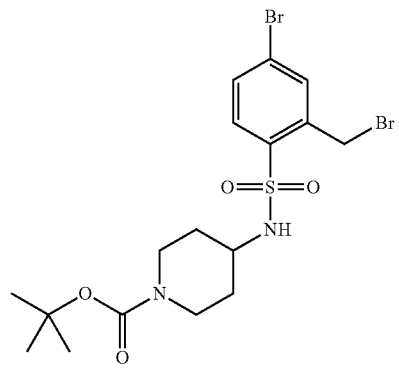 [SMILES: CC(C)(C)OC(=O)N1CCC(NS(=O)(=O)c2ccc(Br)cc2CBr)CC1]

To a solution of 4-bromo-2-(bromomethyl)benzene-1-sulfonyl chloride (60.0 g, 172 mmol) in DCM (1.00 L) was added a solution of tert-butyl 4-aminopiperidine-1-carboxylate (20.7 g, 103 mmol) and triethylamine (34.8 g, 344 mmol) in DCM (100 mL) at ambient temperature. The mixture was stirred at ambient temperature for 3 hours, then quenched with water (500 mL), extracted with DCM (×3), and the combined organic layers were washed with brine, dried over anhydrous Na$_2$SO$_4$ and filtered. The filtrate was concentrated in vacuo and the residue was purified by silica chromatography, eluting with 25% EtOAc in hexanes to afford the title compound as a solid. LRMS (ESI) calc'd for C$_{13}$H$_{17}$Br$_2$N$_2$O$_4$S [M−t-Bu+2H]$^+$: 455, 457, 459 (1:2:1) found 455, 457, 459 (1:2:1).

Step 3: tert-butyl 4-(5-bromo-1,1-dioxidobenzo[d]isothiazol-2(3H)-yl)piperidine-1-carboxylate

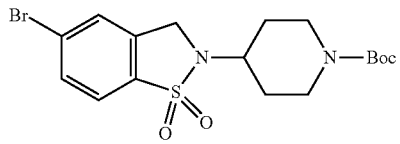 [SMILES: CC(C)(C)OC(=O)N1CCC(N2Cc3cc(Br)ccc3S2(=O)=O)CC1]

To a room temperature solution of tert-butyl 4-(4-bromo-2-(bromomethyl)phenylsulfonamido)piperidine-1-carboxylate (50.0 g, 98.0 mmol) in acetonitrile/water (3/1, 400 mL), was added sodium bicarbonate (24.6 g, 293 mmol). The mixture was stirred at 80° C. for 16 hours and then concentrated in vacuo. The residue was diluted with water (200 mL), extracted with EtOAc (×3), and the combined organic layers were dried over anhydrous Na₂SO₄ and filtered. The filtrate was concentrated in vacuo and the residue was purified by silica chromatography, eluting with 20% ethyl acetate in hexanes to afford the title compound as a solid. LRMS (ESI) calc'd for $C_{13}H_{16}BrN_2O_4S$ [M−t-Bu+2H]⁺: 375, 377 (1:1) found 375, 377 (1:1); ¹H NMR (400 MHz, CD₃OD): δ 7.76 (s, 1H), 7.74 (d, J=8.4 Hz, 1H), 7.65 (d, J=8.4 Hz, 1H), 4.44 (s, 2H), 4.08 (d, J=13.5 Hz, 2H), 3.78-3.71 (m, 1H), 2.98-2.83 (m, 2H), 2.00-1.94 (m, 2H), 1.85-1.73 (m, 2H), 1.43 (s, 9H).

Step 4: 5-bromo-2-(piperidin-4-yl)-2,3-dihydrobenzo[d]isothiazole 1,1-dioxide

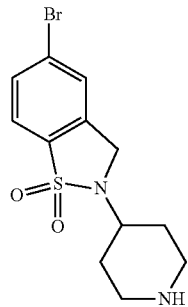 [SMILES: O=S1(=O)c2ccc(Br)cc2CN1C1CCNCC1]

To a stirred mixture of tert-butyl 4-(5-bromo-1,1-dioxidobenzo[d]isothiazol-2(3H)-yl)piperidine-1-carboxylate (2.40 g, 5.56 mmol) in dichloromethane (40 mL) was added (dropwise) trifluoroacetic acid (1.90 g, 16.7 mmol) at ambient temperature. The reaction mixture was stirred at ambient temperature for 1 hour and then concentrated in vacuo. The residue was adjusted to pH=8 with aqueous ammonia, and the mixture was extracted with EtOAc (×3). The combined organic layers were washed with brine, dried over anhydrous Na₂SO₄, filtered, and the filtrate was concentrated in vacuo to afford the title compound as an oil that was used as is in the next step without further purification. LRMS (ESI) calc'd for $C_{12}H_{16}BrN_2O_2S$ [M+H]⁺: 331, 333 (1:1), found 331, 333 (1:1).

Step 5: 5-bromo-2-(1-methylpiperidin-4-yl)-2,3-dihydrobenzo[d]isothiazole 1,1-dioxide (I-18)

To a stirred mixture of 5-bromo-2-(piperidin-4-yl)-2,3-dihydrobenzo[d]isothiazole 1,1-dioxide (80 mg, 0.24 mmol) and formaldehyde (22 mg, 0.73 mmol) in methanol (15 mL) at room temperature, was added sodium cyanoborohydride (46 mg, 0.73 mmol). The reaction was stirred at ambient temperature for 2 hours, then concentrated and quenched by the addition of water (10 mL). The mixture was extracted with EtOAc (×3), dried over Na₂SO₄, filtered, and the filtrate was concentrated to the title compound as an oil that was used as is. LRMS (ESI) calc'd for $C_{13}H_{18}BrN_2O_2S$ [M+H]⁺: 345, 347 (1:1), found 345, 347 (1:1).

Intermediate 19

5-bromo-2-(4,4-difluoro-1-methylcyclohexyl)isoindolin-1-one

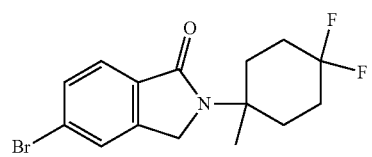

Step 1: 4,4-difluoro-1-methylcyclohexanamine

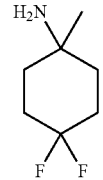

To a solution of 4,4-difluoro-1-methylcyclohexanecarboxylic acid (4.60 g, 25.8 mmol) and triethylamine (3.92 g, 38.7 mmol) in toluene (100 mL), was added (dropwise) diphenylphosphorazidate (8.53 g, 31.0 mmol) at ambient temperature. The resulting solution was stirred at ambient temperature for 3 hours and then heated to 100° C. for 12 hours. The reaction was then quenched by addition of water (100 mL) and extracted with EtOAc (×3). The combined organic layers were dried over anhydrous Na₂SO₄, filtered, and the filtrate was concentrated in vacuo to afford crude 1,1-difluoro-4-isocyanato-4-methylcyclohexane that was then taken up in 1,4-dioxane (20 mL). Aqueous hydrochloric acid (57.1 mL, 57.1 mmol, 1M) was then added at ambient temperature and the resulting solution was stirred for 12 hours and then concentrated in vacuo. The residue was adjusted pH=9 with aqueous sodium carbonate and the solution was extracted with EtOAc (×3). The combined organic layers were dried over anhydrous Na₂SO₄, filtered, and the filtrate was concentrated in vacuo to afford the title compound as an oil. ¹H NMR (300 MHz, CDCl₃): δ 2.15-1.95 (m, 2H), 1.93-1.79 (m, 2H), 1.69-1.60 (m, 6H), 1.19 (s, 3H).

Step 2: methyl 4-bromo-2-(bromomethyl)benzoate

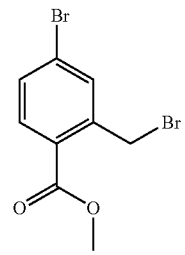

A solution of AIBN (3.58 g, 21.8 mmol), NBS (38.8 g, 218 mmol) and methyl 4-bromo-2-methylbenzoate (50.0 g, 218 mmol) in $CCl_4$ (1.0 L) was stirred for 16 hours at reflux. The reaction was cooled to ambient temperature, quenched with water (300 mL), and the organic layer was collected and concentrated in vacuo. The residue was purified by silica chromatography, eluting with 1% EtOAc/hexanes to afford the title compound as a solid. $^1$H NMR (300 MHz, $CDCl_3$): δ 7.81 (d, J=8.4 Hz, 1H), 7.63 (s, 1H), 7.51 (d, J=8.4 Hz, 1H), 4.90 (s, 2H), 3.94 (s, 3H).

Step 3: 5-bromo-2-(4,4-difluoro-1-methylcyclohexyl)isoindolin-1-one (I-19)

Triethylamine (3.39 g, 33.5 mmol) was added to methyl 4-bromo-2-(bromomethyl)benzoate (2.06 g, 6.70 mmol) and 4,4-difluoro-1-methylcyclohexanamine (1.00 g, 6.70 mmol) in toluene (60 mL). The mixture was stirred at 110° C. for 16 hours, then concentrated in vacuo and purified by silica chromatography, eluting with 0-6% EtOAc/hexanes to afford the title compound as a solid. LRMS (ESI) calc'd for $C_{15}H_{17}BrF_2NO$ [M+H]$^+$: 344, 346 (1:1), found 344, 346 (1:1); $^1$H NMR (300 MHz, $CDCl_3$): δ 7.80-7.42 (m, 3H), 4.39 (s, 2H), 2.73 (m, 2H), 2.10-1.83 (m, 6H), 1.42 (s, 3H).

Intermediate 20

4-(4-bromophenyl)-1-methylpiperidine

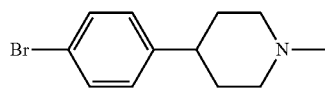

I-20

To a stirred solution of sodium acetate (4.45 g, 54.2 mmol), 4-(4-bromophenyl)piperidine hydrochloride (5.00 g, 18.1 mmol) and acetic acid (2.17 g, 36.2 mmol) in MeOH (50 mL) was added formaldehyde (1.08 g, 36.2 mmol). The mixture was stirred at ambient temperature for 3 hours. Sodium cyanotrihydroborate (2.27 g, 36.2 mmol) was added and the mixture was stirred at ambient temperature for 16 hours. The reaction mixture was quenched with water (20 mL), extracted with ethyl acetate (×3), and the combined organic layers were dried over anhydrous sodium sulfate, filtered, and the filtrate was concentrated in vacuo. The residue was purified by silica chromatography, eluting with 0-10% DCM/MeOH to afford the title compound as a solid. LRMS (ESI) calc'd for $C_{12}H_{17}BrN$ [M+H]$^+$: 254, 256 (1:1), found 254, 256 (1:1); $^1$H NMR (400 MHz, $CDCl_3$): δ 7.42 (d, J=8.4 Hz, 2H), 7.11 (d, J=8.4 Hz, 2H), 3.05 (d, J=11.6 Hz, 2H), 2.48 (m, 1H), 2.38 (s, 3H), 2.19-2.09 (m, 2H), 1.85-1.76 (m, 4H).

Intermediate 21

4-(4-bromophenyl)-1-(2,2,2-trifluoroethyl)piperidine

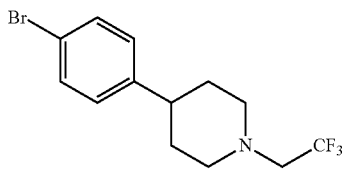

I-21

To a stirred solution of DIPEA (0.78 mL, 2.2 mmol) and 4-(4-bromophenyl)piperidine hydrochloride (0.20 g, 0.72 mmol) in DCM (5 mL), was added dropwise a solution of 2,2,2-trifluoroethyl trifluoromethanesulfonate (0.25 g, 1.1 mmol) in DCM (0.5 mL) at ambient temperature. The mixture was stirred at ambient temperature for 16 hours, then concentrated in vacuo and purified by silica chromatography, eluting with 17% ethyl acetate/hexanes to afford the title compound as an oil. LRMS (ESI) calc'd for $C_{13}H_{16}BrF_3N$ [M+H]$^+$: 322, 324 (1:1), found 322, 324 (1:1); $^1$H NMR (300 MHz, $CDCl_3$): δ 7.43 (d, J=8.4 Hz, 2H), 7.11 (d, J=8.4 Hz, 2H), 3.10-2.97 (m, 4H), 2.52-2.40 (m, 3H), 1.82-1.70 (m, 4H).

Example 1-1 tert-butyl 4-(3-(4-(N,N-dimethylsulfamoyl)phenylamino)-4-oxo-4,5-dihydropyrazolo[4,3-c]pyridin-1-yl)-4-ethylpiperidine-1-carboxylate

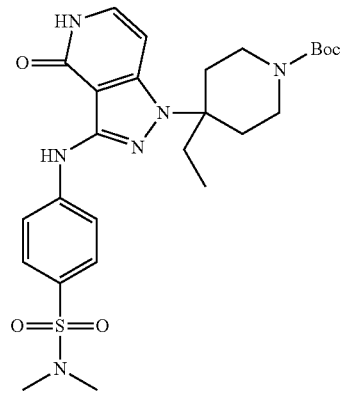 [SMILES: CCC1(n2nc(Nc3ccc(S(=O)(=O)N(C)C)cc3)c3c(=O)[nH]ccc32)CCN(C(=O)OC(C)(C)C)CC1]

Step 1: tert-butyl 4-(4-(benzyloxy)-3-((4-(N,N-dimethylsulfamoyl)phenyl)amino)-1H-pyrazolo[4,3-c]pyridin-1-yl)-4-(cyanomethyl)piperidine-1-carboxylate

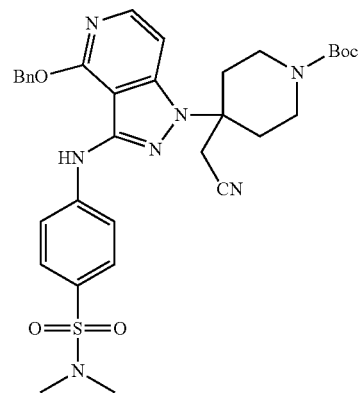 [SMILES: CN(C)S(=O)(=O)c1ccc(Nc2nn(C3(CC#N)CCN(C(=O)OC(C)(C)C)CC3)c3ccnc(OCc4ccccc4)c23)cc1]

Under nitrogen, a mixture of tert-butyl 4-[3-amino-4-(benzyloxy)-1H-pyrazolo[4,3-c]pyridin-1-yl]-4-(cyanomethyl)piperidine-1-carboxylate (3.00 g, 6.49 mmol), 4-bromo-N,N-dimethylbenzene-1-sulfonamide (3.42 g, 13.0 mmol), di-tert-butyl(2',4',6'-triisopropylbiphenyl-2-yl)phosphine (1.93 g, 4.54 mmol), tris(dibenzylideneacetone)dipalladium(0)-chloroform (1.66 g, 1.62 mmol) and potassium acetate (1.26 g, 12.9 mmol) in 2-propanol (70 mL) was heated to 80° C. for 18 hours. The mixture was filtered and the filtrate was concentrated in vacuo. The residue was purified by silica chromatography, eluting with 60% EtOAc/hexanes the title compound as a solid. LRMS (ESI) calc'd for $C_{33}H_{40}N_7O_5S$ [M+H]$^+$: 647, found 647; $^1$H NMR (600 MHz, DMSO-d$_6$): δ 8.58 (s, 1H), 7.91 (d, J=6.7 Hz, 1H), 7.73 (m, 2H), 7.68 (d, J=9.0 Hz, 2H), 7.52 (d, J=7.0 Hz, 2H), 7.41 (t, J=7.0 Hz, 3H), 7.34 (t, J=7.5 Hz, 1H), 5.63 (s, 2H), 3.81 (d, J=12.6 Hz, 2H), 3.34 (s, 2H), 3.09 (br s, 2H), 2.80 (d, J=14.0 Hz, 2H), 2.60 (s, 6H), 2.09 (m, 2H), 1.43 (s, 9H).

Step 2: tert-butyl 4-(4-(benzyloxy)-3-((4-(N,N-dimethylsulfamoyl)phenyl)amino)-1H-pyrazolo[4,3-c]pyridin-1-yl)-4-(2-oxoethyl)piperidine-1-carboxylate

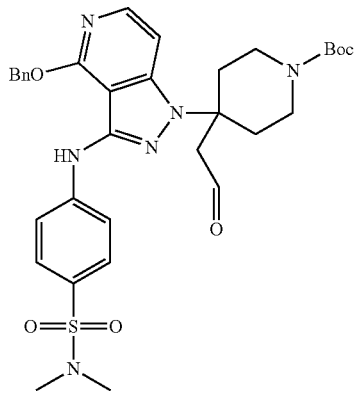 [SMILES: CN(C)S(=O)(=O)c1ccc(Nc2nn(C3(CC=O)CCN(C(=O)OC(C)(C)C)CC3)c3ccnc(OCc4ccccc4)c23)cc1]

To a solution of tert-butyl 4-[4-(benzyloxy)-3-[[4-(dimethylsulfamoyl)phenyl]amino]-1H-pyrazolo[4,3-c]pyridin-1-yl]-4-(cyanomethyl)piperdine-1-carboxylate (0.10 g, 0.15 mmol) in DCM (10 mL) at −78° C. under nitrogen, was added (dropwise) a solution of diisobutyl aluminium hydride (0.5 mL, 2.5 M in THF). The reaction was stirred for 2 hours at −40° C. before being quenched with water (2 mL) at 0° C. The mixture was then extracted with dichloromethane (×2), and the organic layers were combined, dried over anhydrous sodium sulfate, filtered, and the filtrate was concentrated in vacuo to afford the title compound as a solid. LRMS (ESI) calc'd for $C_{33}H_{41}N_6O_6S$ [M+H]$^+$: 649, found 649.

Step 3: tert-butyl 4-((1,3-dithiolan-2-yl)methyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate

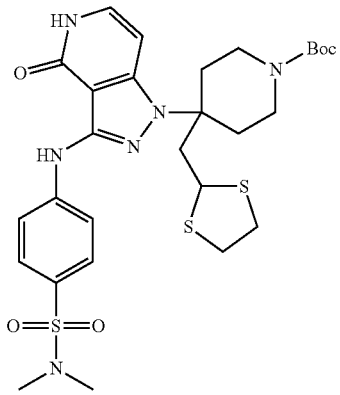 [SMILES: CN(C)S(=O)(=O)c1ccc(Nc2nn(C3(CC4SCCS4)CCN(C(=O)OC(C)(C)C)CC3)c3cc[nH]c(=O)c23)cc1]

To a solution of tert-butyl 4-[4-(benzyloxy)-3-[[4-(dimethylsulfamoyl)phenyl]amino]-1H-pyrazolo[4,3-c]pyridin-1-yl]-4-(2-oxoethylpiperidine-1-carboxylate (0.50 g, 0.77 mmol) in DCM (30 mL), was added ethane-1,2-dithiol (0.5 mL) and 4-methylbenzenesulfonic acid (0.10 g, 0.40 mmol). The mixture was stirred for 4 hours at 40° C. and then concentrated in vacuo. The residue was purified by silica chromatography, eluting with 33% EtOAc/hexanes to give the title compound as a solid. LRMS (ESI) calc'd for $C_{28}H_{39}N_6O_5S_3$ [M+H]$^+$: 635, found 635.

Step 4: tert-butyl 4-(3-(4-(N,N-dimethylsulfamoyl)phenylamino)-4-oxo-4,5-dihydropyrazolo[4,3-c]pyridin-1-v 1)-4-ethylpiperidine-1-carboxylate To a mixture of tert-butyl 4-(3-[[4-(dimethylsulfamoyl)phenyl]amino]-4-hydroxy-1H-pyrazolo[4,3-c]pyridin-1-yl)-4-(1,3-dithiolan-2-ylmethyl)piperidine-1-carboxylate (0.20 g, 0.32 mmol) in THF (15 mL), was added Raney Ni (1.00 g) under a hydrogen atmosphere. The mixture was stirred for 16 hours at ambient temperature, then the solid was filtered and the filtrate was concentrated in vacuo. The residue was purified by Prep-HPLC using a SunFire Prep C18 OBD Column, eluting with a 50-70% methanol gradient in water with 10 mM ammonium bicarbonate. LRMS (ESI) calc'd for $C_{26}H_{37}N_6O_5S$ [M+H]$^+$: 545, found 545; $^1$H NMR (400 MHz, DMSO-d$_6$): δ 11.20 (s, 1H), 8.66 (s, 1H), 7.84 (d, J=7.2 Hz, 2H), 7.65 (d, J=6.4 Hz, 2H), 7.14 (s, 1H), 6.65 (s, 1H), 3.74 (d, J=10.0 Hz, 2H), 3.06 (s, 2H), 2.58-2.50 (m, 8H), 1.89 (s, 4H); 1.39 (s, 9H), 0.54 (s, 3H).

The following examples in Table 4 were prepared in analogy to Example 1-1 above.

TABLE 4

| Example | Structure | Compound Name | LRMS and/or ¹H NMR |
|---|---|---|---|
| 1-2 | 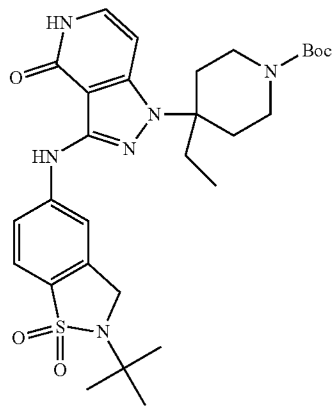 [SMILES: CCC1(n2nc(Nc3ccc4c(c3)CN(C(C)(C)C)S4(=O)=O)c3c(=O)[nH]ccc32)CCN(C(=O)OC(C)(C)C)CC1] | 2-tert-butyl-5-[[1-(1-tert-butyl-6-ethyl-2-oxo-1,3-oxazocan-6-yl)-4-oxo-1H,4H,5H-pyrazolo[4,3-c]pyridin-3-yl]amino]-2,3-dihydro-1,2-benzothiazole-1,1-dione | LRMS (ESI) calc'd for $C_{29}H_{41}N_6O_5S$ [M + H]$^+$: 585, found 585; ¹H NMR (400 MHz, CD$_3$OD): δ 7.84 (s, 1H), 7.75 (d, J = 8.0 Hz, 1H), 7.63 (d, J = 8.9 Hz, 1H), 7.20 (d, J = 8.0 Hz, 1H), 6.74 (d, J = 7.2 Hz, 1H), 4.57 (s, 2H), 3.92 (d, J = 12.4 Hz, 2H), 2.88-2.71 (m, 3H), 1.92-2.02 (m, 2H), 1.76 (s, 9H), 1.73 (s, 9H), 1.48-1.43 (m, 4H), 0.90-0.60 (m, 2H). |
| 1-3 | 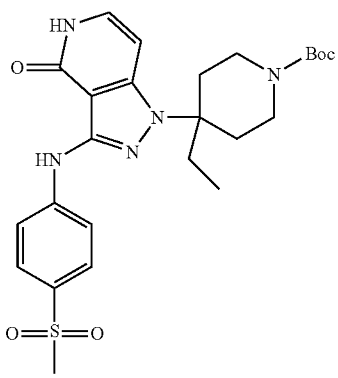 [SMILES: CCC1(n2nc(Nc3ccc(S(C)(=O)=O)cc3)c3c(=O)[nH]ccc32)CCN(C(=O)OC(C)(C)C)CC1] | tert-butyl 4-ethyl-4-(3-(4-(methylsulfonyl)phenylamino)-4-oxo-4,5-dihydropyrazolo[4,3-c]pyridin-1-yl)piperidine-1-carboxylate | LRMS (ESI) calc'd for $C_{25}H_{34}N_5O_5S$ [M + H]$^+$: 516, found 516; ¹H NMR (400 MHz, DMSO-d$_6$): δ 11.24 (br s, 1H), 8.67 (s, 1H), 7.95-7.75 (m, 4H), 7.15-7.36 (m, 1H), 6.66 (d, J = 9.2 Hz,, 1H), 3.77-3.73 (m, 2H), 3.20-3.00 (m, 5H), 2.72-2.58 (m, 2H), 1.89 (s, 3H), 1.95-1.75 (m, 1H), 1.39 (s, 9H), 0.65-0.45 (m, 3H). |

Example 2-1 tert-butyl 4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-ethylpiperidine-1-carboxylate

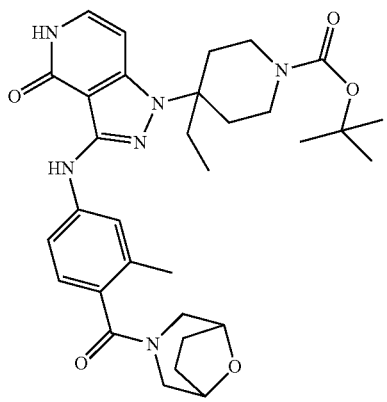 [SMILES: CCC1(n2nc(Nc3ccc(C(=O)N4CC5CCC(C4)O5)c(C)c3)c3c(=O)[nH]ccc32)CCN(C(=O)OC(C)(C)C)CC1]

Tris(dibenzylideneacetone) dipalladium(0)-chloroform adduct (34 mg, 0.033 mmol) was added to tert-butyl 4-(3-amino-4-oxo-4,5-dihydro-1H-pyrazolo[4,3-c]pyridin-1-yl)-4-ethylpiperidine-1-carboxylate (0.12 g, 0.33 mmol), 8-oxa-3-azabicyclo[3.2.1]octan-3-yl(4-bromo-2-methylphenyl)methanone (0.12 g, 0.40 mmol), dibutyl(2',4',6'-triisopropyl-[1,1'-biphenyl]-2-yl)phosphine (28 mg, 0.066 mmol) and potassium acetate (65 mg, 0.66 mmol) in 2-propanol (1 mL). The mixture was stirred at 80° C. under nitrogen for 4 hours, then concentrated in vacuo and purified by column chromatography, eluting with 0-10% MeOH/DCM and then purified by Prep-HPLC using a Sunfire C18 column, eluting with 40-60% CH$_3$CN in water (0.05% ammonium bicarbonate) the title compound, which after concentration in vacuo, afforded a solid. LRMS (ESI) calc'd for $C_{32}H_{43}N_6O_5$ [M+H]$^+$: 591 found 591; ¹H NMR (400 MHz, DMSO-d$_6$): δ 11.19 (s, 1H), 8.19 (s, 1H), 7.49 (m, 2H), 7.09 (m, 2H), 6.61 (d, J=7.5 Hz, 1H), 4.39 (s, 1H), 4.20 (m, 2H), 3.75 (m, 2H), 3.34 (m, 1H), 3.08-2.94 (m, 4H), 2.60 (m, 2H), 2.21 (s, 3H), 1.90-1.60 (m, 8H), 1.39 (s, 9H), 0.54 (t, J=7.2 Hz, 3H).

Table 5 discloses intermediates that were prepared in an analogous manner to that of Example 2-1 above. In some instances, the reaction could alternatively employ tBuX-Phos-Pd-G3, [(2-Di-tert-butylphosphino-2',4',6'-triisopropyl-1,1'-biphenyl)-2-(2'-amino-1,1'-biphenyl)]palladium(II) methanesulfonate, or XantPhos ligand in place of the t-BuXPhos ligand, in t-amyl alcohol, at or around 70-80° C.

TABLE 5

| Example | Structure | Compound Name | LRMS and/or ¹H NMR |
|---|---|---|---|
| 2-2 | 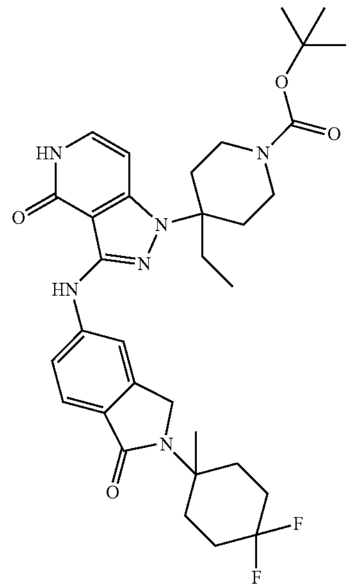 [SMILES: CCC1(n2nc(Nc3ccc4c(c3)CN(C3(C)CCC(F)(F)CC3)C4=O)c3c(=O)[nH]ccc32)CCN(C(=O)OC(C)(C)C)CC1] | tert-butyl 4-(3-(2-(4,4-difluoro-1-methylcyclohexyl)-1-oxoisoindolin-5-ylamino)-4-oxo-4,5-dihydropyrazolo[4,3-c]pyridin-1-yl)-4-ethylpiperidine-1-carboxylate | LRMS (ESI) calc'd for $C_{33}H_{43}F_2N_6O_4[M + H]^+$: 625 found 625; ¹H NMR (400 MHz, DMSO-$d_6$): δ 11.23 (br s, 1H), 8.50 (s, 1H), 7.89 (s, 1H), 7.51 (m, 2H), 7.14 (m, 1H), 6.64 (d, J = 7.6 Hz, 1H), 4.53 (s, 2H), 3.73 (m, 2H), 3.03 (m, 2H), 2.74-2.58 (m, 4H), 1.97-1.88 (m, 8H), 1.74 (m, 2H), 1.40 (s, 9H), 1.39-1.23 (m, 3H), 0.55 (m, 3H). |
| 2-3 | 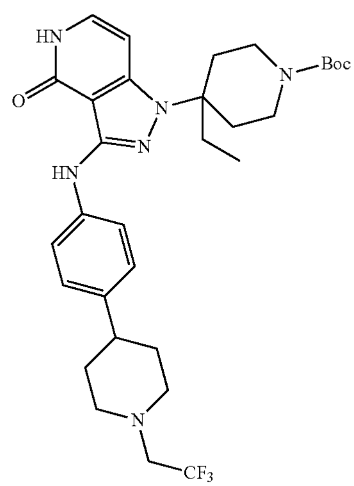 [SMILES: CCC1(n2nc(Nc3ccc(C4CCN(CC(F)(F)F)CC4)cc3)c3c(=O)[nH]ccc32)CCN(C(=O)OC(C)(C)C)CC1] | tert-butyl 4-ethyl-4-(4-oxo-3-(4-(1-(2,2,2-trifluoroethyl)piperidin-4-yl)phenylamino)-4,5-dihydropyrazolo [4,3-c]pyridin-1-yl) piperidine-1-carboxylate | LRMS (ESI) calc'd for $C_{31}H_{42}F_3N_6O_3[M + H]^+$: 603 found 603; ¹H NMR (400 MHz, DMSO-$d_6$): δ 11.14 (br s, 1H), 8.03 (s, 1H), 7.51 (d, J = 8.4 Hz, 2H), 7.16 (d, J = 8.4 Hz, 2H), 7.09 (m, 1H), 6.59 (d, J = 7.6 Hz, 1H), 3.73 (m, 2H), 3.19 (m, 2H), 3.02 (m, 4H), 2.58 (m, 2H), 2.43 (m, 3H), 1.86 (m, 4H), 1.70-1.61 (m, 4H), 1.39 (s, 9H), 0.55 (t, J = 7.2 Hz, 3H). |
| 2-4 | 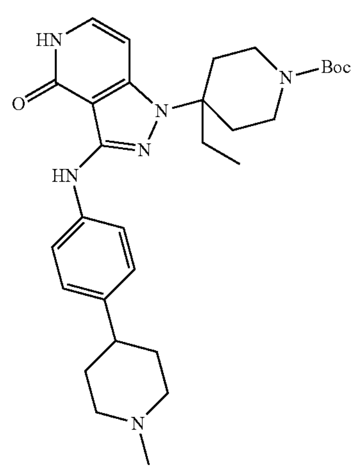 [SMILES: CCC1(n2nc(Nc3ccc(C4CCN(C)CC4)cc3)c3c(=O)[nH]ccc32)CCN(C(=O)OC(C)(C)C)CC1] | tert-butyl 4-ethyl-4-(3-(4-(1-methylpiperidin-4-yl)phenylamino)-4-oxo-4,5-dihydropyrazolo[4,3-c]pyridin-1-yl) piperidine-1-carboxylate | LRMS (ESI) calc'd for $C_{30}H_{43}N_6O_3[M + H]^+$: 535 found 535; ¹H NMR (400 MHz, DMSO-$d_6$): δ 11.15 (br s, 1H), 8.03 (s, 1H), 7.51 (m, 2H), 7.13 (m, 3H), 6.59 (d, J = 7.6 Hz, 1H), 3.74 (m, 2H), 3.04 (m, 2H), 2.88 (m, 2H), 2.59 (m, 2H), 2.38 (m, 1H), 2.21 (s, 3H), 2.00-1.92 (m, 2H), 1.86 (m, 4H), 1.67 (m, 4H), 1.39 (s, 9H), 0.53 (t, J = 7.2 Hz, 3H). |

TABLE 5-continued

| Example | Structure | Compound Name | LRMS and/or $^1$H NMR |
|---|---|---|---|
| 2-5 | 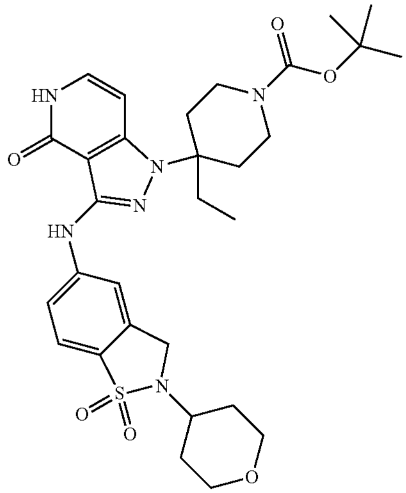 [SMILES: CCC1(n2nc(Nc3ccc4c(c3)CN(C3CCOCC3)S4(=O)=O)c3c(=O)[nH]ccc32)CCN(C(=O)OC(C)(C)C)CC1] | tert-butyl 4-ethyl-4-(3-{[2-(oxan-4-yl)-1,1-dioxo-2,3-dihydro-1,2-benzothiazol-5-yl] amino}-4-oxo-1H,4H,5H-pyrazolo [4,3-c]pyridin-1-yl) piperidine-1-carboxylate | LRMS (ESI) calc'd for $C_{30}H_{41}N_6O_6S$ [M + H]$^+$: 613, found 613; $^1$H NMR (400 MHz, DMSO-$d_6$): δ 11.29 (s, 1H), 8.68 (s, 1H), 7.89-7.77 (m, 1H), 7.79-7.61 (m, 2H), 7.15 (d, J = 7.4 Hz, 1H), 6.65 (d, J = 7.5 Hz, 1H), 4.46 (s, 2H), 3.92 (dt, J = 11.4, 3.5 Hz, 2H), 3.82-3.59 (m, 3H), 3.30-3.19 (m, 2H), 3.15-2.93 (m, 2H), 2.75-2.56 (m, 2H), 2.00-1.75 (m, 8H), 1.39 (s, 9H), 0.54 (t, J = 7.3 Hz, 3H). |
| 2-6 | 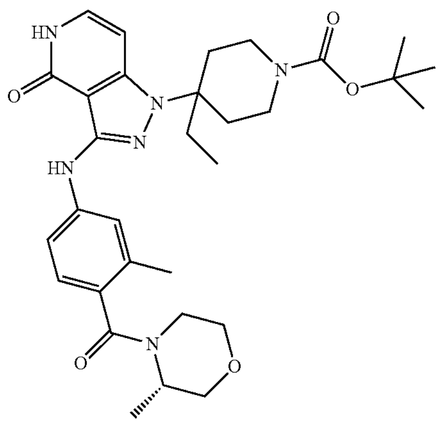 [SMILES: CCC1(n2nc(Nc3ccc(C(=O)N4CCOC[C@@H]4C)c(C)c3)c3c(=O)[nH]ccc32)CCN(C(=O)OC(C)(C)C)CC1] | (S)-tert-butyl 4-ethyl-4-(3-((3-methyl-4-(3-methylmorpholine-4-carbonyl)phenyl)amino)-4-oxo-4,5-dihydro-1H-pyrazolo[4,3-c] pyridin-1-yl) piperidine-1-carboxylate | LRMS (ESI) calc'd for $C_{31}H_{43}N_6O_5$ [M + H]$^+$: 579, found 579; $^1$H NMR (400 MHz, DMSO-$d_6$): δ 11.23 (d, J = 5.2 Hz, 1H), 8.23 (s, 1H), 7.53 (m, 2H), 7.16 (t, J = 7.3 Hz, 1H), 7.12 (br s, 1H), 6.64 (d, J = 7.3 Hz, 1H), 3.92-3.26 (m, 7H), 3.26-2.96 (m, 4H), 2.63 (d, J = 13.6 Hz, 2H), 2.26 (br s, 3H), 1.95-1.84 (m, 4H), 1.42 (s, 9H), 1.31-1.12 (m, 3H), 0.58 (t, J = 8.6 Hz, 3H). |
| 2-7 | 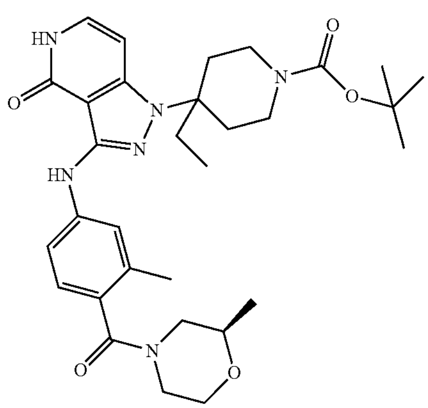 [SMILES: CCC1(n2nc(Nc3ccc(C(=O)N4CCO[C@H](C)C4)c(C)c3)c3c(=O)[nH]ccc32)CCN(C(=O)OC(C)(C)C)CC1] | (R)-tert-butyl-4-ethyl-4-(3-(3-methyl-4-(2-methylmorpholine-4-carbonyl)phenyl amino)-4-oxo-4,5-dihydropyrazolo[4,3-c]pyridin-1-yl) piperidine-1-carboxylate | LRMS (ESI) calc'd for $C_{31}H_{43}N_6O_5$ [M + H]$^+$: 579, found 579; $^1$H NMR (300 MHz, DMSO-$d_6$): δ 11.19 (br s, 1H), 8.20 (m, 1H), 7.57-7.43 (m, 2H), 7.15 (m, 2H), 6.62 (d, J = 7.2 Hz, 1H), 4.39-4.29 (m, 1H), 3.95-3.66 (m, 3H), 3.65-3.42 (m, 2H), 3.26-2.76 (m, 4H), 2.66-2.58 (m, 2H) 2.20 (s, 3H), 2.01-1.80 (m, 4H), 1.40 (s, 9H), 1.30-1.08 (m, 2H), 1.08-0.88 (m, 2H), 0.54 (t, J = 7.4 Hz, 3H). |

TABLE 5-continued

| Example | Structure | Compound Name | LRMS and/or ¹H NMR |
|---|---|---|---|
| 2-8 | 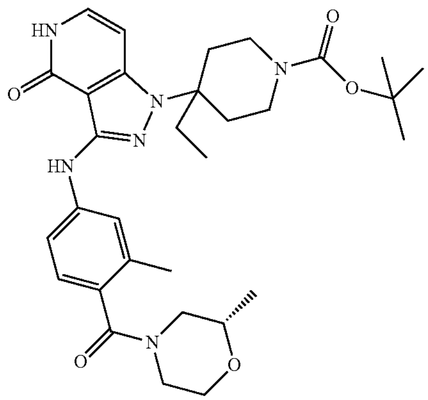 [SMILES: CCC1(n2nc(Nc3ccc(C(=O)N4CCO[C@@H](C)C4)c(C)c3)c3c(=O)[nH]ccc32)CCN(C(=O)OC(C)(C)C)CC1] | (S)-tert-butyl-4-ethyl-4-(3-(3-methyl-4-(2-methylmorpholine-4-carbonyl)phenylamino)-4-oxo-4,5-dihydropyrazolo[4,3-c]pyridin-1-yl) piperidine-1-carboxylate | LRMS (ESI) calc'd for $C_{31}H_{43}N_6O_5$ [M + H]⁺: 579, found 579; ¹H NMR (300 MHz, DMSO-d₆): δ 11.19 (br s, 1H), 8.20 (m, 1H), 7.49 (m, 2H), 7.14-7.08 (m, 2H), 6.62 (d, J = 7.5 Hz, 1H), 4.39-4.29 (m, 1H), 3.96-3.63 (m, 3H), 3.65-3.42 (m, 2H), 3.26-2.76 (m, 4H), 2.66-2.58 (m, 2H), 2.21 (s, 3H), 2.01-1.80 (m, 4H), 1.40 (s, 9H), 1.31-1.07 (m, 2H), 1.08-0.88 (m, 2H), 0.54 (t, J = 7.4 Hz, 3H). |
| 2-9 | 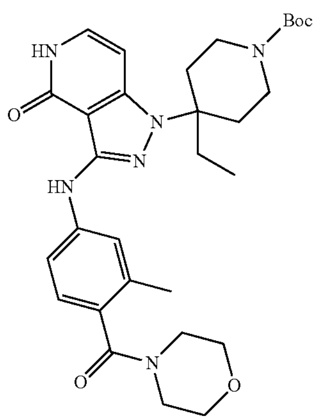 [SMILES: CCC1(n2nc(Nc3ccc(C(=O)N4CCOCC4)c(C)c3)c3c(=O)[nH]ccc32)CCN(C(=O)OC(C)(C)C)CC1] | tert-butyl 4-ethyl-4-(3-((3-methyl-4-(morpholine-4-carbonyl)phenyl)amino)-4-oxo-4,5-dihydro-1H-pyrazolo[4,3-c]pyridin-1-yl) piperidine-1-carboxylate | LRMS (ESI) calc'd for $C_{30}H_{41}N_6O_5$ [M + H]⁺: 565 found 565; ¹H NMR (300 MHz, CDCl₃): δ 9.75 (s, 1H), 7.97 (s, 1H), 7.45 (s, 2H), 7.10 (d, J = 7.5 Hz, 1H), 7.03 (s, 1H), 6.39 (d, J = 7.5 Hz, 1H), 3.81-3.60 (m, 8H), 3.32-3.13 (m, 4H), 2.65 (m, 2H), 2.32 (s, 3H), 1.86 (m, 4H), 1.45 (s, 9H), 0.64 (s, 3H). |
| 2-10 | 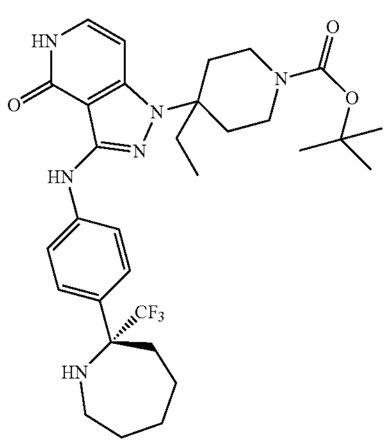 [SMILES: CCC1(n2nc(Nc3ccc([C@@]4(C(F)(F)F)CCCCCN4)cc3)c3c(=O)[nH]ccc32)CCN(C(=O)OC(C)(C)C)CC1] | (R or S)-tert-butyl 4-ethyl-4-(4-oxo-3-((4-(2-(trifluoromethyl) azepan-2-yl)phenyl) amino)-4,5-dihydro-1H-pyrazolo[4,3-c] pyridin-1-yl) piperidine-1-carboxylate | LRMS (ESI) calc'd for $C_{31}H_{42}F_3N_6O_3$ [M + H]⁺: 603, found 603; ¹H NMR (400 MHz, CD₃OD): δ 7.60 (d, J = 9.0 Hz, 2H), 7.51 (d, J = 9.0 Hz, 2H), 7.13 (d, J = 10.0 Hz, 1H), 6.68 (d, J = 10.0 Hz, 1H), 3.89 (m, 2H), 3.28-2.97 (m, 3H), 2.76 (m, 3H), 2.34 (m, 2H), 1.97-1.50 (m, 10H), 1.50 (s, 9H), 0.68 (t, J = 8.2 Hz, 3H). |

TABLE 5-continued

| Example | Structure | Compound Name | LRMS and/or ¹H NMR |
|---|---|---|---|
| 2-11 | 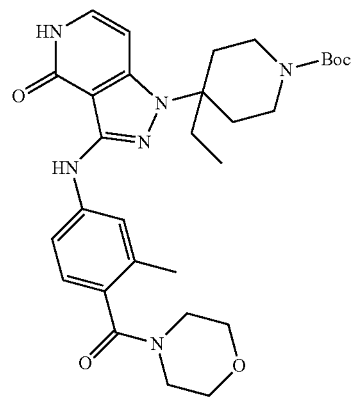 [SMILES: CCC1(n2nc(Nc3ccc(C(=O)N4CCOCC4)c(C)c3)c3c(=O)[nH]ccc32)CCN(C(=O)OC(C)(C)C)CC1] | tert-butyl-4-ethyl-4-(3-(3-methyl-4-(morpholine-4-carbonyl)phenyl amino)-4-oxo-4,5-dihydropyrazolo[4,3-c]pyridin-1-yl) piperidine-1-carboxylate | LRMS (ESI) calc'd for $C_{30}H_{41}N_6O_5$ [M + H]⁺: 565, found 565; ¹H NMR (400 MHz, DMSO-$d_6$): δ 11.20 (br, 1H), 8.19 (br, 1H), 7.49 (m, 2H), 7.11 (m, 2H), 6.61 (d, J = 7.6 Hz, 1H), 3.81-3.45 (m, 8H), 3.28-2.98 (m, 4H), 2.60-2.51 (m, 2H), 2.21 (s, 3H), 1.93-1.78 (m, 4H), 1.39 (s, 9H), 0.54 (t, J = 7.6 Hz, 3H). |
| 2-12 | 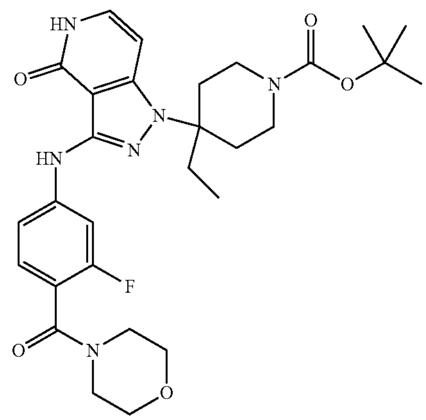 [SMILES: CCC1(n2nc(Nc3ccc(C(=O)N4CCOCC4)c(F)c3)c3c(=O)[nH]ccc32)CCN(C(=O)OC(C)(C)C)CC1] | tert-butyl 4-ethyl-4-(3-((3-fluoro-4-(morpholine-4-carbonyl)phenyl)amino)-4-oxo-4,5-dihydro-1H-pyrazolo[4,3-c] pyridin-1-yl) piperidine-1-carboxylate | LRMS (ESI) calc'd for $C_{29}H_{38}FN_6O_5$ [M + H]⁺: 569, found 569; ¹H NMR (400 MHz, DMSO-$d_6$): δ 11.23 (br s, 1H), 8.54 (s, 1H), 7.68 (m, 1H), 7.45 (m, 1H), 7.30 (m, 1H), 7.14 (m, 1H), 6.63 (m, 1H), 3.73 (m, 2H), 3.59 (m, 6H), 3.31 (m, 3H), 3.04 (m, 2H), 2.53 (m, 2H), 1.87 (m, 4H), 1.40 (s, 9H), 0.53 (t, J = 7.6 Hz, 3H). |
| 2-13 | 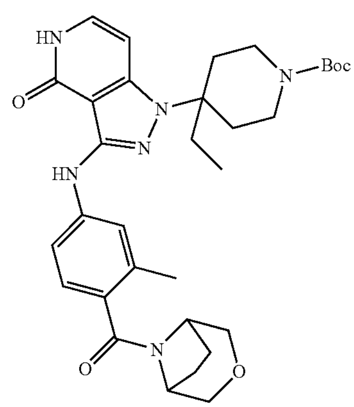 [SMILES: CCC1(n2nc(Nc3ccc(C(=O)N4C5CCC4COC5)c(C)c3)c3c(=O)[nH]ccc32)CCN(C(=O)OC(C)(C)C)CC1] | tert-butyl 4-(3-((4-(3-oxa-8-azabicyclo [3.2.1] octane-8-carbonyl)-3-methylphenyl)amino)-4-oxo-4,5-dihydro-1H-pyrazolo[4,3-c] pyridin-1-yl)-4-ethylpiperidine-1-carboxylate | LRMS (ESI) calc'd for $C_{32}H_{43}N_6O_5$ [M + H]⁺: 591 found 591; ¹H NMR (300 MHz, DMSO-$d_6$): δ 11.20 (br s, 1H), 8.22 (br s, 1H), 7.51 (s, 1H), 7.48 (d, J = 8.1 Hz, 1H), 7.19 (d, J = 8.1 Hz, 1H), 7.11 (d, J = 7.5 Hz, 1H), 6.61 (d, J = 7.5 Hz, 1H), 4.59-4.50 (m, 1H), 3.81-3.43 (m, 7H), 3.17-2.93 (m, 2H), 2.56 (m, 2H), 2.26 (s, 3H), 1.97-1.78 (m, 8H), 1.39 (s, 9H), 0.54 (t, J = 7.5 Hz, 3H). |

TABLE 5-continued

| Example | Compound Name | LRMS and/or ¹H NMR |
|---|---|---|
| 2-14 | tert-butyl 4-ethyl-4-(3-((3-methyl-4-(2-oxa-6-azaspiro[3.3]heptane-6-carbonyl)phenyl) amino)-4-oxo-4,5-dihydro-1H-pyrazolo [4,3-c]pyridin-1-yl) piperidine-1-carboxylate | LRMS (ESI) calc'd for $C_{31}H_{41}N_6O_5$ [M + H]⁺: 577 found 577; ¹H NMR (300 MHz, CDCl₃): δ 9.57 (s, 1H), 8.04 (s, 1H), 7.46 (s, 2H), 7.20 (d, J = 7.2 Hz, 1H), 7.02 (s, 1H), 6.40 (d, J = 7.2 Hz, 1H), 4.82 (s, 4H), 4.30-4.18 (m, 4H), 3.88 (s, 2H), 3.16 (m, 2H), 2.67 (m, 2H), 2.41 (s, 3H), 1.89 (m, 4H), 1.45 (s, 9H), 0.65 (t, J = 10.8 Hz, 3H). |
| 2-15 | tert-butyl 4-(3-((4-((1R,4R)-2-oxa-5-azabicyclo[2.2.1]heptane-5-carbonyl)-3-methylphenyl)amino)-4-oxo-4,5-dihydro-1H-pyrazolo[4,3-c]pyridin-1-yl)-4-ethylpiperidine-1-carboxylate | LRMS (ESI) calc'd for $C_{31}H_{41}N_6O_5$ [M + H]⁺: 577, found 577; ¹H NMR (300 MHz, DMSO-d₆): δ 10.19 (br s, 1H), 8.20 (br s, 1H), 7.49 (m, 2H), 7.15 (m, 2H), 6.61 (d, J = 7.5 Hz, 1H), 4.84-4.64 (m, 1H), 4.55-4.02 (m, 1H), 3.80-3.61 (m, 4H), 3.50-2.96 (m, 4H), 2.65-2.51 (m, 2H), 2.25-2.18 (m, 3H), 1.95-1.68 (m, 6H), 1.39 (s, 9H), 0.54 (t, J = 7.5 Hz, 3H). |
| 2-16 | (S or R)-tert-butyl-4-ethyl-4-(4-oxo-3-((4-(2-(trifluoromethyl) azepan-2-yl)phenyl) amino)-4,5-dihydro-1H-pyrazolo[4,3-c]pyridin-1-yl) piperidine-1-carboxylate | LRMS (ESI) calc'd for $C_{31}H_{42}F_3N_6O_3$ [M + H]⁺: 603 found 603; ¹H NMR (300 MHz, DMSO-d₆): δ 11.18 (s, 1H), 8.17 (s, 1H), 7.61 (d, J = 9.0 Hz, 2H), 7.50 (d, J = 9.0 Hz, 2H), 7.11 (d, J = 7.5 Hz, 1H), 6.61 (d, J = 7.5 Hz, 1H), 3.72 (m, 2H), 3.20-2.89 (m, 4H), 2.62-2.53 (m, 2H), 2.26-2.15 (m, 3H), 1.87 (m, 5H), 1.58-1.40 (m, 5H), 1.39 (s, 9H), 0.54 (t, J = 7.2 Hz, 3H). |
| 2-17 | tert-butyl 4-(3-((3-(cyanomethyl)phenyl) amino)-4-oxo-4,5-dihydro-1H-pyrazolo [4,3-c]pyridin-1-yl)-4-ethylpiperidine-1-carboxylate | LRMS (ESI) calc'd for $C_{26}H_{33}N_6O_3$ [M + H]⁺: 477 found 477; ¹H NMR (400 MHz, DMSO-d₆): δ 11.19 (s, 1H), 8.21 (s, 1H), 7.85 (s, 1H), 7.42 (m, 1H), 7.28 (m, 1H), 7.11 (m, 1H), 6.82 (d, J = 7.2 Hz, 1H), 6.61 (d, J = 7.6 Hz, 1H), 4.04 (s, 2H), 3.77 (m, 2H), 3.01 (br s, 2H), 2.65 (m, 2H), 1.89-1.81 (m, 4H), 1.39 (s, 9H), 0.55 (t, J = 7.2 Hz, 3H). |

TABLE 5-continued

| Example | Structure | Compound Name | LRMS and/or ¹H NMR |
|---------|-----------|---------------|---------------------|
| 2-18 | 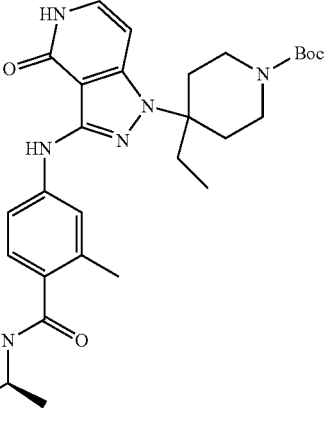 | tert-butyl 4-(3-(4-((3S,5R)-3,5-dimethylmorpholine-4-carbonyl)-3-methylphenylamino)-4-oxo-2,3,4,5-tetrahydropyrazolo[4,3-c]pyridin-1-yl)-4-ethylpiperidine-1-carboxylate | LRMS (ESI) calc'd for C$_{32}$H$_{44}$N$_6$O$_5$ [M + H]$^+$: 593, found 593; ¹H NMR (400 MHz, DMSO-d$_6$): δ 11.19 (br s, 1H), 8.18 (s, 1H), 7.49 (m, 2H), 7.11 (m, 2H), 6.61 (d, J = 10.4 Hz, 1H), 3.75 (m, 4H), 3.65-3.53 (m, 2H), 3.43 (m, 2H), 3.25-3.05 (m, 2H), 2.73-2.61 (m, 2H), 2.21 (s, 3H), 1.87 (m, 4H), 1.39 (s, 9H), 1.39 (m, 6H), 0.58 (t, J = 5.2 Hz, 3H). |
| 2-19 | 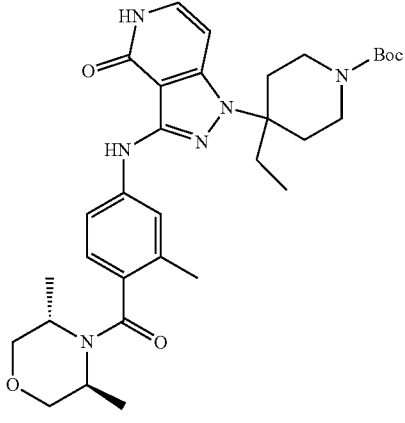 [SMILES: CCC1(n2nc(Nc3ccc(C(=O)N4[C@@H](C)COC[C@@H]4C)c(C)c3)c3c(=O)[nH]ccc32)CCN(C(=O)OC(C)(C)C)CC1] | tert-butyl 4-(3-(4-((3S,5S or 3R,5R)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate | LRMS (ESI) calc'd for C$_{32}$H$_{44}$N$_6$O$_5$ [M + H]$^+$: 593, found 593; ¹H NMR (400 MHz, DMSO-d$_6$): δ 11.19 (br s, 1H), 8.22 (s, 1H), 7.50 (m, 2H), 7.20 (m, 1H), 7.12 (m, 1H), 6.61 (d, J = 10 Hz, 1H), 3.83 (m, 6H), 3.75 (m, 2H), 3.27-3.05 (m, 2H), 2.59 (m, 2H), 2.28 (s, 3H), 1.90-1.81 (m, 4H), 1.39 (s, 9H), 1.18 (m, 6H), 0.58 (t, J = 5.2 Hz, 3H). SFC analysis using Chiralcel OD-H with 35% MeOH (with 0.25% DEA), showed it as Peak 1 (retention time 3.7 minutes). |
| 2-20 | 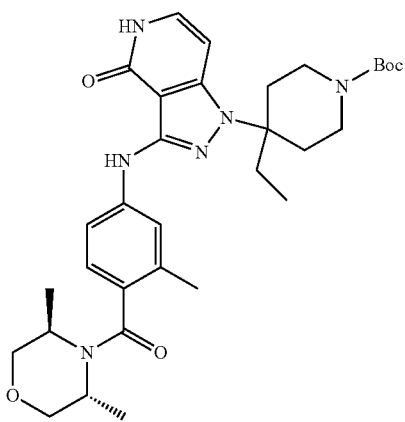 [SMILES: CCC1(n2nc(Nc3ccc(C(=O)N4[C@H](C)COC[C@H]4C)c(C)c3)c3c(=O)[nH]ccc32)CCN(C(=O)OC(C)(C)C)CC1] | tert-butyl 4-(3-(4-((3R,5R or 3S,5S)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate | LRMS (ESI) calc'd for C$_{32}$H$_{44}$N$_6$O$_5$ [M + H]$^+$: 593, found 593; ¹H NMR (400 MHz, DMSO-d$_6$): δ 11.19 (br s, 1H), 8.22 (s, 1H), 7.50 (m, 2H), 7.20 (m, 1H), 7.12 (m, 1H), 6.61 (d, J = 10 Hz, 1H), 3.83 (m, 6H), 3.75 (m, 2H), 3.27-3.05 (m, 2H), 2.59 (m, 2H), 2.28 (s, 3H), 1.90-1.81 (m, 4H), 1.39 (s, 9H), 1.18 (m, 6H), 0.58 (t, J = 5.2 Hz, 3H). SFC analysis using Chiralcel OD-H with 35% MeOH (with 0.25% DEA), showed it as Peak 2 (retention time 4.4 minutes). |

TABLE 5-continued

| Example | Structure | Compound Name | LRMS and/or ¹H NMR |
|---------|-----------|---------------|--------------------|
| 2-21 | 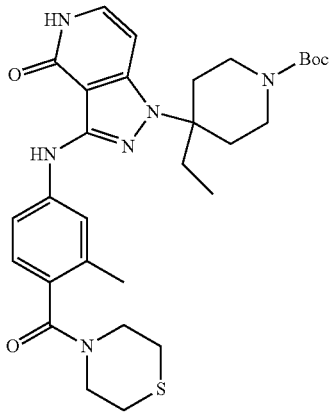 [SMILES: CCC1(n2nc(Nc3ccc(C(=O)N4CCSCC4)c(C)c3)c3c(=O)[nH]ccc32)CCN(C(=O)OC(C)(C)C)CC1] | tert-butyl 4-ethyl-4-(3-(3-methyl-4-(thiomorpholine-4-carbonyl)phenyl amino)-4-oxo-4,5-dihydropyrazolo[4,3-c]pyridin-1-yl) piperidine-1-carboxylate | LRMS (ESI) calc'd for $C_{30}H_{41}N_6O_4S$ [M + H]⁺: 581, found 581; ¹H NMR (400 MHz, DMSO-$d_6$): δ 11.18 (br s, 1H), 8.19 (s, 1H), 7.49 (m, 2H), 7.12 (m, 2H), 6.61 (d, J = 10 Hz, 1H), 3.75 (m, 4H), 3.44 (m, 2H), 3.04 (m, 2H), 2.61-2.51 (m, 6H), 2.20 (s, 3H), 1.92-1.81 (m, 4H), 1.39 (s, 9H), 0.54 (t, J = 9.6 Hz, 3H). |
| 2-22 | 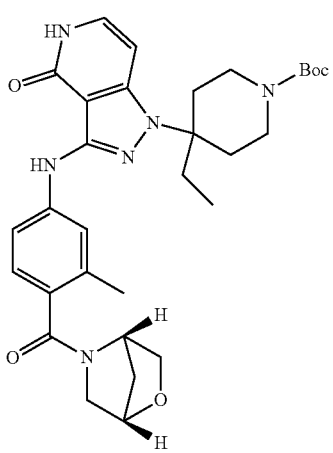 [SMILES: CCC1(n2nc(Nc3ccc(C(=O)N4C[C@@H]5C[C@H]4CO5)c(C)c3)c3c(=O)[nH]ccc32)CCN(C(=O)OC(C)(C)C)CC1] | tert-butyl 4-(3-(4-(((1S,4S)-5-oxa-2-aza-bicyclo[2.2.1]heptane-2-carbonyl)-3-methylphenylamino)-4-oxo-4,5-dihydropyrazolo[4,3-c]pyridin-1-yl)-4-ethylpiperidine-1-carboxylate | LRMS (ESI) calc'd for $C_{31}H_{41}N_6O_5$ [M + H]⁺: 577, found 577; ¹H NMR (400 MHz, DMSO-$d_6$): δ 11.21 (br s, 1H), 8.21 (m, 1H), 7.50 (m, 2H), 7.19-7.11 (m, 2H), 6.62 (d, J = 7.2 Hz, 1H), 4.84-4.67 (m, 1H), 4.52-4.09 (m, 1H), 3.75 (m, 4H), 3.62 (m, 1H), 3.46 (m, 1H), 3.28-3.18 (m, 2H), 2.54 (m, 2H), 2.24 (m, 3H), 1.89-1.81 (m, 6H), 1.40 (s, 9H), 0.57 (t, J = 7.2 Hz, 3H). |
| 2-23 | 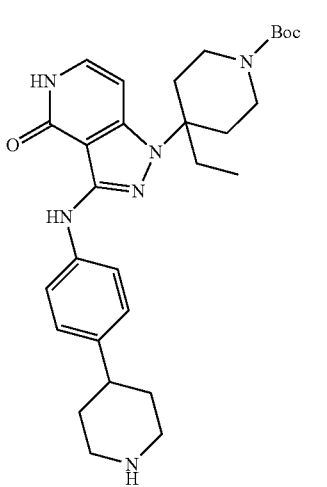 [SMILES: CCC1(n2nc(Nc3ccc(C4CCNCC4)cc3)c3c(=O)[nH]ccc32)CCN(C(=O)OC(C)(C)C)CC1] | tert-butyl 4-ethyl-4-(4-oxo-3-(4-(piperidin-4-yl)phenylamino)-4,5-dihydropyrazolo[4,3-c]pyridin-1-yl) piperidine-1-carboxylate | LRMS (ESI) calc'd for $C_{29}H_{41}N_6O_3$ [M + H]⁺: 521, found 521; ¹H NMR (300 MHz, CD$_3$OD): δ 7.51 (d, J = 8.7 Hz, 2H), 7.16 (d, J = 8.7 Hz, 2H), 7.09 (d, J = 7.5 Hz, 1H), 6.65 (d, J = 7.5 Hz, 1H), 3.92-3.85 (m, 2H), 3.29-3.03 (m, 4H), 2.88-2.57 (m, 5H), 1.95-1.62 (m, 8H), 1.41 (s, 9H), 0.61 (t, J = 7.5 Hz, 3H). |

TABLE 5-continued

| Example | Structure | Compound Name | LRMS and/or ¹H NMR |
|---------|-----------|---------------|---------------------|
| 2-24 | 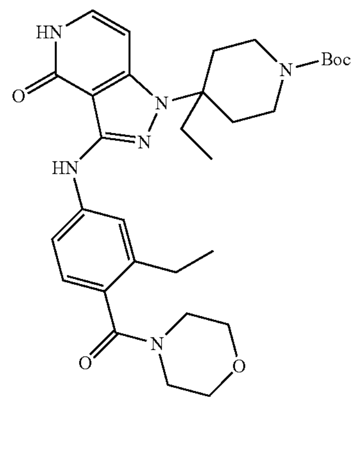 [SMILES: CCc1cc(Nc2nn(C3(CC)CCN(C(=O)OC(C)(C)C)CC3)c3cc[nH]c(=O)c23)ccc1C(=O)N1CCOCC1] | tert-butyl 4-ethyl-4-(3-((3-ethyl-4-(morpholine-4-carbonyl)phenyl)amino)-4-oxo-4,5-dihydro-1H-pyrazolo[4,3-c] pyridin-1-yl) piperidine-1-carboxylate | LRMS (ESI) calc'd for $C_{31}H_{43}N_6O_5$ [M + H]⁺: 579, found 579; ¹H NMR (300 MHz, DMSO-$d_6$): δ 11.18 (br s, 1H), 8.20 (s, 1H), 7.75-7.59 (m, 1H), 7.42 (m, 1H), 7.10 (m, 2H), 6.61 (d, J = 7.2 Hz, 1H), 3.82-3.74 (m, 2H), 3.72-3.56 (m, 4H), 3.55-3.42 (m, 2H), 3.26-2.95 (m, 4H), 2.71-2.56 (m, 4H), 1.96-1.73 (m, 4H), 1.39 (s, 9H), 1.18 (t, J = 7.5 Hz, 3H), 0.55 (t, J = 7.2 Hz, 3H). |
| 2-25 | 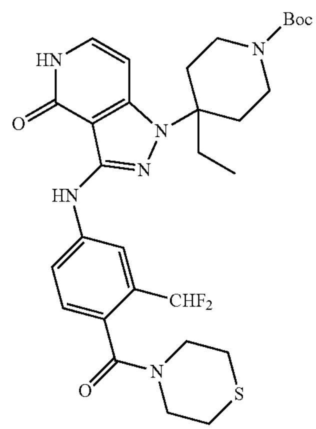 [SMILES: CCC1(n2nc(Nc3ccc(C(=O)N4CCSCC4)c(C(F)F)c3)c3c(=O)[nH]ccc32)CCN(C(=O)OC(C)(C)C)CC1] | tert-butyl 4-(3-(3-(difluoromethyl)-4-(thiomorpholine-4-carbonyl)phenyl amino)-4-oxo-4,5-dihydropyrazolo[4,3-c]pyridin-1-yl)-4-ethylpiperidine-1-carboxylate | LRMS (ESI) calc'd for $C_{30}H_{39}F_2N_6O_4S$ [M + H]⁺: 617 found 617; ¹H NMR (300 MHz, DMSO-$d_6$): δ 11.21 (s, 1H), 8.52 (s, 1H), 8.27 (s, 1H), 7.67 (d, J = 8.7 Hz, 1H), 7.32 (d, J = 8.7 Hz, 1H), 7.14 (d, J = 7.5 Hz, 1H), 6.80 (t, J = 55.2 Hz, 1H), 6.63 (d, J = 7.5 Hz, 1H), 3.86-3.74 (m, 4H), 3.51 (m, 2H), 3.04 (m, 2H), 2.68 (m, 6H), 1.92-1.79 (m, 4H), 1.39 (s, 9H), 0.54 (t, J = 7.2 Hz, 3H). |
| 2-26 | 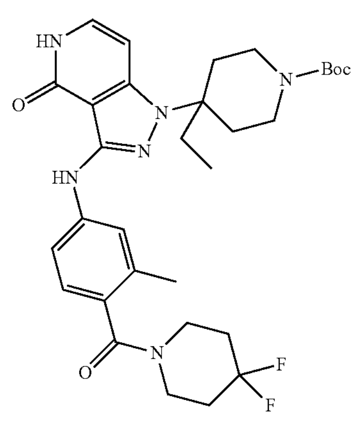 [SMILES: CCC1(n2nc(Nc3ccc(C(=O)N4CCC(F)(F)CC4)c(C)c3)c3c(=O)[nH]ccc32)CCN(C(=O)OC(C)(C)C)CC1] | tert-butyl 4-(3-(4-(4,4-difluoropiperidine-1-carbonyl)-3-methyl phenylamino)-4-oxo-4,5-dihydropyrazolo [4,3-c]pyridin-1-yl)-4-ethylpiperidine-1-carboxylate | LRMS (ESI) calc'd for $C_{31}H_{41}F_2N_6O_4$ [M + H]⁺: 599, found 599; ¹H NMR (300 MHz, DMSO-$d_6$): δ 11.18 (br s, 1H), 8.20 (m, 1H), 7.50 (m, 2H), 7.15 (m, 2H), 6.61 (d, J = 7.2 Hz, 1H), 3.75 (m, 3H), 3.15-2.95 (m, 5H), 2.60 (m, 2H), 2.21 (s, 3H), 2.12-1.95 (m, 3H), 1.95-1.78 (m, 5H), 1.49 (s, 9H), 0.55 (t, J = 7.2 Hz, 3H). |

TABLE 5-continued

| Example | Structure | Compound Name | LRMS and/or ¹H NMR |
|---|---|---|---|
| 2-27 | 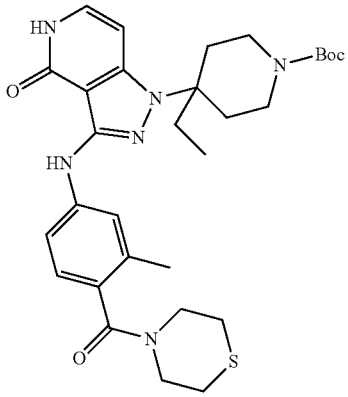 [SMILES: CCC1(n2nc(Nc3ccc(C(=O)N4CCSCC4)c(C)c3)c3c(=O)[nH]ccc32)CCN(C(=O)OC(C)(C)C)CC1] | tert-butyl-4-ethyl-4-(3-(3-methyl-4-(thiomorpholine-4-carbonyl)phenyl amino)-4-oxo-4,5-dihydropyrazolo[4,3-c]pyridin-1-yl) piperidine-1-carboxylate | LRMS (ESI) calc'd for $C_{30}H_{41}N_6O_4S$ [M + H]⁺: 581, found 581; ¹H NMR (400 MHz, DMSO-d₆): δ 11.19 (br s, 1H), 8.16 (m, 1H), 7.50 (m, 2H), 7.12 (m, 2H), 6.62 (d, J = 7.6 Hz, 1H), 3.76 (m, 2H), 3.58-3.42 (m, 2H), 3.32 (m, 2H), 3.20-2.96 (m, 2H), 2.76-2.56 (m, 6H), 2.20 (s, 3H), 1.88 (m, 4H), 1.39 (s, 9H), 0.55 (t, J = 7.4 Hz, 3H). |
| 2-28 | 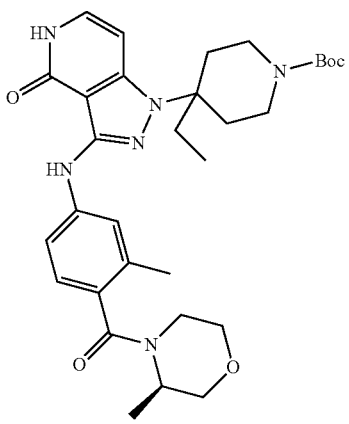 [SMILES: CCC1(n2nc(Nc3ccc(C(=O)N4CCOC[C@H]4C)c(C)c3)c3c(=O)[nH]ccc32)CCN(C(=O)OC(C)(C)C)CC1] | (R)-tert-butyl-4-ethyl-4-(3-(3-methyl-4-(3-methylmorpholine-4-carbonyl)phenyl amino)-4-oxo-4,5-dihydropyrazolo[4,3-c]pyridin-1-yl) piperidine-1-carboxylate | LRMS (ESI) calc'd for $C_{31}H_{43}N_6O_5$ [M + H]⁺: 579, found 579; ¹H NMR (400 MHz, DMSO-d₆): δ 11.23 (d, J = 5.2 Hz, 1H), 8.23 (s, 1H), 7.53 (m, 2H), 7.16 (t, J = 7.3 Hz, 1H), 7.12 (br s, 1H), 6.64 (d, J = 7.3 Hz, 1H), 3.92-3.26 (m, 7H), 3.26-2.96 (m, 4H), 2.63 (d, J = 13.6 Hz, 2H), 2.26 (br s, 3H), 1.95-1.84 (m, 4H), 1.42 (s, 9H), 1.31-1.12 (m, 3H), 0.58 (t, J = 8.6 Hz, 3H). |
| 2-29 | 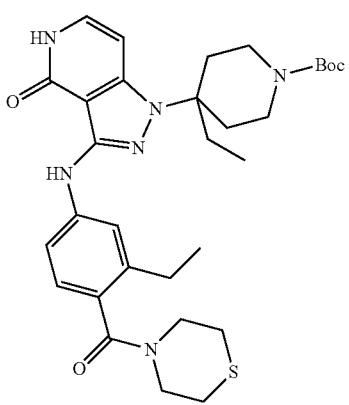 [SMILES: CCc1cc(Nc2nn(C3(CC)CCN(C(=O)OC(C)(C)C)CC3)c3cc[nH]c(=O)c23)ccc1C(=O)N1CCSCC1] | tert-butyl 4-ethyl-4-(3-(3-ethyl-4-(thiomorpholine-4-carbonyl)phenyl amino)-4-oxo-4,5-dihydropyrazolo[4,3-c]pyridin-1-yl) piperidine-1-carboxylate | LRMS (ESI) calc'd for $C_{31}H_{43}N_6O_4S$ [M + H]⁺: 595 found 595; ¹H NMR (400 MHz, DMSO-d₆): δ 11.19 (br s, 1H), 8.21 (s, 1H), 7.68 (s, 1H), 7.41 (m, 1H), 7.12 (m, 2H), 6.62 (d, J = 7.6 Hz, 1H), 4.05 (m, 1H), 3.76 (m, 3H), 3.46-3.32 (m, 2H), 3.05-2.94 (m, 2H), 2.67-2.33 (m, 8H), 1.91-1.83 (m, 4H), 1.39 (s, 9H), 1.20 (m, 3H), 0.54 (m, 3H). |

TABLE 5-continued

| Example | Structure | Compound Name | LRMS and/or ¹H NMR |
|---|---|---|---|
| 2-30 | 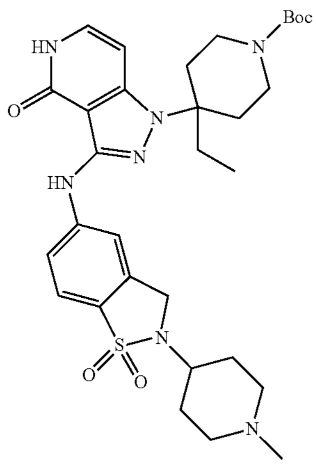 [SMILES: CCC1(n2nc(Nc3ccc4c(c3)CN(C3CCN(C)CC3)S4(=O)=O)c3c(=O)[nH]ccc32)CCN(C(=O)OC(C)(C)C)CC1] | tert-butyl 4-ethyl-4-(3-((2-(1-methyl piperidin-4-yl)-1,1-dioxido-2,3-dihydrobenzo [d] isothiazol-5-yl) amino)-4-oxo-4,5-dihydro-1H-pyrazolo [4,3-c]pyridin-1-yl) piperidine-1-carboxylate | LRMS (ESI) calc'd for $C_{31}H_{44}N_7O_5S$ [M + H]: 626, found 626; ¹H NMR (300 MHz, $CD_3OD$): δ 7.80 (s, 1H), 7.73-7.69 (m, 1H), 7.62 (d, J = 8.7 Hz, 1H), 7.15 (d, J = 7.5 Hz, 1H), 6.69 (d, J = 7.5 Hz, 1H), 4.44 (s, 2H), 3.98-3.84 (m, 2H), 3.54 (m, 1H), 3.27-3.08 (m, 2H), 2.94 (m, 2H), 2.73 (m, 2H), 2.29 (s, 3H), 2.21 (m, 2H), 2.02-1.87 (m, 8H), 1.50 (s, 9H), 0.60 (t, J = 3.4 Hz, 3H). |
| 2-31 | 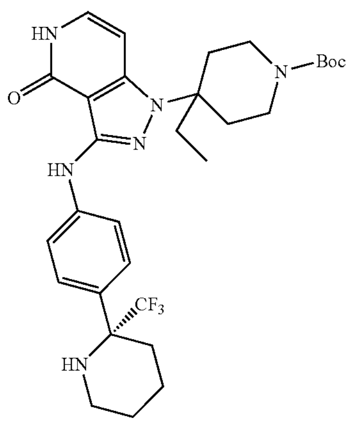 [SMILES: CCC1(n2nc(Nc3ccc([C@@]4(C(F)(F)F)CCCCN4)cc3)c3c(=O)[nH]ccc32)CCN(C(=O)OC(C)(C)C)CC1] | (R or S)-tert-butyl 4-ethyl-4-(4-oxo-3-((4-(2-(trifluoromethyl) piperidin-2-yl)phenyl) amino)-4,5-dihydro-1H-pyrazolo[4,3-c] pyridin-1-yl) piperidine-1-carboxylate | LRMS (ESI) calc'd for $C_{30}H_{40}F_3N_6O_3$ [M + H]⁺: 589, found 589; ¹H NMR (400 MHz, $CD_3OD$): δ 7.70 (d, J = 8.8 Hz, 2H), 7.52 (d, J = 8.4 Hz, 2H), 7.18 (d, J = 7.6 Hz, 1H), 6.72 (d, J = 8.4 Hz, 1H), 3.95 (d, J = 13.6 Hz, 2H), 3.15 (br s, 2H), 2.88-2.79 (m, 3H), 2.68-2.53 (m, 2H), 2.02-1.86 (m, 5H), 1.74 (m, 1H), 1.56 (m, 3H), 1.48 (s, 9H), 0.65 (m, 3H). |
| 2-32 | 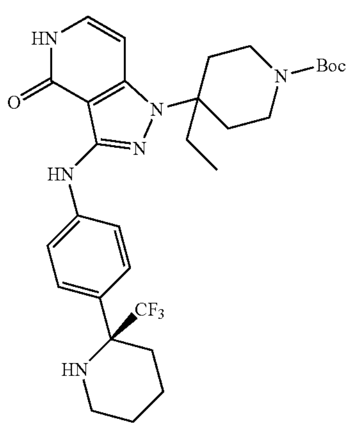 [SMILES: CCC1(n2nc(Nc3ccc([C@]4(C(F)(F)F)CCCCN4)cc3)c3c(=O)[nH]ccc32)CCN(C(=O)OC(C)(C)C)CC1] | (S or R)-tert-butyl 4-ethyl-4-(4-oxo-3-((4-(2-(trifluoromethyl) piperidin-2-yl)phenyl) amino)-4,5-dihydro-1H-pyrazolo[4,3-c] pyridin-1-yl) piperidine-1-carboxylate | LRMS (ESI) calc'd for $C_{30}H_{40}F_3N_6O_3$ [M + H]⁺: 589, found 589; ¹H NMR (400 MHz, $CD_3OD$): δ 7.70 (d, J = 8.8 Hz, 2H), 7.52 (d, J = 8.4 Hz, 2H), 7.18 (d, J = 7.6 Hz, 1H), 6.72 (d, J = 8.4 Hz, 1H), 3.95 (d, J = 13.6 Hz, 2H), 3.15 (br s, 2H), 2.88-2.79 (m, 3H), 2.68-2.53 (m, 2H), 2.02-1.86 (m, 5H), 1.74 (m, 1H), 1.56 (m, 3H), 1.48 (s, 9H), 0.65 (m, 3H). |

TABLE 5-continued

| Example | Structure | Compound Name | LRMS and/or ¹H NMR |
|---|---|---|---|
| 2-33 | 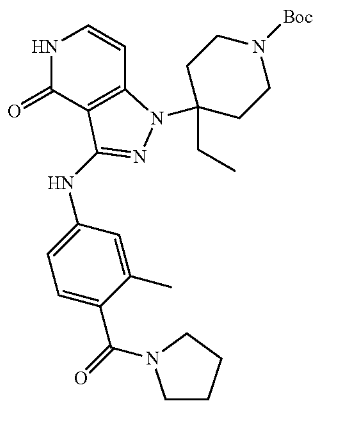 [SMILES: CCC1(n2nc(Nc3ccc(C(=O)N4CCCC4)c(C)c3)c3c(=O)[nH]ccc32)CCN(C(=O)OC(C)(C)C)CC1] | tert-butyl 4-ethyl-4-(3-(3-methyl-4-(pyrrolidine-1-carbonyl)phenyl amino)-4-oxo-4,5-dihydropyrazolo[4,3-c]pyridin-1-yl) piperidine-1-carboxylate | LRMS (ESI) calc'd for $C_{30}H_{41}N_6O_4$ [M + H]⁺: 549, found 549; ¹H NMR (300 MHz, DMSO-$d_6$): δ 11.18 (d, J = 5.6 Hz, 1H), 8.16 (s, 1H), 7.47 (m, 2H), 7.12 (m, 2H), 6.61 (d, J = 7.6 Hz, 1H), 3.76 (m, 2H), 3.46 (m, 2H), 3.13 (m, 4H), 2.61-2.51 (m, 2H), 2.21 (s, 3H), 1.89-1.79 (m, 8H), 1.77 (s, 9H), 0.55 (t, J = 7.2 Hz, 3H). |
| 2-34 | 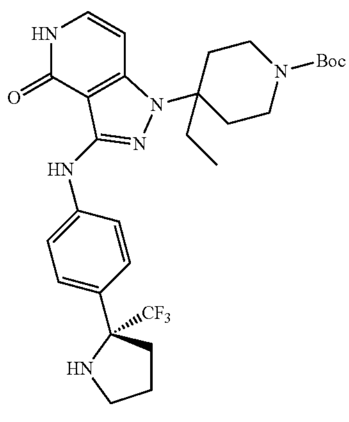 [SMILES: CCC1(n2nc(Nc3ccc([C@@]4(C(F)(F)F)CCCN4)cc3)c3c(=O)[nH]ccc32)CCN(C(=O)OC(C)(C)C)CC1] | (R or S)-tert-butyl 4-ethyl-4-(4-oxo-3-(4-(2-(trifluoromethyl) pyrrolidin-2-yl) phenylamino)-4,5-dihydropyrazolo[4,3-c]pyridin-1-yl) piperidine-1-carboxylate | LRMS (ESI) calc'd for $C_{29}H_{38}F_3N_6O_3$ [M + H]⁺: 575, found 575; ¹H NMR (300 MHz, DMSO-$d_6$): δ 11.18 (br s, 1H), 8.18 (s, 1H), 7.61 (m, 2H), 7.45 (m, 2H), 7.10 (m, 1H), 6.61 (m, 1H), 3.75 (m, 2H), 3.02 (m, 4H), 2.60 (m, 2H), 2.49 (m, 2H), 2.37 (m, 1H), 2.36-2.21 (m, 1H), 1.87 (m, 4H), 1.81-1.71 (m, 1H), 1.39 (s, 9H), 0.53 (t, J = 6.9 Hz, 3H). |
| 2-35 | 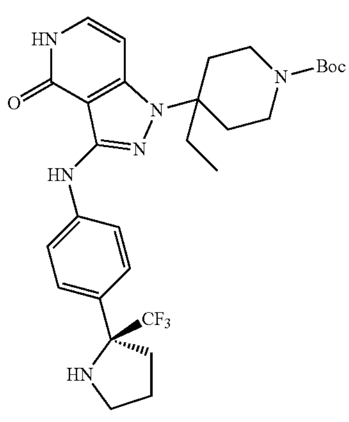 [SMILES: CCC1(n2nc(Nc3ccc([C@]4(C(F)(F)F)CCCN4)cc3)c3c(=O)[nH]ccc32)CCN(C(=O)OC(C)(C)C)CC1] | (S or R)-tert-butyl 4-ethyl-4-(4-oxo-3-(4-(2-(trifluoromethyl) pyrrolidin-2-yl) phenylamino)-4,5-dihydropyrazolo[4,3-c]pyridin-1-yl) piperidine-1-carboxylate | LRMS (ESI) calc'd for $C_{29}H_{38}F_3N_6O_3$ [M + H]⁺: 575, found 575; ¹H NMR (300 MHz, DMSO-$d_6$): δ 11.18 (br s, 1H), 8.18 (s, 1H), 7.61 (m, 2H), 7.45 (m, 2H), 7.10 (m, 1H), 6.61 (m, 1H), 3.75 (m, 2H), 3.02 (m, 4H), 2.60 (m, 2H), 2.49 (m, 2H), 2.37 (m, 1H), 2.36-2.21 (m, 1H), 1.87 (m, 4H), 1.81-1.71 (m, 1H), 1.39 (s, 9H), 0.53 (t, J = 6.9 Hz, 3H). |

TABLE 5-continued

| Example | Structure | Compound Name | LRMS and/or ¹H NMR |
|---|---|---|---|
| 2-36 | 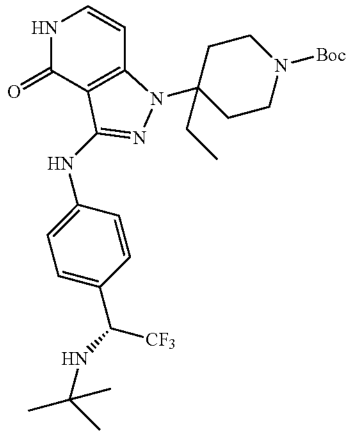 [SMILES: CCC1(n2nc(Nc3ccc([C@@H](NC(C)(C)C)C(F)(F)F)cc3)c3c(=O)[nH]ccc32)CCN(C(=O)OC(C)(C)C)CC1] | (R or S)-tert-butyl 4-(3-(4-(1-(tert-butylamino)-2,2,2-trifluoroethyl)phenyl-amino)-4-oxo-4,5-dihydropyrazolo[4,3-c]pyridin-1-yl)-4-ethylpiperidine-1-carboxylate (Peak A, separated by HPLC, using ChiralpakAD-H column, eluting with 90% EtOH in hexanes, retention time: 14.5 minutes.) | LRMS (ESI) calc'd for $C_{30}H_{42}F_3N_6O_3$ [M + H]⁺: 591, found 591; ¹H NMR (300 MHz, DMSO-$d_6$): δ 11.17 (br s, 1H), 8.35-8.23 (s, 1H), 7.85-7.53 (m, 4H), 7.12 (m, 1H), 6.61 (m, 1H), 3.77-3.68 (m, 2H), 3.45 (m, 1H), 3.06-2.73 (m, 2H), 2.50 (m, 2H), 2.46 (m, 1H), 1.86 (m, 4H), 1.39 (s, 9H), 1.09 (s, 9H), 0.54 (t, J = 7.2 Hz, 3H). |
| 2-37 | 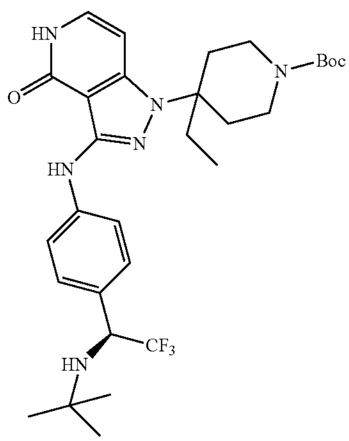 [SMILES: CCC1(n2nc(Nc3ccc([C@H](NC(C)(C)C)C(F)(F)F)cc3)c3c(=O)[nH]ccc32)CCN(C(=O)OC(C)(C)C)CC1] | (S or R)-tert-butyl 4-(3-(4-(1-(tert-butylamino)-2,2,2-trifluoroethyl)phenylamino)-4-oxo-4,5-dihydropyrazolo [4,3-c]pyridin-1-yl)-4-ethylpiperidine-1-carboxylate (Peak B, separated by HPLC, using ChiralpakAD-H column, eluting with 90% EtOH in hexanes, retention time: 18.0 minutes.) | LRMS (ESI) calc'd for $C_{30}H_{42}F_3N_6O_3$ [M + H]⁺: 591, found 591; ¹H NMR (300 MHz, DMSO-$d_6$): δ 11.17 (br s, 1H), 8.35-8.23 (s, 1H), 7.85-7.53 (m, 4H), 7.12 (m, 1H), 6.61 (m, 1H), 3.77-3.68 (m, 2H), 3.45 (m, 1H), 3.06-2.73 (m, 2H), 2.50 (m, 2H), 2.46 (m, 1H), 1.86 (m, 4H), 1.39 (s, 9H), 1.09 (s, 9H), 0.54 (t, J = 7.2 Hz, 3H). |
| 2-38 | 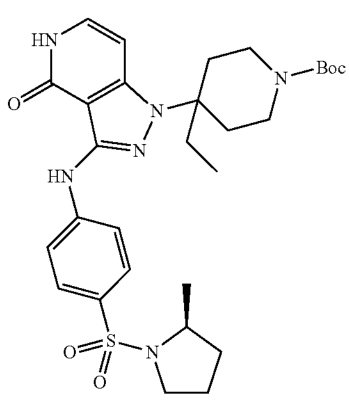 [SMILES: CCC1(n2nc(Nc3ccc(S(=O)(=O)N4CCC[C@@H]4C)cc3)c3c(=O)[nH]ccc32)CCN(C(=O)OC(C)(C)C)CC1] | (S or R)-tert-butyl 4-ethyl-4-(3-(4-(2-methylpyrrolidin-1-ylsulfonyl)phenyl amino)-4-oxo-4,5-dihydropyrazolo[4,3-c]pyridin-1-yl) piperidine-1-carboxylate | LRMS (ESI) calc'd for $C_{29}H_{41}N_6O_5$ S [M + H]⁺: 585, found 585; ¹H NMR (300 MHz, DMSO-$d_6$): δ 11.26 (br s, 1H), 8.62 (s, 1H), 7.81 (m, 2H), 7.72 (m, 2H), 7.14 (m, 1H), 6.64 (m, 1H), 3.74 (m, 2H), 3.71-3.59 (m, 1H), 3.09 (m, 3H), 2.60 (m, 2H), 1.89 (m, 4H), 1.75-1.61 (m, 2H), 1.40 (m, 2H), 1.39 (s, 9H), 1.23 (m, 4H), 0.53 (t, J = 6.3 Hz, 3H). $[α]_D^{20}$ = −31.2 (c = 0.18, DMSO at 589 nM) |

TABLE 5-continued

| Example | Structure | Compound Name | LRMS and/or ¹H NMR |
|---|---|---|---|
| 2-39 | 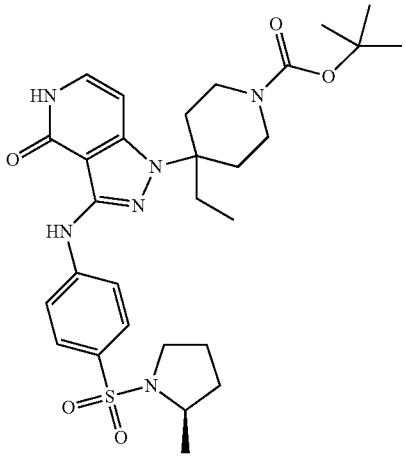 [SMILES: CCC1(n2nc(Nc3ccc(S(=O)(=O)N4CCC[C@H]4C)cc3)c3c(=O)[nH]ccc32)CCN(C(=O)OC(C)(C)C)CC1] | (R or S)-tert-butyl 4-ethyl-4-(3-(4-(2-methylpyrrolidin-1-ylsulfonyl)phenyl amino)-4-oxo-4,5-dihydropyrazolo[4,3-c]pyridin-1-yl) piperidine-1-carboxylate | LRMS (ESI) calc'd for $C_{29}H_{41}N_6O_5S$ [M + H]⁺: 585, found 585; ¹H NMR (300 MHz, DMSO-$d_6$): δ 11.26 (br s, 1H), 8.62 (s, 1H), 7.81 (m, 2H), 7.72 (m, 2H), 7.14 (m, 1H), 6.64 (m, 1H), 3.74 (m, 2H), 3.71-3.59 (m, 1H), 3.09 (m, 3H), 2.60 (m, 2H), 1.89 (m, 4H), 1.75-1.61 (m, 2H), 1.40 (m, 2H), 1.39 (s, 9H), 1.23 (m, 4H), 0.53 (t, J = 6.3 Hz, 3H). $[\alpha]_D^{20} = -31.2$ (c = 0.18, DMSO at 589 nM) |
| 2-40 | 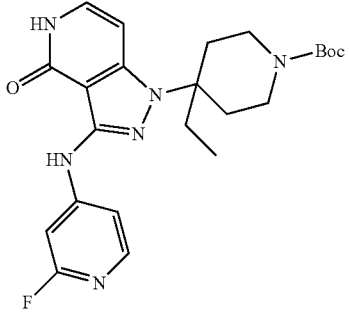 [SMILES: CCC1(n2nc(Nc3ccnc(F)c3)c3c(=O)[nH]ccc32)CCN(C(=O)OC(C)(C)C)CC1] | tert-butyl 4-ethyl-4-(3-(2-fluoropyridin-4-ylamino)-4-oxo-4,5-dihydropyrazolo[4,3-c]pyridin-1-yl) piperidine-1-carboxylate | LRMS (ESI) calc'd for $C_{23}H_{30}FN_6O_3$ [M + H]⁺: 457, found 457; ¹H NMR (300 MHz, DMSO-$d_6$): δ 11.25 (br s, 1H), 8.96 (s, 1H), 7.96 (d, J = 6.0 Hz, 1H), 7.48 (m, 1H), 7.37 (s, 1H), 7.15 (m, 1H), 6.66 (m, 1H), 3.72 (m, 2H), 3.05 (m, 2H), 2.51 (m, 2H), 1.91 (m, 4H), 1.39 (s, 9H), 0.53 (t, J = 6.3 Hz, 3H). |
| 2-41 | 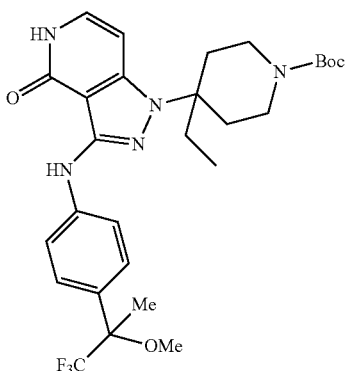 | tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate (derived from I-6A) | LRMS (ESI) calc'd for $C_{28}H_{37}F_3N_5O_4$ [M + Na]⁺: 586, found 586; ¹H NMR (500 MHz, DMSO-$d_6$): δ 11.23 (d, J = 5.5 Hz, 1H), 8.29 (s, 1H), 7.71 (d, J = 8.5 Hz, 2H), 7.44 (d, J = 8.0 Hz, 2H), 7.15 (t, J = 7.0 Hz, 1H), 6.64 (d, J = 7.5 Hz, 1H), 3.77 (d, J = 13.5 Hz, 2H), 3.16 (s, 3H), 3.07 (br s, 2H), 2.63 (d, J = 14.0 Hz, 2H), 1.90 (m, 4H), 1.77 (s, 3H), 1.42 (s, 9H), 0.56 (t, J = 7.5 Hz, 3H). |
| 2-42 | 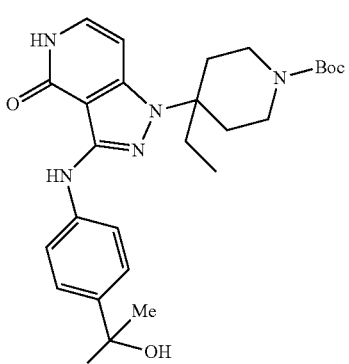 | tert-butyl 4-ethyl-4-(4-oxo-3-((4-(1,1,1-trifluoro-2-hydroxypropan-2-yl)phenyl)amino)-4,5-dihydro-1H-pyrazolo[4,3-c] pyridin-1-yl) piperidine-1-carboxylate (derived from I-5A) | LRMS (ESI) calc'd for $C_{27}H_{35}F_3N_5O_4$ [M + H]⁺: 550, found 550; ¹H NMR (500 MHz, DMSO-$d_6$): δ 11.22 (d, J = 6.0 Hz, 1H), 8.21 (s, 1H), 7.64 (d, J = 9.0 Hz, 2H), 7.52 (d, J = 9.0 Hz, 2H), 7.14 (t, J = 6.7 Hz, 1H), 6.64 (d, J = 7.5 Hz, 1H), 6.45 (s, 1H), 3.77 (d, J = 13.5 Hz, 2H), 3.08 (br s, 2H), 2.63 (d, J = 14.5 Hz, 2H), 1.90 (m, 4H), 1.69 (s, 3H), 1.42 (s, 9H), 0.56 (t, J = 7.5 Hz, 3H). |

TABLE 5-continued

| Example | Structure | Compound Name | LRMS and/or ¹H NMR |
|---|---|---|---|
| 2-43 | 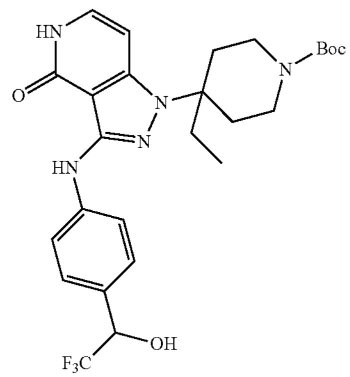 [SMILES: CCC1(n2nc(Nc3ccc(C(O)C(F)(F)F)cc3)c3c(=O)[nH]ccc32)CCN(C(=O)OC(C)(C)C)CC1] | tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl) piperidine-1-carboxylate (derived from I-4A) | LRMS (ESI) calc'd for $C_{26}H_{33}F_3N_5O_4$ [M + H]⁺: 536, found 536; ¹H NMR (500 MHz, DMSO-$d_6$): δ 11.22 (d, J = 6.0 Hz, 1H), 8.23 (s, 1H), 7.65 (d, J = 8.5 Hz, 2H), 7.42 (d, J = 8.5 Hz, 2H), 7.14 (t, J = 6.5 Hz, 1H), 6.70 (d, J = 5.5 Hz, 1H), 6.64 (d, J = 7.5 Hz, 1H), 5.04 (pentet, J = 7.1 Hz, 1H), 3.77 (d, J = 13.5 Hz, 2H), 3.08 (br s, 2H), 2.62 (d, J = 14.5 Hz, 2H), 1.90 (m, 4H), 1.42 (s, 9H), 0.56 (t, J = 7.5 Hz, 3H). |
| 2-44 | 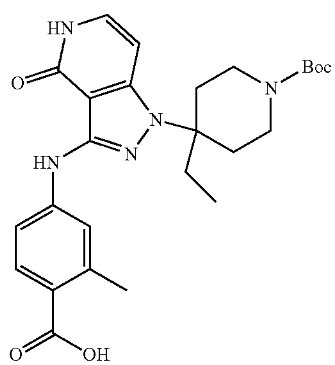 [SMILES: CCC1(n2nc(Nc3ccc(C(=O)O)c(C)c3)c3c(=O)[nH]ccc32)CCN(C(=O)OC(C)(C)C)CC1] | 4-((1-(1-(tert-butoxycarbonyl)-4-ethylpiperidin-4-yl)-4-oxo-4,5-dihydro-1H-pyrazolo[4,3-c] pyridin-3-yl)amino)-2-methylbenzoic acid | LRMS (ESI) calc'd for $C_{26}H_{34}N_5O_5$ [M + H]⁺: 496, found 496; ¹H NMR (400 MHz, DMSO-$d_6$): δ 12.29 (br s, 1H), 11.24 (m, 1H), 8.38 (s, 1H), 7.86 (m, 1H), 7.50 (m, 2H), 7.14 (m, 1H), 6.63 (d, J = 10.0 Hz, 1H), 3.76 (m, 2H), 3.08 (m, 2H), 2.52 (m, 2H), 2.48 (s, 3H), 1.91-1.82 (m, 4H), 1.39 (s, 9H), 0.56 (t, J = 9.6 Hz, 3H). |

Example 3-1 tert-butyl-4-ethyl-4-(3-((3-methyl-4-(2-oxomorpholine-4-carbonyl)phenyl)amino)-4-oxo-4,5-dihydro-1H-pyrazolo[4,3-c]pyridin-1-yl)piperidine-1-carboxylate

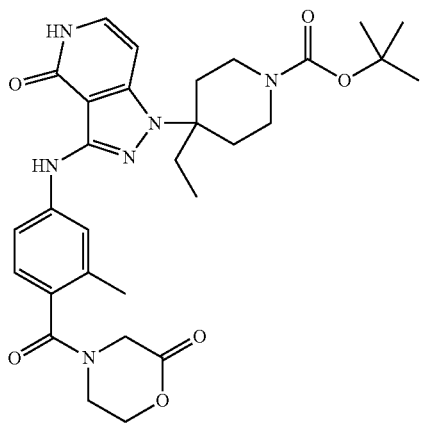 [SMILES: CCC1(n2nc(Nc3ccc(C(=O)N4CCOC(=O)C4)c(C)c3)c3c(=O)[nH]ccc32)CCN(C(=O)OC(C)(C)C)CC1]

Morpholin-2-one (29 mg, 0.28 mmol), 4-methylmorpholine (29 mg, 0.28 mmol) and ((1H-benzo[d][1,2,3]triazol-1-yl)oxy)tri(pyrrolidin-1-yl)phosphonium (PyBop) (0.10 g, 0.28 mmol) were added to a stirred solution of 4-((1-(1-(tert-butoxycarbonyl)-4-ethylpiperidin-4-yl)-4-oxo-4,5-dihydro-1H-pyrazolo[4,3-c]pyridin-3-yl)amino)-2-methylbenzoic acid (70 mg, 0.14 mmol) in DCM (10 mL) at ambient temperature. The reaction mixture was stirred for 12 hours at ambient temperature, then quenched with water (5 mL) and extracted with EtOAc (×2). The combined organic layers were washed with brine (×2), dried over anhydrous $Na_2SO_4$, filtered, and the filtrate was concentrated in vacuo. The product was purified by Prep-HPLC using an Xbridge C18 column, eluting with acetonitrile in water (containing 0.05% $NH_4HCO_3$) using a acetonitrile gradient of 20% acetonitrile hold for 6 minutes, then hold at 54% for 2 minutes, down to 20% in 2 minutes. The collected fractions were combined and concentrated in vacuo to afford the title compound as a solid. LRMS (ESI) calc'd for $C_{30}H_{39}N_6O_6$ [M+H]⁺: 579, found 579; ¹H NMR (400 MHz, DMSO-$d_6$): δ 11.13 (br s, 1H), 8.17 (s, 1H), 7.45 (m, 2H), 7.07 (m, 2H), 6.55 (d, J=10 Hz, 1H), 4.33 (m, 3H), 3.69 (m, 3H), 3.39 (m, 2H), 3.12-2.94 (m, 2H), 2.44 (m, 2H), 2.15 (s, 3H), 1.82 (m, 4H), 1.32 (s, 9H), 0.47 (t, J=9.6 Hz, 3H).

The following examples in Table 6 were prepared in analogy to Example 3 above, using HATU and diisopropylethylamine as base in DMF.

TABLE 6

| Example | Structure | Compound Name | LRMS and/or ¹H NMR |
|---|---|---|---|
| 3-2 | 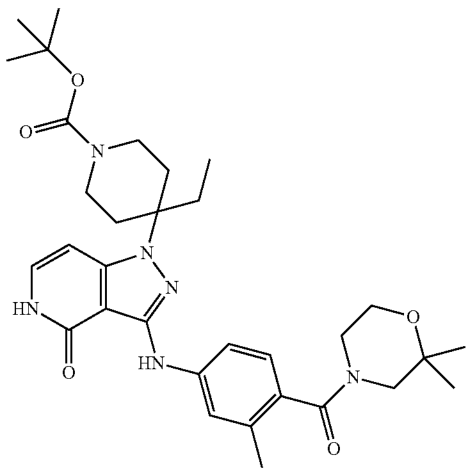 [SMILES: CCC1(n2nc(Nc3ccc(C(=O)N4CCOC(C)(C)C4)c(C)c3)c3c(=O)[nH]ccc32)CCN(C(=O)OC(C)(C)C)CC1] | tert-butyl 4-[3-({4-[(2,2-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate | LRMS (ESI) calc'd for $C_{32}H_{45}N_6O_5$ [M + H]⁺: 593 found 593. ¹H NMR (500 MHz, DMSO-$d_6$): δ 11.17 (d, J = 5.7 Hz, 1H), 8.16 (s, 1H), 7.49 (m, 2H), 7.09 (m, 2H), 6.59 (d, J = 7.4 Hz, 1H), 3.73 (d, J = 12.9 Hz, 2H), 3.63-3.42 (m, 2H), 3.33 (d, J = 2.0 Hz, 2H), 3.17-2.95 (m, 2H), 2.57 (d, J = 14.0 Hz, 1H), 2.48 (m, 3H), 2.20 (s, 3H), 1.85 (m, 4H), 1.37 (s, 9H), 1.18 (br s, 3H), 1.02 (br s, 3H), 0.52 (t, J = 7.4 Hz, 3H). |
| 3-3 | 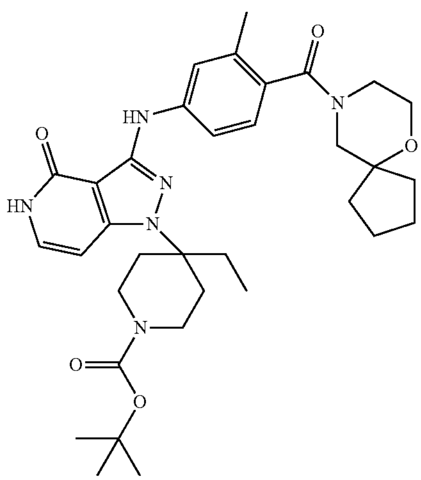 [SMILES: CCC1(n2nc(Nc3ccc(C(=O)N4CCOC5(CCCC5)C4)c(C)c3)c3c(=O)[nH]ccc32)CCN(C(=O)OC(C)(C)C)CC1] | tert-butyl 4-ethyl-4-(3-{[3-methyl-4-(6-oxa-9-azaspiro[4.5] dec-9-ylcarbonyl) phenyl]amino}-4-oxo-4,5-dihydro-1H-pyrazolo[4,3-c]pyridin-1-yl) piperidine-1-carboxylate | LRMS (ESI) calc'd for $C_{34}H_{47}N_6O_5$ [M + H]⁺: 619 found 619. ¹H NMR (500 MHz, DMSO-$d_6$): δ 11.17 (d, J = 5.5 Hz, 1H), 8.18 (s, 1H), 7.49 (m, 2H), 7.10 (t, J = 6.4 Hz, 1H), 7.06 (d, J = 8.2 Hz, 1H), 6.59 (d, J = 7.3 Hz, 1H), 3.73 (d, J = 15.8 Hz, 2H), 3.66-3.44 (m, 2H), 3.33 (s, 2H), 3.19-2.95 (m, 2H), 2.57 (d, J = 14.4 Hz, 1H), 2.48 (m, 3H), 2.20 (s, 3H), 1.85 (m, 4H), 1.64 (s, 6H), 1.36 (s, 9H), 0.52 (t, J = 7.4 Hz, 3H). |
| 3-4 | 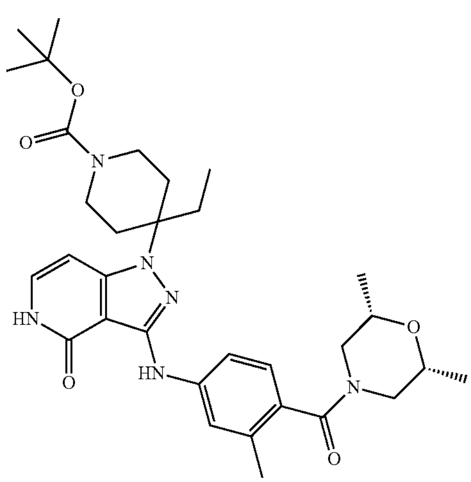 [SMILES: CCC1(n2nc(Nc3ccc(C(=O)N4C[C@@H](C)O[C@@H](C)C4)c(C)c3)c3c(=O)[nH]ccc32)CCN(C(=O)OC(C)(C)C)CC1] | tert-butyl 4-{3-[(4-{[(2R,6S)-2,6-dimethylmorpholin-4-yl]carbonyl}-3-methylphenyl)amino]-4-oxo-4,5-dihydro-1H-pyrazolo[4,3-c]pyridin-1-yl}-4-ethylpiperidine-1-carboxylate | LRMS (ESI) calc'd for $C_{32}H_{45}N_6O_5$ [M + H]⁺: 593 found 593. |

TABLE 6-continued

| Example | Structure | Compound Name | LRMS and/or $^1$H NMR |
|---|---|---|---|
| 3-5 | 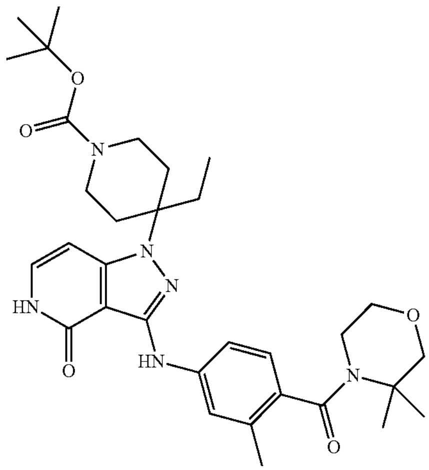 [SMILES: CCC1(n2nc(Nc3ccc(C(=O)N4CCOCC4(C)C)c(C)c3)c3c(=O)[nH]ccc32)CCN(C(=O)OC(C)(C)C)CC1] | tert-butyl 4-[3-({4-[(3,3-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate | LRMS (ESI) calc'd for $C_{32}H_{45}N_6O_5$ [M + H]$^+$: 593 found 593; $^1$H NMR (500 MHz, DMSO-d$_6$): δ 11.17 (d, J = 5.8 Hz, 1H), 8.16 (s, 1H), 7.46 (m, 2H), 7.10 (t, J = 6.6 Hz, 1H), 7.05 (d, J = 8.2 Hz, 1H), 6.59 (d, J = 7.5 Hz, 1H), 3.73 (d, J = 13.1 Hz, 2H), 3.56 (m, 2H), 3.13 (s, 2H), 2.98 (s, 1H), 2.20 (s, 3H), 1.79-1.87 (m, 4H), 1.41 (s, 6H), 1.37 (s, 9H), 0.52 (t, J = 7.3 Hz, 3H). |
| 3-6 | 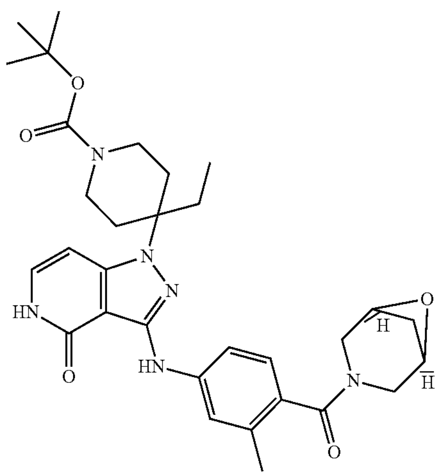 | tert-butyl 4-ethyl-4-[3-({3-methyl-4-[(1R,5S)-6-oxa-3-azabicyclo[3.1.1]hept-3-ylcarbonyl]phenyl}amino)-4-oxo-4,5-dihydro-1H-pyrazolo[4,3-c]pyridin-1-yl]piperidine-1-carboxylate | LRMS (ESI) calc'd for $C_{31}H_{41}N_6O_5$ [M + H]$^+$: 577, found 577; $^1$H NMR (600 MHz, DMSO-d$_6$): δ 11.15 (d, J = 5.8 Hz, 1H), 8.14 (s, 1H), 7.46 (m, 2H), 7.12 (d, J = 8.1 Hz, 1H), 7.08 (dd, J = 7.5, 5.8 Hz, 1H), 6.57 (d, J = 7.5 Hz, 1H), 4.61 (s, 1H), 4.41 (s, 1H), 3.89 (d, J = 13.7 Hz, 1H), 3.71 (d, J = 13.1 Hz, 2H), 3.52 (d, J = 13.7 Hz, 1H), 3.43 (d, J = 12.4 Hz, 1H), 3.03 (m, 2H), 2.55 (d, J = 15.2 Hz, 2H), 2.17 (s, 3H), 1.77-1.87 (m, 5H), 1.35 (s, 9H), 1.20-1.23 (m, 2H), 0.50 (t, J = 7.4 Hz, 3H). |
| 3-7 | 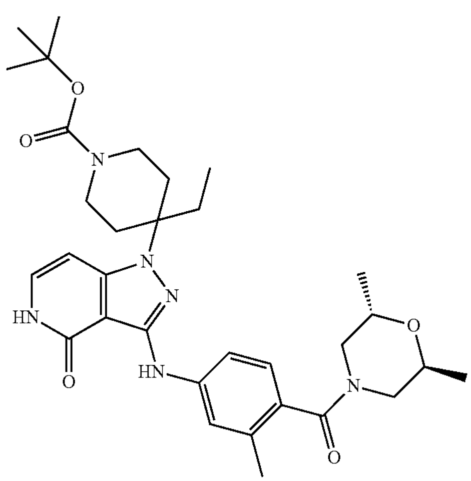 [SMILES: CCC1(n2nc(Nc3ccc(C(=O)N4C[C@H](C)O[C@@H](C)C4)c(C)c3)c3c(=O)[nH]ccc32)CCN(C(=O)OC(C)(C)C)CC1] | tert-butyl 4-{3-[(4-{[(2S,6S)-2,6-dimethylmorpholin-4-yl]carbonyl}-3-methylphenyl)amino]-4-oxo-4,5-dihydro-1H-pyrazolo[4,3-c] pyridin-1-yl}-4-ethylpiperidine-1-carboxylate | LRMS (ESI) calc'd for $C_{32}H_{45}N_6O_5$ [M + H]$^+$: 593, found 593; $^1$H NMR (500 MHz, DMSO-d$_6$): δ 11.17 (d, J = 5.8 Hz, 1H), 8.18 (s, 1H), 7.47 (m, 2H), 7.06-7.11 (m, 2H), 6.59 (d, J = 7.5 Hz, 1H), 3.97 (s, 1H), 3.80 (br s, 1H), 3.73 (d, J = 13.2 Hz, 2H), 3.32 (m, 1H), 3.00 (d, J = 26.3 Hz, 1H), 2.55 (m, 2H), 2.19 (s, 3H), 1.84 (m, 4H), 1.37 (s, 9H), 1.14 (s, 3H), 0.97 (s, 3H), 0.52 (t, J = 7.3 Hz, 3H). |

TABLE 6-continued

| Example | Structure | Compound Name | LRMS and/or ¹H NMR |
|---|---|---|---|
| 3-8 | 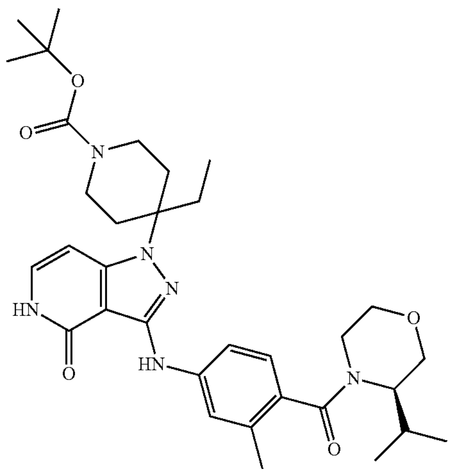 [SMILES: CCC1(n2nc(Nc3ccc(C(=O)N4CCOC[C@H]4C(C)C)c(C)c3)c3c(=O)[nH]ccc32)CCN(C(=O)OC(C)(C)C)CC1] | tert-butyl 4-ethyl-4-{3-[(3-methyl-4-{[(3R)-3-(1-methylethyl)morpholin-4-yl]carbonyl}phenyl)amino]-4-oxo-4,5-dihydro-1H-pyrazolo[4,3-c] pyridin-1-yl} piperidine-1-carboxylate | LRMS (ESI) calc'd for $C_{33}H_{47}N_6O_5$ [M + H]$^+$: 607, found 607. |
| 3-9 | 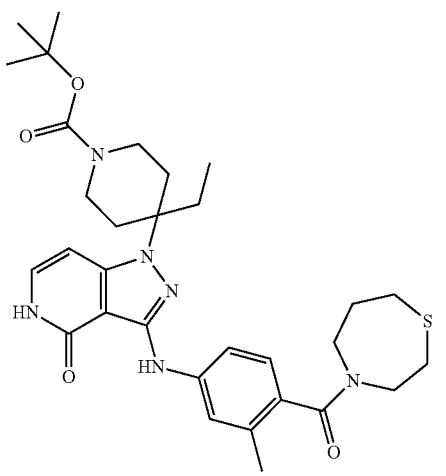 [SMILES: CCC1(n2nc(Nc3ccc(C(=O)N4CCCSCC4)c(C)c3)c3c(=O)[nH]ccc32)CCN(C(=O)OC(C)(C)C)CC1] | tert-butyl 4-ethyl-4-(3-{[3-methyl-4-(1,4-thiazepan-4-ylcarbonyl)phenyl]amino}-4-oxo-4,5-dihydro-1H-pyrazolo[4,3-c] pyridin-1-yl) piperidine-1-carboxylate | LRMS (ESI) calc'd for $C_{31}H_{43}N_6O_4S$ [M + H]$^+$: 595, found 595. |
| 3-10 | 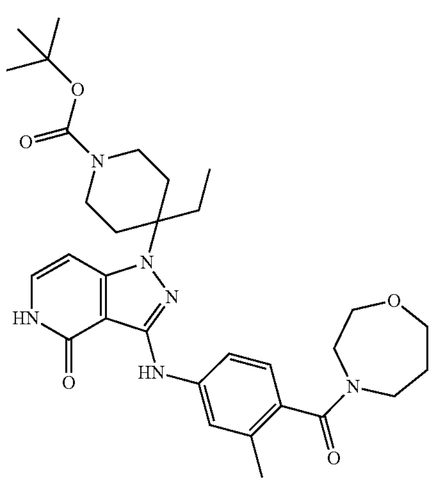 [SMILES: CCC1(n2nc(Nc3ccc(C(=O)N4CCCOCC4)c(C)c3)c3c(=O)[nH]ccc32)CCN(C(=O)OC(C)(C)C)CC1] | tert-butyl 4-ethyl-4-(3-{[3-methyl-4-(1,4-oxazepan-4-ylcarbonyl)phenyl]amino}-4-oxo-4,5-dihydro-1H-pyrazolo[4,3-c] pyridin-1-yl) piperidine-1-carboxylate | LRMS (ESI) calc'd for $C_{31}H_{43}N_6O_5$ [M + H]$^+$: 579, found 579. |

TABLE 6-continued

| Example | Structure | Compound Name | LRMS and/or $^1$H NMR |
|---|---|---|---|
| 3-11 | 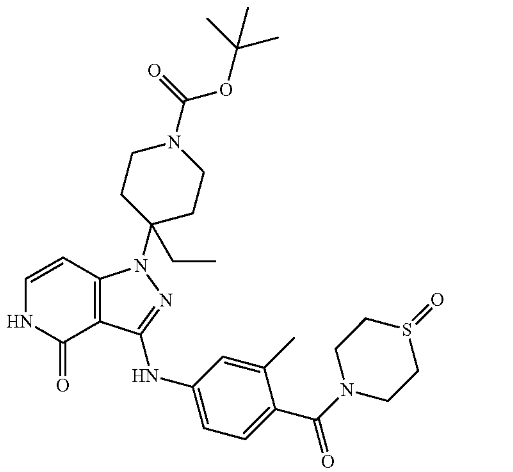 [SMILES: CCC1(n2nc(Nc3ccc(C(=O)N4CCS(=O)CC4)c(C)c3)c3c(=O)[nH]ccc32)CCN(C(=O)OC(C)(C)C)CC1] | tert-butyl 4-ethyl-4-[3-({3-methyl-4-[(1-oxidothiomorpholin-4-yl)carbonyl]phenyl}amino)-4-oxo-4,5-dihydro-1H-pyrazolo[4,3-c]pyridin-1-yl]piperidine-1-carboxylate | LRMS (ESI) calc'd for $C_{30}H_{41}N_6O_5S$ [M + H]$^+$: 597, found 597; $^1$H NMR (600 MHz, DMSO-$d_6$): δ 11.15 (s, 1H), 8.17 (s, 1H), 7.47 (d, J = 11.5 Hz, 2H), 7.15 (s, 1H), 7.08 (d, J = 7.5 Hz, 1H), 6.57 (d, J = 7.5 Hz, 1H), 4.34 (br s, 1H), 3.71 (d, J = 14.0 Hz, 3H), 3.38 (br s, 1H), 3.01 (br s, 3H), 2.90 (br s, 2H), 2.81 (br s, 2H), 2.63 (br s, 1H), 2.55 (d, J = 14.2 Hz, 2H), 2.17 (s, 3H), 1.77-1.86 (m, 4H), 1.35 (s, 8H), 0.50 (t, J = 7.4 Hz, 3H). |
| 3-12 | 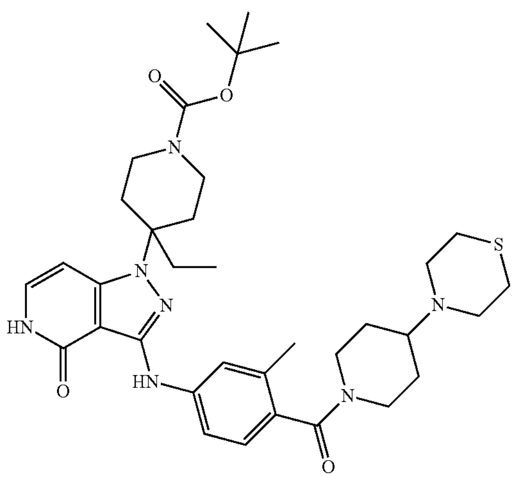 [SMILES: CCC1(n2nc(Nc3ccc(C(=O)N4CCC(N5CCSCC5)CC4)c(C)c3)c3c(=O)[nH]ccc32)CCN(C(=O)OC(C)(C)C)CC1] | tert-butyl 4-ethyl-4-[3-({3-methyl-4-[(4-thiomorpholin-4-ylpiperidin-1-yl)carbonyl]phenyl} amino)-4-oxo-4,5-dihydro-1H-pyrazolo[4,3-c]pyridin-1-yl] piperidine-1-carboxylate | LRMS (ESI) calc'd for $C_{35}H_{50}N_7O_4S$ [M + H]$^+$: 664, found 664; $^1$H NMR (600 MHz, DMSO-$d_6$): δ 11.14 (d, J = 5.7 Hz, 1H), 8.14 (s, 1H), 7.44 (s, 2H), 7.08 (t, J = 6.3 Hz, 1H), 6.57 (d, J = 7.5 Hz, 1H), 4.54 (br s, 1H), 3.71 (d, J = 13.1 Hz, 2H), 3.01 (br s, 2H), 2.90 (br s, 1H), 2.71 (s, 4H), 2.63 (br s, 1H), 2.46 (t, J = 2.2 Hz, 11H), 2.14 (br s, 3H), 1.77-1.86 (m, 4H), 1.71 (br s, 1H), 1.54 (br s, 1H), 1.35 (s, 9H), 0.50 (t, J = 7.4 Hz, 3H). |
| 3-13 | 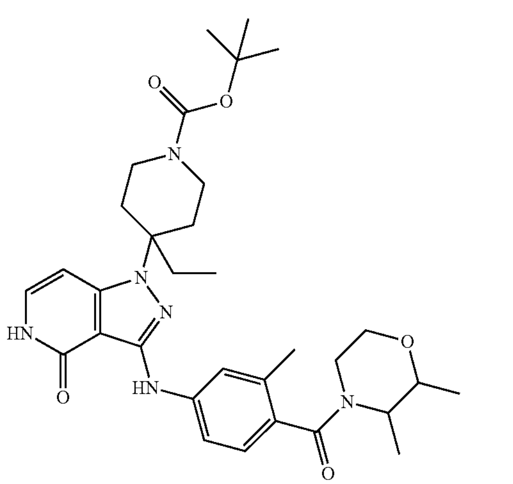 [SMILES: CCC1(n2nc(Nc3ccc(C(=O)N4CCOC(C)C4C)c(C)c3)c3c(=O)[nH]ccc32)CCN(C(=O)OC(C)(C)C)CC1] | tert-butyl 4-[3-({4-[(2,3-dimethylmorpholin-4-yl)carbonyl]-3-methylphenyl}amino)-4-oxo-4,5-dihydro-1H-pyrazolo[4,3-c] pyridin-1-yl]-4-ethylpiperidine-1-carboxylate (Peak 2, separated by mass triggered reverse phase HPLC (ACN/water with 0.1% NH$_4$OH modifier) then was separated by SFC using Phenomenex Lux-4 column, eluting with 40% methanol +0.25% dimethyl ethyl amine in CO$_2$, retention time peak B: 10.2 minutes.) | LRMS (ESI) calc'd for $C_{32}H_{45}N_6O_5$ [M + H]$^+$: 593, found 593. |

TABLE 6-continued

| Example | Structure | Compound Name | LRMS and/or $^1$H NMR |
|---|---|---|---|
| 3-14 | 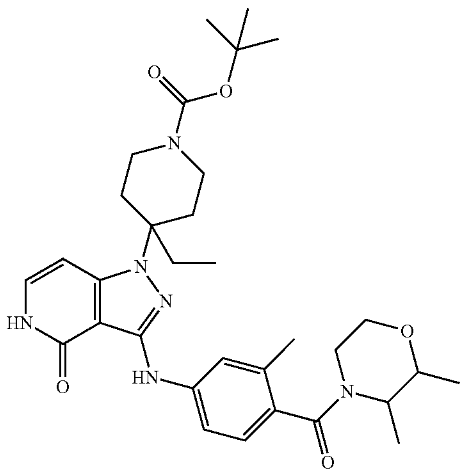 [SMILES: CCC1(n2nc(Nc3ccc(C(=O)N4CCOC(C)C4C)c(C)c3)c3c(=O)[nH]ccc32)CCN(C(=O)OC(C)(C)C)CC1] | tert-butyl 4-[3-({4-[(2,3-dimethylmorpholin-4-yl)carbonyl]-3-methylphenyl}amino)-4-oxo-4,5-dihydro-1H-pyrazolo[4,3-c] pyridin-1-yl]-4-ethylpiperidine-1-carboxylate (Peak 1, separated by mass triggered reverse phase HPLC (ACN/water with 0.1% NH$_4$OH modifier) then was separated by SFC using Phenomenex Lux-4 column, eluting with 40% methanol +0.25% dimethyl ethyl amine in CO$_2$, retention time peak A: 8.2 minutes.) | LRMS (ESI) calc'd for C$_{32}$H$_{45}$N$_6$O$_5$ [M + H]$^+$: 593, found 593. |
| 3-15 | 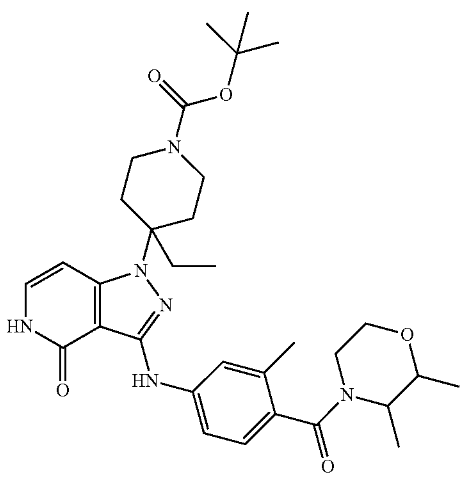 [SMILES: CCC1(n2nc(Nc3ccc(C(=O)N4CCOC(C)C4C)c(C)c3)c3c(=O)[nH]ccc32)CCN(C(=O)OC(C)(C)C)CC1] | tert-butyl 4-[3-({4-[(2,3-dimethylmorpholin-4-yl)carbonyl]-3-methylphenyl}amino)-4-oxo-4,5-dihydro-1H-pyrazolo[4,3-c] pyridin-1-yl]-4-ethylpiperidine-1-carboxylate (Peak 1, separated by mass triggered reverse phase HPLC (ACN/water with 0.1% NH$_4$OH modifier) then was separated by SFC using Phenomenex Lux-4 column, eluting with 40% methanol +0.25% dimethyl ethyl amine in CO$_2$, retention time peak B: 9.8 minutes.) | LRMS (ESI) calc'd for C$_{32}$H$_{45}$N$_6$O$_5$ [M + H]$^+$: 593, found 593. |
| 3-16 | 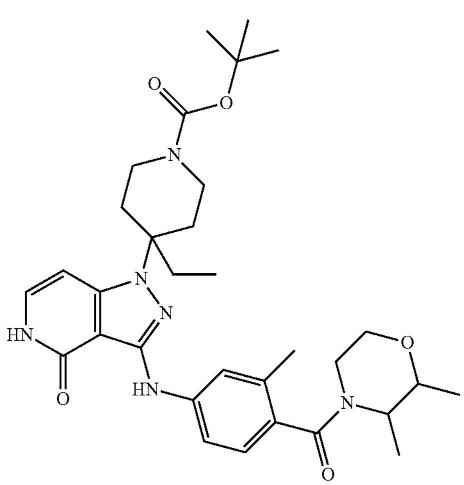 [SMILES: CCC1(n2nc(Nc3ccc(C(=O)N4CCOC(C)C4C)c(C)c3)c3c(=O)[nH]ccc32)CCN(C(=O)OC(C)(C)C)CC1] | tert-butyl 4-[3-({4-[(2,3-dimethylmorpholin-4-yl)carbonyl]-3-methylphenyl}amino)-4-oxo-4,5-dihydro-1H-pyrazolo[4,3-c] pyridin-1-yl]-4-ethylpiperidine-1-carboxylate (Peak 2, separated by mass triggered reverse phase HPLC (ACN/water with 0.1% NH$_4$OH modifier) then was separated by SFC using Phenomenex Lux-4 column, eluting with 40% methanol +0.25% dimethyl ethyl amine in CO$_2$, retention time peak A: 8.4 minutes.) | LRMS (ESI) calc'd for C$_{32}$H$_{45}$N$_6$O$_5$ [M + H]$^+$: 593, found 593. |

TABLE 6-continued

| Example | Structure | Compound Name | LRMS and/or $^1$H NMR |
|---|---|---|---|
| 3-17 | 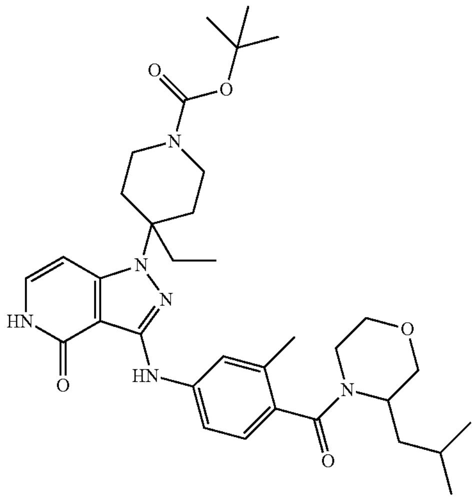 [SMILES: CCC1(n2nc(Nc3ccc(C(=O)N4CCOCC4CC(C)C)c(C)c3)c3c(=O)[nH]ccc32)CCN(C(=O)OC(C)(C)C)CC1] | tert-butyl 4-ethyl-4-{3-[(3-methyl-4-{[3-(2S or 2R-methyl propyl) morpholin-4-yl] carbonyl} phenyl) amino]-4-oxo-4,5-dihydro-1H-pyrazolo [4,3-c]pyridin-1-yl} piperidine-1-carboxylate Peak A separated by SFC using Phenomenex Lux-4 column, eluting with 35% methanol +0.25% dimethyl ethyl amine in $CO_2$, retention time: 7.2 minutes.) | LRMS (ESI) calc'd for $C_{34}H_{49}N_6O_5$ [M + H]$^+$: 621, found 621. |
| 3-18 | 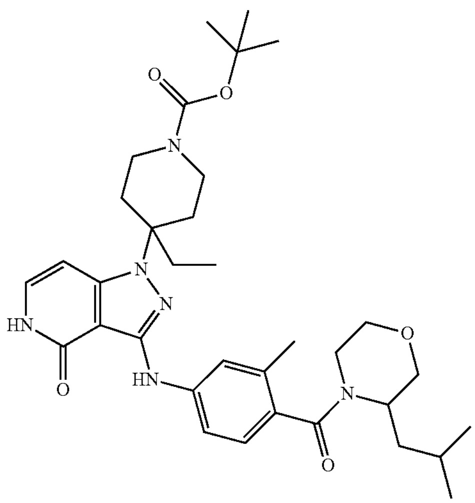 [SMILES: CCC1(n2nc(Nc3ccc(C(=O)N4CCOCC4CC(C)C)c(C)c3)c3c(=O)[nH]ccc32)CCN(C(=O)OC(C)(C)C)CC1] | tert-butyl 4-ethyl-4-{3-[(3-methyl-4-{[3-(2S or 2R-methylpropyl)morpholin-4-yl]carbonyl} phenyl) amino]-4-oxo-4,5-dihydro-1H-pyrazolo[4,3-c] pyridin-1-yl} piperidine-1-carboxylate Peak B separated by SFC using Phenomenex Lux-4 column, eluting with 35% methanol +0.25% dimethyl ethyl amine in $CO_2$, retention time: 8.1 minutes.) | LRMS (ESI) calc'd for $C_{34}H_{49}N_6O_5$ [M + H]$^+$: 621, found 621. |
| 3-19 | 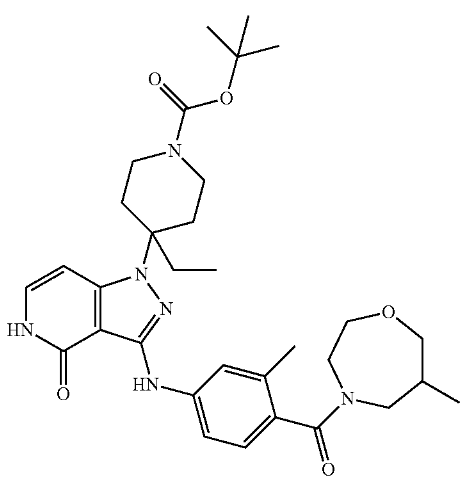 [SMILES: CCC1(n2nc(Nc3ccc(C(=O)N4CCOCC(C)C4)c(C)c3)c3c(=O)[nH]ccc32)CCN(C(=O)OC(C)(C)C)CC1] | tert-butyl 4-ethyl-4-[3-({3-methyl-4-[(6R or 6S-methyl-1,4-oxazepan-4-yl) carbonyl]phenyl} amino)-4-oxo-4,5-dihydro-1H-pyrazolo [4,3-c]pyridin-1-yl] piperidine-1-carboxylate (Peak A, separated by SFC, using AD-H column, eluting with 25% isopropanol (0.1% NPA) in $CO_2$, retention time: 5.3 minutes.) | LRMS (ESI) calc'd for $C_{32}H_{45}N_6O_5$ [M + H]$^+$: 593, found 493; $^1$H NMR (600 MHz, DMSO-d$_6$): δ 8.14 (d, J = 9.3 Hz, 1H), 7.41-7.47 (m, 2H), 7.05 (m, 2H), 6.57 (d, J = 7.5 Hz, 1H), 3.92 (d, J = 13.5 Hz, 1H), 3.67-3.78 (m, 4H), 3.60 (d, J = 12.5 Hz, 1H), 3.51 (m, 1H), 3.45 (m, 3H), 2.93-2.99 (m, 1H), 2.55 (d, J = 14.2 Hz, 2H), 2.16 (d, J = 3.2 Hz, 3H), 1.76-1.86 (m, 5H), 1.35 (s, 9H), 1.06 (t, J = 7.0 Hz, 1H), 0.84 (d, J = 6.9 Hz, 2H), 0.59 (d, J = 6.9 Hz, 2H), 0.50 (td, J = 7.3, 3.1 Hz, 3H). |

TABLE 6-continued

| Example | Structure | Compound Name | LRMS and/or $^1$H NMR |
|---|---|---|---|
| 3-20 | 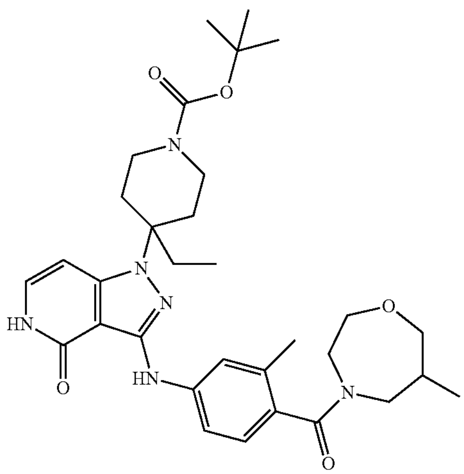 [SMILES: CCC1(n2nc(Nc3ccc(C(=O)N4CCOCC(C)C4)c(C)c3)c3c(=O)[nH]ccc32)CCN(C(=O)OC(C)(C)C)CC1] | tert-butyl 4-ethyl-4-[3-({3-methyl-4-[(6R or 6S-methyl-1,4-oxazepan-4-yl)carbonyl]phenyl}amino)-4-oxo-4,5-dihydro-1H-pyrazolo[4,3-c] pyridin-1-yl] piperidine-1-carboxylate (Peak B, separated by SFC, using AD-H column, eluting with 25% isopropanol (0.1% NPA) in $CO_2$, retention time: 5.8 minutes.) | LRMS (ESI) calc'd for $C_{32}H_{45}N_6O_5$ [M + H]$^+$: 593, found 493; $^1$H NMR (600 MHz, DMSO-$d_6$): δ 8.14 (d, J = 9.3 Hz, 1H), 7.41-7.47 (m, 2H), 7.05 (m, 2H), 6.57 (d, J = 7.5 Hz, 1H), 3.92 (d, J = 13.5 Hz, 1H), 3.67-3.78 (m, 4H), 3.60 (d, J = 12.5 Hz, 1H), 3.51 (m, 1H), 3.45 (m, 3H), 2.93-2.99 (m, 1H), 2.55 (d, J = 14.2 Hz, 2H), 2.16 (d, J = 3.2 Hz, 3H), 1.76-1.86 (m, 5H), 1.35 (s, 9H), 1.06 (t, J = 7.0 Hz, 1H), 0.84 (d, J = 6.9 Hz, 2H), 0.59 (d, J = 6.9 Hz, 2H), 0.50 (td, J = 7.3, 3.1 Hz, 3H). |
| 3-21 | 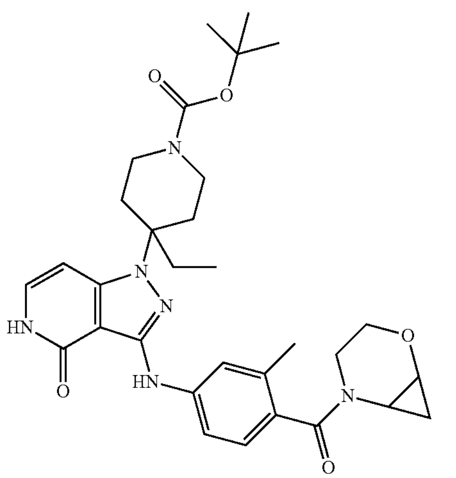 [SMILES: CCC1(n2nc(Nc3ccc(C(=O)N4CCOC5CC54)c(C)c3)c3c(=O)[nH]ccc32)CCN(C(=O)OC(C)(C)C)CC1] | tert-butyl 4-ethyl-4-(3-{[3-methyl-4-(2-oxa-5-azabicyclo [4.1.0]hept-5-ylcarbonyl)phenyl]amino}-4-oxo-4,5-dihydro-1H-pyrazolo [4,3-c]pyridin-1-yl) piperidine-1-carboxylate | LRMS (ESI) calc'd for $C_{31}H_{41}N_6O_5$ [M + H]$^+$: 577, found 577. |
| 3-22 | 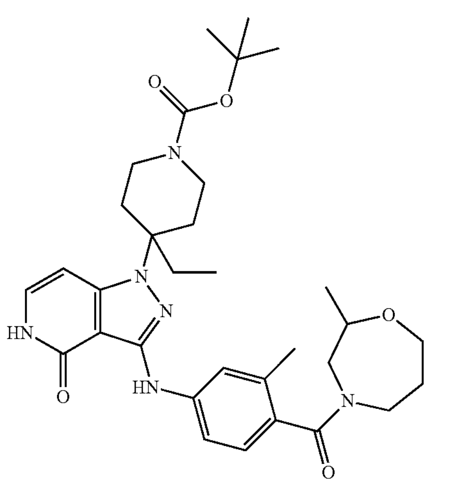 [SMILES: CCC1(n2nc(Nc3ccc(C(=O)N4CCCOC(C)C4)c(C)c3)c3c(=O)[nH]ccc32)CCN(C(=O)OC(C)(C)C)CC1] | tert-butyl 4-ethyl-4-[3-({3R or 3S-methyl-4-[(2-methyl-1,4-oxazepan-4-yl)carbonyl]phenyl} amino)-4-oxo-4,5-dihydro-1H-pyrazolo [4,3-c]pyridin-1-yl] piperidine-1-carboxylate (Peak A, separated by SFC, using AD-H column, eluting with 20% isopropanol (0.1% DEA) in $CO_2$, retention time: 17.8 minutes.) | LRMS (ESI) calc'd for $C_{32}H_{45}N_6O_5$ [M + H]$^+$: 593, found 593. |

TABLE 6-continued

| Example | Structure | Compound Name | LRMS and/or ¹H NMR |
|---|---|---|---|
| 3-23 | 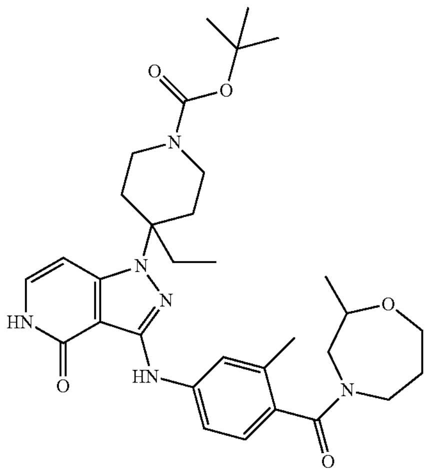 [SMILES: CCC1(n2nc(Nc3ccc(C(=O)N4CCCOC(C)C4)c(C)c3)c3c(=O)[nH]ccc32)CCN(C(=O)OC(C)(C)C)CC1] | tert-butyl 4-ethyl-4-[3-({3R or 3S-methyl-4-[(2-methyl-1,4-oxazepan-4-yl)carbonyl]phenyl}amino)-4-oxo-4,5-dihydro-1H-pyrazolo [4,3-c]pyridin-1-yl] piperidine-1-carboxylate (Peak B, separated by SFC, using AD-H column, eluting with 20% isopropanol (0.1% DEA) in $CO_2$, retention time: 20.5 minutes.) | LRMS (ESI) calc'd for $C_{32}H_{45}N_6O_5$ $[M + H]^+$: 593, found 593. |

BIOLOGICAL ASSAYS

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDEPEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL of 1.11× enzyme and 1.11× substrate in 1× assay buffer (Invitrogen kinase buffer # PV3189, 2 mM DTT, 0.05% BSA) were added to the wells and shaken and then preincubated for 30 minutes at room temperature to allow compound binding to equilibrate. After equilibration, 2 µL of 10×ATP in 1× assay buffer was added to initiate the kinase reaction and the plates were shaken and then incubated at room temperature for 120 minutes. At the end of the incubation, 20 µL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision (Xex=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final reaction conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

BIOLOGICAL DATA

Examples of the instant invention were evaluated in JAK1 and JAK2 in vitro binding assays as described above. The following table, Table 7, tabulates the JAK1 $IC_{50}$ values and JAK2 $IC_{50}$ values disclosed for the instant invention.

TABLE 7

| Example | JAK1 $IC_{50}$ (nM) | JAK2 $IC_{50}$ (nM) |
|---|---|---|
| 1-1 | 0.20 | 0.40 |
| 1-2 | 2.86 | 3.40 |
| 1-3 | 0.12 | 0.64 |
| 2-1 | 0.47 | 0.49 |
| 2-2 | 3.21 | 3.16 |
| 2-3 | 10.2 | 71.3 |
| 2-4 | 0.37 | 0.56 |
| 2-5 | 0.54 | 0.60 |
| 2-6 | 0.51 | 0.51 |
| 2-7 | 0.72 | 0.60 |
| 2-8 | 0.62 | 0.57 |
| 2-9 | 0.37 | 0.47 |
| 2-10 | 13.9 | 16.9 |
| 2-11 | 0.37 | 0.47 |
| 2-12 | 0.56 | 0.74 |
| 2-13 | 0.52 | 0.54 |
| 2-14 | 0.30 | 0.43 |
| 2-15 | 0.40 | 0.43 |
| 2-16 | 8.85 | 10.1 |
| 2-17 | 0.53 | 3.37 |
| 2-18 | 0.61 | 0.57 |
| 2-19 | 0.85 | 0.65 |
| 2-20 | 0.79 | 0.84 |
| 2-21 | 0.84 | 0.93 |
| 2-22 | 0.36 | 0.44 |
| 2-23 | 1.13 | 1.92 |

TABLE 7-continued

| Example | JAK1 IC$_{50}$ (nM) | JAK2 IC$_{50}$ (nM) |
|---|---|---|
| 2-24 | 0.47 | 0.84 |
| 2-25 | 1.73 | 2.80 |
| 2-26 | 1.19 | 1.44 |
| 2-27 | 0.84 | 0.93 |
| 2-28 | 0.54 | 0.51 |
| 2-29 | 1.79 | 2.72 |
| 2-30 | 0.29 | 0.36 |
| 2-31 | 2.74 | 2.70 |
| 2-32 | 2.19 | 2.21 |
| 2-33 | 0.73 | 1.06 |
| 2-34 | 2.50 | 2.50 |
| 2-35 | 2.82 | 3.55 |
| 2-36 | 8.43 | 13.0 |
| 2-37 | 6.59 | 7.69 |
| 2-38 | 2.38 | 2.78 |
| 2-39 | 2.13 | 2.79 |
| 2-40 | 0.38 | 5.24 |
| 2-41 | 4.40 | 6.87 |
| 2-42 | 1.65 | 4.62 |
| 2-43 | 0.90 | 2.91 |
| 2-44 | 0.23 | 2.10 |
| 3-1 | 0.25 | 0.80 |
| 3-2 | 0.61 | 0.75 |
| 3-3 | 0.99 | 1.53 |
| 3-4 | 1.09 | 1.17 |
| 3-5 | 0.73 | 1.21 |
| 3-6 | 0.30 | 0.43 |
| 3-7 | 0.52 | 0.63 |
| 3-8 | 0.93 | 1.01 |
| 3-9 | 0.79 | 1.05 |
| 3-10 | 0.29 | 0.43 |
| 3-11 | 0.19 | 0.25 |
| 3-12 | 0.56 | 0.68 |
| 3-13 | 1.80 | 1.04 |
| 3-14 | 2.88 | 1.76 |
| 3-15 | 3.53 | 2.10 |
| 3-16 | 1.87 | 1.07 |
| 3-17 | 5.33 | 3.92 |
| 3-18 | 5.45 | 4.77 |
| 3-19 | 1.23 | 0.89 |
| 3-20 | 0.99 | 0.53 |
| 3-21 | 1.69 | 1.34 |
| 3-22 | 1.30 | 0.87 |
| 3-23 | 1.14 | 0.70 |

What is claimed is:
1. A compound of Formula I or a pharmaceutically acceptable salt thereof:

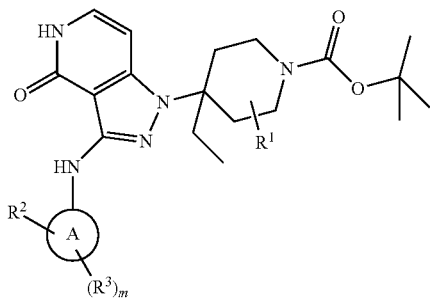

I

A is selected from aryl and heteroaryl;
m is 0, 1, or 2;
R$^1$ is selected from hydrogen, C$_{1-2}$alkyl, fluoro, and hydroxy;
R$^2$ is selected from:
  hydrogen
  halogen,
  oxo (=O),
  C$_{1-10}$ alkyl(oxy)$_{0-1}$(carbonyl)$_{0-1}$C$_{0-10}$ alkyl,
  C$_{1-10}$ heteroalkyl(oxy)$_{0-1}$(carbonyl)$_{0-1}$C$_{0-10}$ alkyl,
  aryl C$_{0-10}$ alkyl(oxy)$_{0-1}$(carbonyl)$_{0-1}$C$_{0-10}$ alkyl,
  C$_{3-12}$ cycloalkyl C$_{0-10}$ alkyl(oxy)$_{0-1}$(carbonyl)$_{0-1}$C$_{0-10}$ alkyl,
  heteroaryl C$_{0-10}$ alkyl(oxy)$_{0-1}$(carbonyl)$_{0-1}$C$_{0-10}$ alkyl,
  (C$_{3-12}$)heterocycloalkyl C$_{0-10}$ alkyl(oxy)$_{0-1}$(carbonyl)$_{0-1}$C$_{0-10}$alkyl,
  spirocyclylC$_{0-10}$ alkyl(oxy)$_{0-1}$(carbonyl)$_{0-1}$C$_{0-10}$ alkyl,
  spiroheterocyclylC$_{0-10}$ alkyl(oxy)$_{0-1}$(carbonyl)$_{0-1}$C$_{0-10}$ alkyl,
  C$_{0-10}$ alkylaminoC$_{0-10}$ alkyl,
  (C$_{1-10}$)heteroalkylaminoC$_{0-10}$alkyl,
  (C$_{1-10}$)heteroalkylaminoC$_{0-10}$alkyl,
  C$_{3-12}$ cycloalkyl C$_{0-10}$ alkylaminoC$_{0-10}$ alkyl,
  aryl C$_{0-10}$ alkylaminoC$_{0-10}$ alkyl,
  heteroaryl C$_{0-10}$ alkylaminoC$_{0-10}$ alkyl,
  (C$_{3-12}$)heterocycloalkyl C$_{0-10}$ alkylaminoC$_{0-10}$ alkyl,
  C$_{1-10}$ alkylsulfonyl,
  C$_{1-10}$ heteroalkylsulfonyl,
  (C$_{3-12}$)cycloalkylC$_{0-10}$alkylsulfonyl,
  (C$_{3-12}$) heterocycloalkylC$_{0-10}$alkylsulfonyl,
  heteroarylC$_{0-10}$ alkylsulfonyl,
  arylC$_{0-10}$ alkylsulfonyl,
  —SO$_2$NH$_2$,
  —SO$_2$NH(C$_{1-6}$alkyl),
  —SO$_2$N(C$_{1-6}$alkyl)$_2$,
  C$_{1-10}$ heteroalkylsulfamoyl,
  (C$_{3-12}$)cycloalkylC$_{0-10}$ alkylsulfamoyl,
  (C$_{3-12}$) heterocycloalkylC$_{0-10}$ alkylsulfamoyl,
  heteroarylC$_{0-10}$ alkylsulfamoyl,
  arylC$_{0-10}$ alkylsulfamoyl,
  (C$_{1-10}$ alkyl)$_{1-2}$amino,
  —CO$_2$(C$_{0-10}$ alkyl),
  —(C$_{0-10}$ alkyl)CO$_2$H,
  —SO$_2$CF$_3$,
  —SO$_2$CF$_2$H,
  —SO$_2$CH$_2$CF$_3$,
  C$_{1-10}$ alkylsulfinyl,
  C$_{1-4}$acylaminoC$_{0-10}$ alkyl,
  hydroxy,
  —(C$_{1-10}$ alkyl)OH,
  C$_{1-10}$ alkoxyC$_{0-10}$ alkyl,
  cyano,
  (C$_{1-6}$alkyl)cyano,
  cyanoC$_{1-6}$alkyl, and
  C$_{1-6}$haloalkyl;
wherein R$^2$ is optionally independently substituted by 0, 1, 2, or 3 R$^4$;
each R$^3$ independently is selected from:
  C$_{1-10}$ alkyl,
  (C$_{3-12}$)heterocycloalkyl C$_{0-10}$ alkyl,
  C$_{1-10}$ alkoxyC$_{0-10}$ alkyl,
  halogen,
  C$_{1-6}$haloalkyl, and
  oxo;
each R$^4$ independently is selected from:
  C$_{1-10}$ alkyl,
  (C$_{3-12}$)heterocycloalkyl C$_{0-10}$ alkyl,
  C$_{1-10}$ alkoxyC$_{0-10}$ alkyl,
  C$_{0-10}$ alkylaminoC$_{0-10}$ alkyl,
  halogen,
  hydroxy,
  —(C$_{1-10}$ alkyl)OH,
  C$_{1-6}$haloalkyl, and
  oxo.

2. A compound according to claim 1, wherein $R^2$ is selected from:
hydrogen
halogen,
oxo (=O),
$C_{1-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$ (carbonyl)$_{0-1}C_{0-10}$ alkyl,
$(C_{3-12})$heterocycloalkyl $C_{0-10}$ alkyl(oxy)$_{0-1}$ (carbonyl)$_{0-1}C_{0-10}$ alkyl,
spirocyclyl$C_{0-10}$ alkyl(oxy)$_{0-1}$ (carbonyl)$_{0-1}C_{0-10}$ alkyl,
spiroheterocyclyl$C_{0-10}$ alkyl(oxy)$_{0-1}$ (carbonyl)$_{0-1}C_{0-10}$ alkyl,
$C_{0-10}$ alkylamino$C_{0-10}$ alkyl,
$C_{1-10}$ alkylsulfonyl,
$(C_{3-12})$ heterocycloalkyl$C_{0-10}$alkylsulfonyl,
—SO$_2$NH($C_{1-6}$alkyl),
—SO$_2$N($C_{1-6}$alkyl)$_2$,
—($C_{0-10}$ alkyl)CO$_2$H,
—($C_{1-10}$ alkyl)OH,
$C_{1-10}$ alkoxy$C_{0-10}$ alkyl,
cyano$C_{1-6}$alkyl, and
$C_{1-6}$haloalkyl, wherein $R^2$ is optionally independently substituted by 0, 1, 2, or 3 $R^4$ or a pharmaceutically acceptable salt thereof.

3. A compound according to claim 2, wherein $R^2$ is selected from: carboxy, (8-oxa-3-azabicyclo[3.2.1]oxtane) carbonyl, cyclohexyl, piperidinyl, morpholinylcarbonyl, azepanyl, ((1R,4R)-2-oxa-5-azabicyclo[2.2.1]heptyl)carbonyl, cyanomethyl, (2-oxa-6-azaspiro[3.3]heptyl)carbonyl, thiomorpholinylcarbonyl, ((1R,4R)-2-oxa-5-azabicyclo[2.2.1]heptyl)carbonyl, (2-oxa-5-azabicyclo[2.2.1]heptyl) carbonyl, piperidinylcarbonyl pyrrolidinylcarbonyl, pyrrolidinyl, tert-butylaminomethyl, 2,2,2-trifluoroethyl, pyrrolidinylsulfonyl, fluoro, methoxymethyl, hydroxymethyl, (6-oxa-9-azaspiro[4.5]decyl)carbonyl, ((1R,5S)6-oxa-3-azabicyclo[3.1.1]heptyl)carbonyl, (6-oxa-3-azabicyclo[3.1.1]heptyl)carbonyl 1,4-thiazepanylcarbonyl, thiazepanylcarbonyl, 1,4-oxazepanylcarbonyl, oxazepanylcarbonyl, (2-oxa-5-azabixyclo[4.1.0]heptyl)carbonyl; dimethylsulfamoyl, tert-butyl, and methylsulfonyl, wherein $R^2$ is optionally independently substituted by 0, 1, 2, or 3 $R^4$ or a pharmaceutically acceptable salt thereof.

4. A compound according to claim 3, wherein A is selected from:

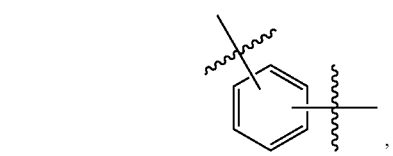

isoindolinyldiyl, pyridinyldiyl,

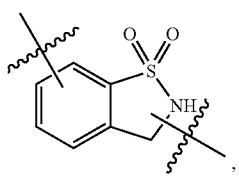

-continued

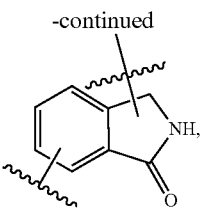

and indolinyldiyl, or a pharmaceutically acceptable salt thereof.

5. A compound according to claim 4, wherein $R^3$ independently is selected from: $C_{1-10}$ alkyl, oxo, $(C_{3-12})$heterocycloalkyl $C_{0-10}$ alkyl, $C_{1-10}$ alkoxy$C_{0-10}$ alkyl, halogen, and $C_{1-6}$haloalkyl, or a pharmaceutically acceptable salt thereof.

6. A compound according to claim 5, wherein $R^3$ independently is selected from: methyl, trifluoromethyl, ethyl, trifluoroethyl, fluoro, oxo, hydroxy, isopropyl, thiomorpholinyl, isobutyl, and difluoromethyl, or a pharmaceutically acceptable salt thereof.

7. A compound according to claim 6, wherein $R^1$ is hydrogen, and $R^4$ is selected from: methyl, fluoro, 2,2,2-trifluoroethyl, trifluoromethyl, tert-butylamino, methoxy, hydroxy, oxo, isopropyl, thiomorpholinyl, and isobutyl, or a pharmaceutically acceptable salt thereof.

8. A compound of claim 1 or a pharmaceutically acceptable salt selected from:
tert-butyl 4-(3-(4-(N,N-dimethylsulfamoyl)phenylamino)-4-oxo-4,5-dihydropyrazolo[4,3-c]pyridin-1-yl)-4-ethylpiperidine-1-carboxylate;
2-tert-butyl-5-[[1-(1-tert-butyl-6-ethyl-2-oxo-1,3-oxazocan-6-yl)-4-oxo-1H,4H,5H-pyrazolo[4,3-c]pyridin-3-yl]amino]-2,3-dihydro-1,2-benzothiazole-1,1-dione;
tert-butyl 4-ethyl-4-(3-(4-(methylsulfonyl)phenylamino)-4-oxo-4,5-dihydropyrazolo[4,3-c]pyridin-1-yl)piperidine-1-carboxylate;
tert-butyl 4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-ethylpiperidine-1-carboxylate;
tert-butyl 4-(3-(2-(4,4-difluoro-1-methylcyclohexyl)-1-oxoisoindolin-5-ylamino)-4-oxo-4,5-dihydropyrazolo[4,3-c]pyridin-1-yl)-4-ethylpiperidine-1-carboxylate;
tert-butyl 4-ethyl-4-(4-oxo-3-(4-(1-(2,2,2-trifluoroethyl)piperidin-4-yl)phenylamino)-4,5-dihydropyrazolo[4,3-c]pyridin-1-yl)piperidine-1-carboxylate;
tert-butyl 4-ethyl-4-(3-(4-(1-methylpiperidin-4-yl)phenylamino)-4-oxo-4,5-dihydropyrazolo[4,3-c]pyridin-1-yl)piperidine-1-carboxylate;
tert-butyl 4-ethyl-4-(3-{[2-(oxan-4-yl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;
(S)-tert-butyl 4-ethyl-4-(3-((3-methyl-4-(3-methylmorpholine-4-carbonyl)phenyl)amino)-4-oxo-4,5-dihydro-1H-pyrazolo[4,3-c]pyridin-1-yl)piperidine-1-carboxylate;
tert-butyl 4-ethyl-4-(3-((3-methyl-4-(3-methylmorpholine-4-carbonyl)phenyl)amino)-4-oxo-4,5-dihydro-1H-pyrazolo[4,3-c]pyridin-1-yl)piperidine-1-carboxylate;
(R)-tert-butyl-4-ethyl-4-(3-(3-methyl-4-(2-methylmorpholine-4-carbonyl)phenyl)amino)-4-oxo-4,5-dihydro-pyrazolo[4,3-c]pyridin-1-yl)piperidine-1-carboxylate;
(S)-tert-butyl-4-ethyl-4-(3-(3-methyl-4-(2-methylmorpholine-4-carbonyl)phenyl)amino)-4-oxo-4,5-dihydro-pyrazolo[4,3-c]pyridin-1-yl)piperidine-1-carboxylate;

- tert-butyl-4-ethyl-4-(3-(3-methyl-4-(2-methylmorpholine-4-carbonyl)phenylamino)-4-oxo-4,5-dihydropyrazolo[4,3-c]pyridin-1-yl)piperidine-1-carboxylate;
- tert-butyl 4-ethyl-4-((3-methyl-4-(morpholine-4-carbonyl)phenyl)amino)-4-oxo-4,5-dihydro-1H-pyrazolo[4,3-c]pyridin-1-yl)piperidine-1-carboxylate;
- (R)-tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
- (S)-tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
- tert-butyl 4-ethyl-4-(4-oxo-3-((4-(2-(trifluoromethyl)azepan-2-yl)phenyl)amino)-4,5-dihydro-1H-pyrazolo[4,3-c]pyridin-1-yl)piperidine-1-carboxylate;
- tert-butyl-4-ethyl-4-(3-(3-methyl-4-(morpholine-4-carbonyl)phenylamino)-4-oxo-4,5-dihydropyrazolo[4,3-c]pyridin-1-yl)piperidine-1-carboxylate;
- tert-butyl 4-ethyl-4-(3-((3-fluoro-4-(morpholine-4-carbonyl)phenyl)amino)-4-oxo-4,5-dihydro-1H-pyrazolo[4,3-c]pyridin-1-yl)piperidine-1-carboxylate;
- tert-butyl 4-(3-((4-(3-oxa-8-azabicyclo[3.2.1]octane-8-carbonyl)-3-methylphenyl)amino)-4-oxo-4,5-dihydro-1H-pyrazolo[4,3-c]pyridin-1-yl)-4-ethylpiperidine-1-carboxylate;
- tert-butyl 4-ethyl-4-(3-((3-methyl-4-(2-oxa-6-azaspiro[3.3]heptane-6-carbonyl)phenyl)amino)-4-oxo-4,5-dihydro-1H-pyrazolo[4,3-c]pyridin-1-yl)piperidine-1-carboxylate;
- tert-butyl 4-(3-((4-((1R,4R)-2-oxa-5-azabicyclo[2.2.1]heptane-5-carbonyl)-3-methylphenyl)amino)-4-oxo-4,5-dihydro-1H-pyrazolo[4,3-c]pyridin-1-yl)-4-ethylpiperidine-1-carboxylate
- tert-butyl 4-(3-((3-(cyanomethyl)phenyl)amino)-4-oxo-4,5-dihydro-1H-pyrazolo[4,3-c]pyridin-1-yl)-4-ethylpiperidine-1-carboxylate;
- tert-butyl 4-(3-(4-((3S,5R)-3,5-dimethylmorpholine-4-carbonyl)-3-methylphenylamino)-4-oxo-2,3,4,5-tetrahydropyrazolo[4,3-c]pyridin-1-yl)-4-ethylpiperidine-1-carboxylate;
- tert-butyl 4-(3-(4-((3R,5R)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;
- tert-butyl 4-(3-(4-((3S,5S)-3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;
- tert-butyl 4-(3-(4-(3,5-dimethylmorpholine-4-carbonyl)-3-methylphenylamino)-4-oxo-4,5-dihydropyrazolo[4,3-c]pyridin-1-yl)-4-ethylpiperidine-1-carboxylate;
- tert-butyl 4-ethyl-4-(3-(3-methyl-4-(thiomorpholine-4-carbonyl)phenylamino)-4-oxo-4,5-dihydropyrazolo[4,3-c]pyridin-1-yl)piperidine-1-carboxylate;
- tert-butyl 4-(3-(4-((1S,4S)-5-oxa-2-aza-bicyclo[2.2.1]heptane-2-carbonyl)-3-methylphenylamino)-4-oxo-4,5-dihydropyrazolo[4,3-c]pyridin-1-yl)-4-ethylpiperidine-1-carboxylate;
- tert-butyl 4-ethyl-4-(4-oxo-3-(4-(piperidin-4-yl)phenylamino)-4,5-dihydropyrazolo[4,3-c]pyridin-1-yl)piperidine-1-carboxylate;
- tert-butyl 4-ethyl-4-(3-((3-ethyl-4-(morpholine-4-carbonyl)phenyl)amino)-4-oxo-4,5-dihydro-1H-pyrazolo[4,3-c]pyridin-1-yl)piperidine-1-carboxylate;
- tert-butyl 4-(3-(3-(difluoromethyl)-4-(thiomorpholine-4-carbonyl)phenylamino)-4-oxo-4,5-dihydropyrazolo[4,3-c]pyridin-1-yl)-4-ethylpiperidine-1-carboxylate;
- tert-butyl 4-(3-(4-(4,4-difluoropiperidine-1-carbonyl)-3-methylphenylamino)-4-oxo-4,5-dihydropyrazolo[4,3-c]pyridin-1-yl)-4-ethylpiperidine-1-carboxylate;
- tert-butyl-4-ethyl-4-(3-(3-methyl-4-(thiomorpholine-4-carbonyl)phenylamino)-4-oxo-4,5-dihydropyrazolo[4,3-c]pyridin-1-yl)piperidine-1-carboxylate;
- (R)-tert-butyl-4-ethyl-4-(3-(3-methyl-4-(3-methylmorpholine-4-carbonyl)phenylamino)-4-oxo-4,5-dihydropyrazolo[4,3-c]pyridin-1-yl)piperidine-1-carboxylate;
- tert-butyl 4-ethyl-4-(3-(3-ethyl-4-(thiomorpholine-4-carbonyl)phenylamino)-4-oxo-4,5-dihydropyrazolo[4,3-c]pyridin-1-yl)piperidine-1-carboxylate;
- tert-butyl 4-ethyl-4-(3-((2-(1-methylpiperidin-4-yl)-1,1-dioxido-2,3-dihydrobenzo[d]isothiazol-5-yl)amino)-4-oxo-4,5-dihydro-1H-pyrazolo[4,3-c]pyridin-1-yl)piperidine-1-carboxylate;
- (S)-tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;
- (R)-tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;
- tert-butyl 4-ethyl-4-(4-oxo-3-((4-(2-(trifluoromethyl)piperidin-2-yl)phenyl)amino)-4,5-dihydro-1H-pyrazolo[4,3-c]pyridin-1-yl)piperidine-1-carboxylate;
- tert-butyl 4-ethyl-4-(3-(3-methyl-4-(pyrrolidine-1-carbonyl)phenylamino)-4-oxo-4,5-dihydropyrazolo[4,3-c]pyridin-1-yl)piperidine-1-carboxylate;
- (S)-tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;
- (R)-tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;
- tert-butyl 4-ethyl-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;
- (R)-tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;
- (S)-tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;
- tert-butyl 4-(3-(4-(1-(tert-butylamino)-2,2,2-trifluoroethyl)phenylamino)-4-oxo-4,5-dihydropyrazolo[4,3-c]pyridin-1-yl)-4-ethylpiperidine-1-carboxylate;
- (S)-tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;
- (R)-tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;
- tert-butyl 4-ethyl-4-(3-(4-(2-methylpyrrolidin-1-ylsulfonyl)phenylamino)-4-oxo-4,5-dihydropyrazolo[4,3-c]pyridin-1-yl)piperidine-1-carboxylate;
- tert-butyl 4-ethyl-4-(3-(2-fluoropyridin-4-ylamino)-4-oxo-4,5-dihydropyrazolo[4,3-c]pyridin-1-yl)piperidine-1-carboxylate;
- (S) tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;
- (R) tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;
- tert-butyl 4-ethyl-4-(4-oxo-3-((4-(2,2,2-trifluoro-1-methoxyethyl)phenyl)amino)-4,5-dihydro-1H-pyrazolo[4,3-c]pyridin-1-yl)piperidine-1-carboxylate;

(R) tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(S) tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

tert-butyl 4-ethyl-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(S) tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

(R) tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

tert-butyl 4-ethyl-4-(4-oxo-3-((4-(2,2,2-trifluoro-1-hydroxyethyl)phenyl)amino)-4,5-dihydro-1H-pyrazolo[4,3-c]pyridin-1-yl)piperidine-1-carboxylate;

4-((1-(1-(tert-butoxycarbonyl)-4-ethylpiperidin-4-yl)-4-oxo-4,5-dihydro 1H-pyrazolo[4,3-c]pyridin-3-yl)amino)-2-methylbenzoic acid;

tert-butyl-4-ethyl-4-(3-((3-methyl-4-(2-oxomorpholine-4-carbonyl)phenyl)amino)-4-oxo-4,5-dihydro-1H-pyrazolo[4,3-c]pyridin-1-yl)piperidine-1-carboxylate;

tert-butyl 4-[3-({4-[(2,2-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-(3-{[3-methyl-4-(6-oxa-9-azaspiro[4.5]dec-9-ylcarbonyl)phenyl]amino}-4-oxo-4,5-dihydro-1H-pyrazolo[4,3-c]pyridin-1-yl)piperidine-1-carboxylate;

tert-butyl 4-{3-[(4-{[(2R,6S)-2,6-dimethylmorpholin-4-yl]carbonyl}-3-methylphenyl)amino]-4-oxo-4,5-dihydro-1H-pyrazolo[4,3-c]pyridin-1-yl}-4-ethylpiperidine-1-carboxylate;

tert-butyl 4-[3-({4-[(3,3-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-[3-({3-methyl-4-[(1R,5S)-6-oxa-3-azabicyclo[3.1.1]hept-3-ylcarbonyl]phenyl}amino)-4-oxo-4,5-dihydro-1H-pyrazolo[4,3-c]pyridin-1-yl]piperidine-1-carboxylate;

tert-butyl 4-{3-[(4-{[(2S,6S)-2,6-dimethylmorpholin-4-yl]carbonyl}-3-methylphenyl)amino]-4-oxo-4,5-dihydro-1H-pyrazolo[4,3-c]pyridin-1-yl}-4-ethylpiperidine-1-carboxylate;

tert-butyl 4-ethyl-4-{3-[(3-methyl-4-{[(3R)-3-(1-methylethyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-(3-{[3-methyl-4-(1,4-thiazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-(3-{[3-methyl-4-(1,4-oxazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({3-methyl-4-[(1-oxidothiomorpholin-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-{3-[(3-methyl-4-{[(3R)-3-(1-methylethyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-(3-{[3-methyl-4-(1,4-thiazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-(3-{[3-methyl-4-(1,4-oxazepan-4-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({3-methyl-4-[(1-oxidothiomorpholin-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(4-thiomorpholin-4-ylpiperidin-1-yl)carbonyl]phenyl}amino)-4-oxo-4,5-dihydro-1H-pyrazolo[4,3-c]pyridin-1-yl]piperidine-1-carboxylate;

tert-butyl 4-[3-({4-[(2,3-dimethylmorpholin-4-yl)carbonyl]-3-methylphenyl}amino)-4-oxo-4,5-dihydro-1H-pyrazolo[4,3-c]pyridin-1-yl]-4-ethylpiperidine-1-carboxylate;

tert-butyl 4-ethyl-4-{3-[(3-methyl-4-{[3-(2R-methylpropyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-{3-[(3-methyl-4-{[3-(2S-methylpropyl)morpholin-4-yl]carbonyl}phenyl)amino]-4-oxo-4,5-dihydro-1H-pyrazolo[4,3-c]pyridin-1-yl}piperidine-1-carboxylate;

tert-butyl 4-ethyl-4-{3-[(3-methyl-4-{[3-(methylpropyl)morpholin-4-yl]carbonyl}phenyl)amino-4-oxo-4,5-dihydro-1H-pyrazolo[4,3-c]pyridin-1-yl}piperidine-1-carboxylate;

tert-butyl 4-ethyl-4-[3-({3-methyl-4-[(methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(6R-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3-methyl-4-[(6S-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-(3-{[3-methyl-4-(2-oxa-5-azabicyclo[4.1.0]hept-5-ylcarbonyl)phenyl]amino}-4-oxo-4,5-dihydro-1H-pyrazolo[4,3-c]pyridin-1-yl)piperidine-1-carboxylate;

tert-butyl 4-ethyl-4-[3-({methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate;

tert-butyl 4-ethyl-4-[3-({3R-methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate; and tert-butyl 4-ethyl-4-[3-({3S-methyl-4-[(2-methyl-1,4-oxazepan-4-yl)carbonyl]phenyl}amino)-4-oxo-4,5-dihydro-1H-pyrazolo[4,3-c]pyridin-1-yl]piperidine-1-carboxylate.

9. A pharmaceutical composition comprising a compound of claim 1 or a pharmaceutically acceptable salt thereof or a pharmaceutically acceptable carrier.

10. A method of treating a condition in a mammal that can be ameliorated by the inhibition of Janus kinases JAK1 and JAK 2 which condition is selected from, arthritis, asthma and obstructive airways diseases, autoimmune diseases or disorders, and cancer comprising administering to the mammal in need of such treatment, a therapeutically effective amount of a compound according to claim 1 or a pharmaceutically acceptable salt thereof.

11. A method according to claim 10, wherein said condition is arthritis.

12. A method according to claim 11, wherein said condition is selected from rheumatoid arthritis, juvenile arthritis, and psoriatic arthritis.

13. A method according to claim 12, wherein said condition is asthma or obstructive airways diseases.

14. A method according to claim 13, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease (COPD), and emphysema.

15. A method according to claim 10, wherein said condition is autoimmune diseases or disorders.

16. A method of treating asthma in a mammal in need thereof, comprising administering a therapeutically effective amount of a compound according to claim 1 or a pharmaceutically acceptable salt thereof.

17. A method of treating arthritis in a mammal in need thereof, comprising administering a therapeutically effective amount of a compound according to claim 1 or a pharmaceutically acceptable salt thereof.

* * * * *